United States Patent
Rigler et al.

(10) Patent No.: US 6,582,903 B1
(45) Date of Patent: Jun. 24, 2003

(54) METHOD AND A DEVICE FOR THE EVALUATION OF BIOPOLYMER FITNESS

(75) Inventors: Rudolf Rigler, Gottingen (DE); Manfred Eigen, Gottingen (DE); Karsten Henco, Erkrath (DE); Ulo Mets, Tallin (EE); Jerker Widengren, Solna (SE); Michael Stuke, Gottingen (DE); Michael Brinkmeyer, Gottingen (DE); Wolfgang Simm, Rosdorf (DE); Olaf Lehmann, Gottingen (DE)

(73) Assignee: Evotec OAI AG, Hamburg (DE)

( * ) Notice: Subject to any disclaimer, the term of this patent is extended or adjusted under 35 U.S.C. 154(b) by 0 days.

(21) Appl. No.: 09/021,410

(22) Filed: Feb. 10, 1998

Related U.S. Application Data

(62) Division of application No. 08/491,888, filed as application No. PCT/EP93/01291 on May 22, 1993.

(30) Foreign Application Priority Data

Jan. 18, 1993 (DE) ............................ 43 01 005
Dec. 15, 1993 (DE) ............................ 43 42 703

(51) Int. Cl.$^7$ ............................................. G01N 33/543
(52) U.S. Cl. ............................. 435/6; 356/36; 356/302; 356/306; 356/311; 356/319; 356/320; 356/335; 422/55; 422/58; 422/99; 435/7.1; 435/287.1; 435/287.2; 435/288.7; 435/808; 436/517; 436/518; 436/805; 436/34; 436/43
(58) Field of Search .................... 435/6, 7.1, 287.1, 435/287.2, 288.7, 808; 436/501, 517, 518, 34, 43, 805; 422/55, 58, 99, 129, 186; 356/36, 302, 306, 311, 319, 320, 335

(56) References Cited

U.S. PATENT DOCUMENTS

| 3,872,312 A | * | 3/1975 | Hirschfeld ............... 250/458 |
|---|---|---|---|
| 4,405,237 A | | 9/1983 | Manuccia et al. |
| 5,223,408 A | | 6/1993 | Goeddel et al. |
| 5,252,743 A | * | 10/1993 | Barrett et al. ............... 548/303 |
| 5,381,224 A | * | 1/1995 | Dixon et al. ............... 356/72 |
| 5,608,519 A | * | 3/1997 | Gourley et al. ............ 356/318 |
| 5,720,928 A | * | 2/1998 | Schwartz .................. 422/186 |
| 5,760,951 A | * | 6/1998 | Dixon et al. ............... 359/385 |

FOREIGN PATENT DOCUMENTS

| EP | 0 245 206 | 4/1987 |
|---|---|---|
| EP | 0 319 815 | 11/1988 |
| EP | 0 501 688 | 2/1992 |
| WO | WO9201513 | 2/1992 |

OTHER PUBLICATIONS

Eigen et al. Sorting single molecules: application to diagnostics and evolunionary biology. PNAS–USA. 91:5740–5747, Jun. 1994.*

Meyer et al. Particle counting by fluorescence correlation spectroscopy. Biophys. J. 54:983–993, Dec. 1988.*

Thompson et al. Immunoglobulin surface–binding kinetics studied by total internal reflection with fluorescence correlation spectroscopy. Biophys. J. 43:103–114, Jul. 1983.*

Kask et al. Fluorescence correlation spectroscopy in the nanosecond range: photon antibunching in dye fluorescence. Eur. Biophys. J. 12:163–166, Feb. 26, 1985.*

(List continued on next page.)

*Primary Examiner*—Christopher L. Chin
(74) *Attorney, Agent, or Firm*—Jacobson Holman PLLC

(57) ABSTRACT

A method for identifying one or a small number of molecules, especially in a dilution of $\leq 1$ $\mu$M, using laser excited FCS with measuring times $\leq 500$ ms and short diffusion paths of the molecules to be analyzed, wherein the measurement is performed in small volume units of preferably $\leq 10^{-14}$ l, by determining material-specific parameters which are determined by luminescence measurements of molecules to be examined.

115 Claims, 32 Drawing Sheets

OTHER PUBLICATIONS

Rigler et al. Interactions and kinetics if single molecule as observed by fluorescnece correlation spectroscopy. In Fluorescence Specroscopy, New Methods and Applications (Ed. Wolfbeis). Springer–Verlag, Dec. 1992.*

Sorscher et al. The use of fluorescence correlation spectroscopy to probe chromatin in the cell nucleus. Bioch. Biophys. Acta. 610:28–46, 1980.*

S. Harada et al, MICROBIOLOGY AND IMMUNOLOGY, "Induced CD25 Expression . . . " Feb. 1992, vol. 36, No. 5, pps. 479–494.

A. Yasuda, JOURNAL OF VIROLOGY, "Induction of Protective . . . ", Jun. 1990, vol. 64, No. 6, pps. 2788–2795.

R. Teasdale, THE JOURNAL OF BIOLOGICAL CHEMISTRY, "The Signal for Gilgi Retention . . . ", Feb. 1992, vol. 267, No. 6, pps. 4084–4097.

Rigler et al., "Interactions and Kinetics of Single Molecules as Observed by Fluorescence Correlation Spectroscopy," *Fluorescence Spectroscopy*, 13–24 (1982).

Rigler, et al., "Ultrasensitive Detection of Single Molecules By Fluorescence Correlation Spectroscopy," *Bioscience*, 180–183 (1990).

Palmer, et al., "Optical spatial intensity profiles for high order autocorrelation in fluorescence spectroscopy," *Applied Optics*, 28(6):1214–1220 (1989).

Rigler, et a., "Diffusion of Single Molecules Through a Gaussian Laser Beam," *Laser Spectroscopy of Biomolecules*. 1921:239–247 (1992).

Rička et al., "Direct Measurement of a distinct correcation function by fluorescence cross correlation," *The American Physical Society*, 39(5):2646–2652 (1989).

Thompson, "Fluorescence Correlation Spectroscopy," *Topics in Fluorescence Spectroscopy*, vol. 1: *Techniques*, 337–378 (1991).

* cited by examiner

FIG. 1
Receptor Assay (1)
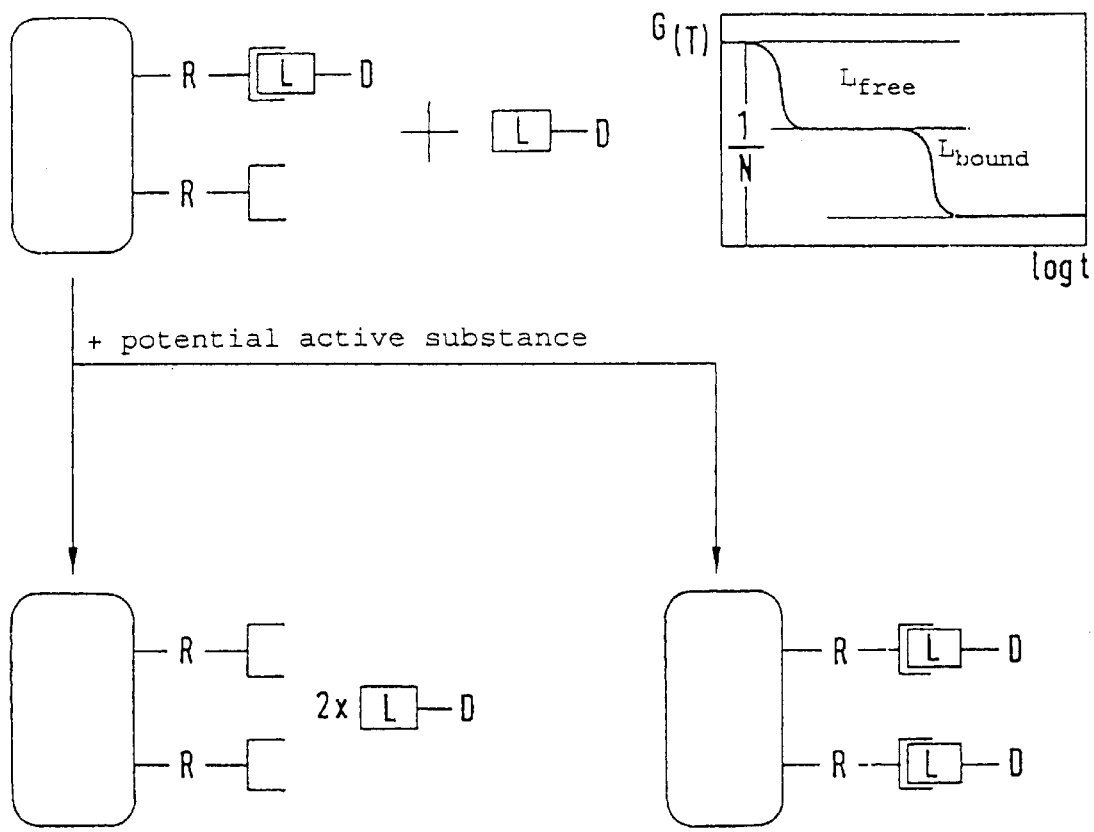
+ potential active substance
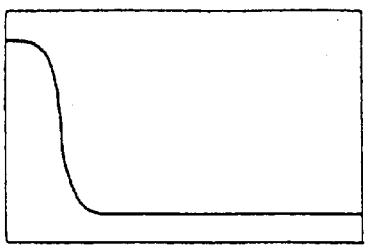
- antagonistic activator
- antagonistic blocker
- allosteric blocker
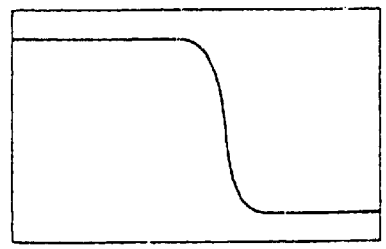
- allosteric complex stabilizer
  (blocker or activator)

FIG. 2
Receptor Assay (2)
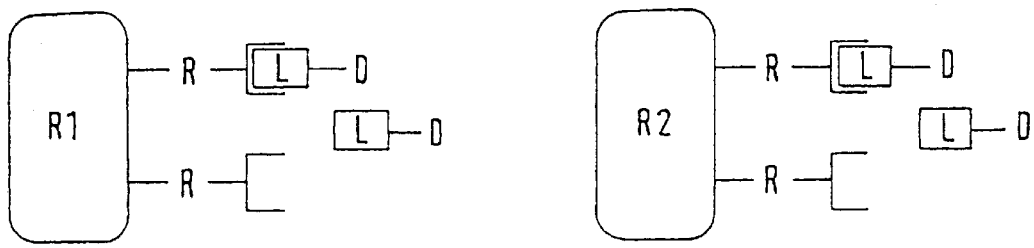
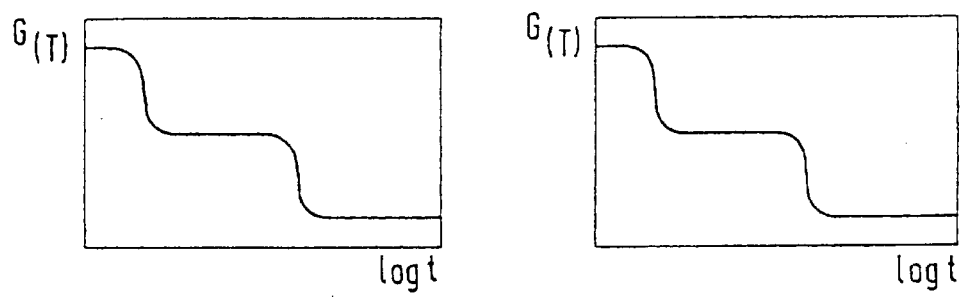
+ potential active substance
separation of receptor functions | interference acting in the same direction
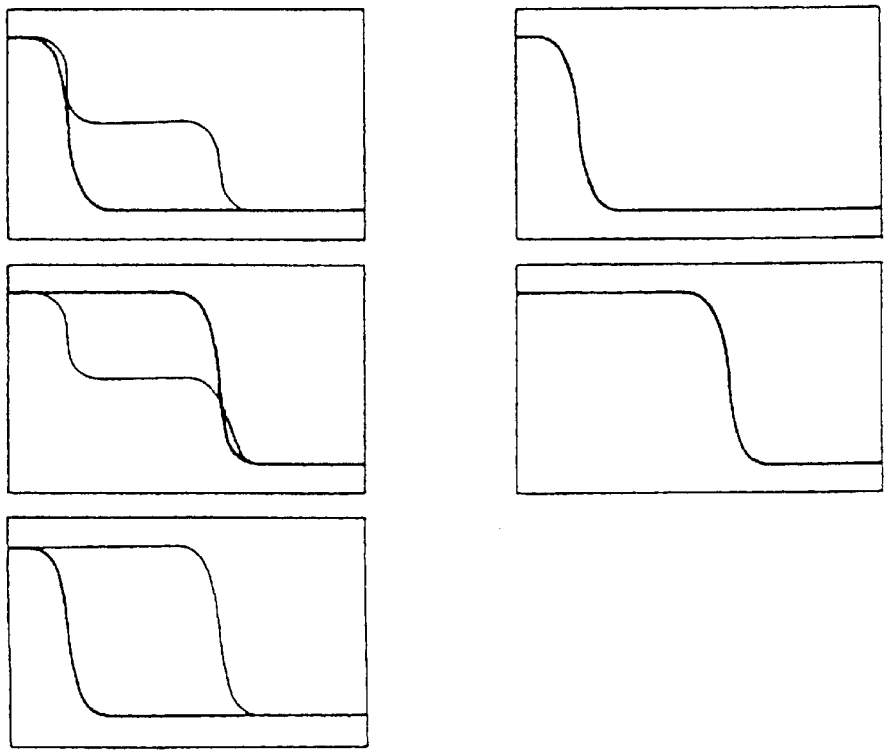

FCS Analysis with Multi Well Sheets

Detection of Molecules on
stationary structures through
relative temporal change of the
positional coordinates of the
measuring volume Detection of Single Molecules
in the Electric Trap FCS - Tagging of the Selected Genotypes a) Physical access to optically tagged volume elements b) Light induced linking of the nucleic acid of selected volume elements to affinity ligands
- at the carrier surface
- to soluble ligands

FIG. 8

Preparation of the DNA/RNA of
FCS Selected Genotypes

Mixture of all nucleic acids
after phenotype evaluation:

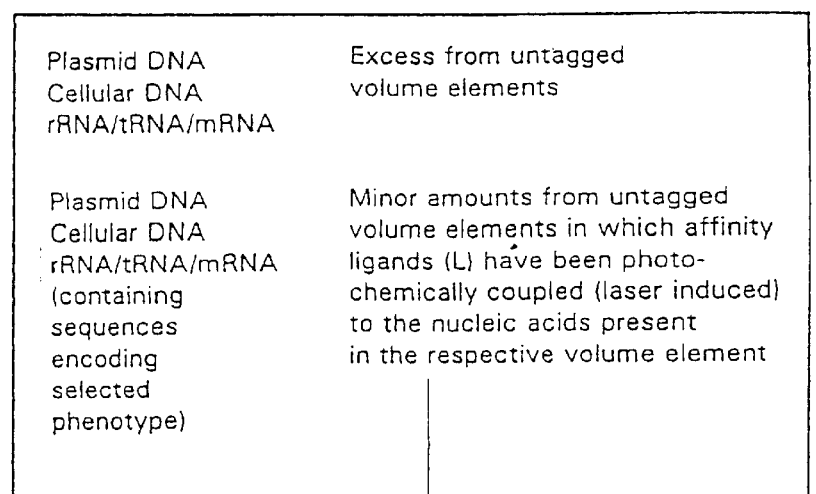

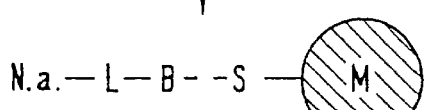

cDNA synthesis or
enzymatic amplification

N.a.; Nucleic acid.
L; Ligand with specific nucleic acid affinity which can be photochemically coupled covalently and preferably reversibly to a nucleic acid (e.g. a psoralen derivative). The ligand is preferably linked to a substituent which allows for subsequent enrichment of the nucleic acids. For instance, this can be a hydrophobic substituent to purify nucleic acids by reversed phase chromatography. For affinity chromatography, substituents such as biotin (B) are the obvious suitable ones so that the nucleic acids can be enriched through (strept)avidin complexing (S) with appropriately modified magnetobeads (M) or surfaces.

FLUCS Analysis of Complex Mixtures of Substances after Chromatographic Separation in Fractions Laser Correlation Microscope

FIG. 11
Selection of Possible Assays
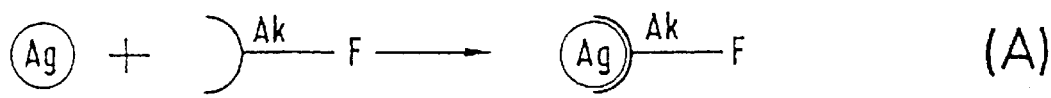 (A)
 (B)
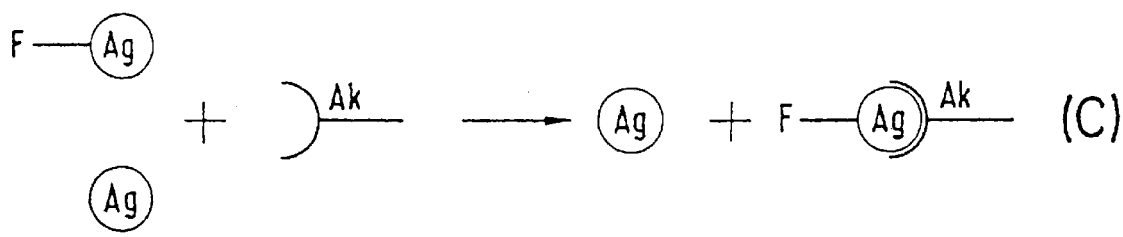 (C)
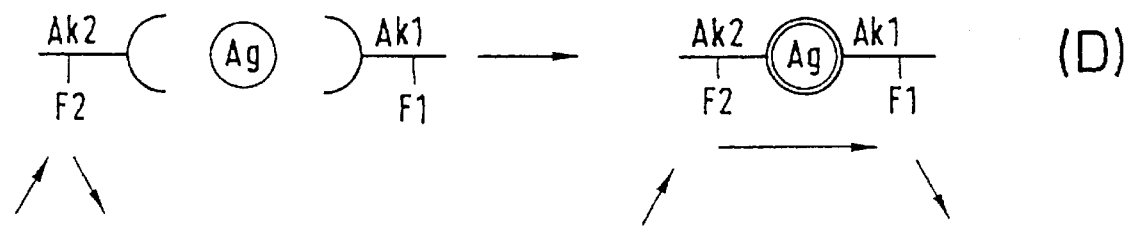 (D)
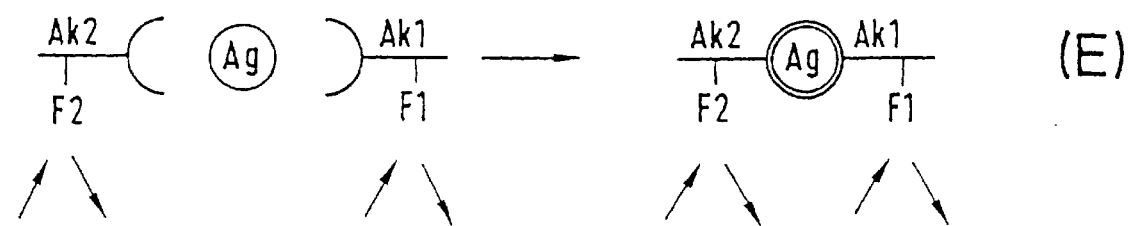 (E)

Electrophoresis Cell

Determination by FCS of the Dissociation Behavior of Complexes in Experiments Performed in Parallel Different Embodiments of the Electric Trap According to the Invention Molecular Detection Small Excitation Volumes (a) and
Small Measuring Volumes (b) and Small
Volumes with Parallel Measurements (c)

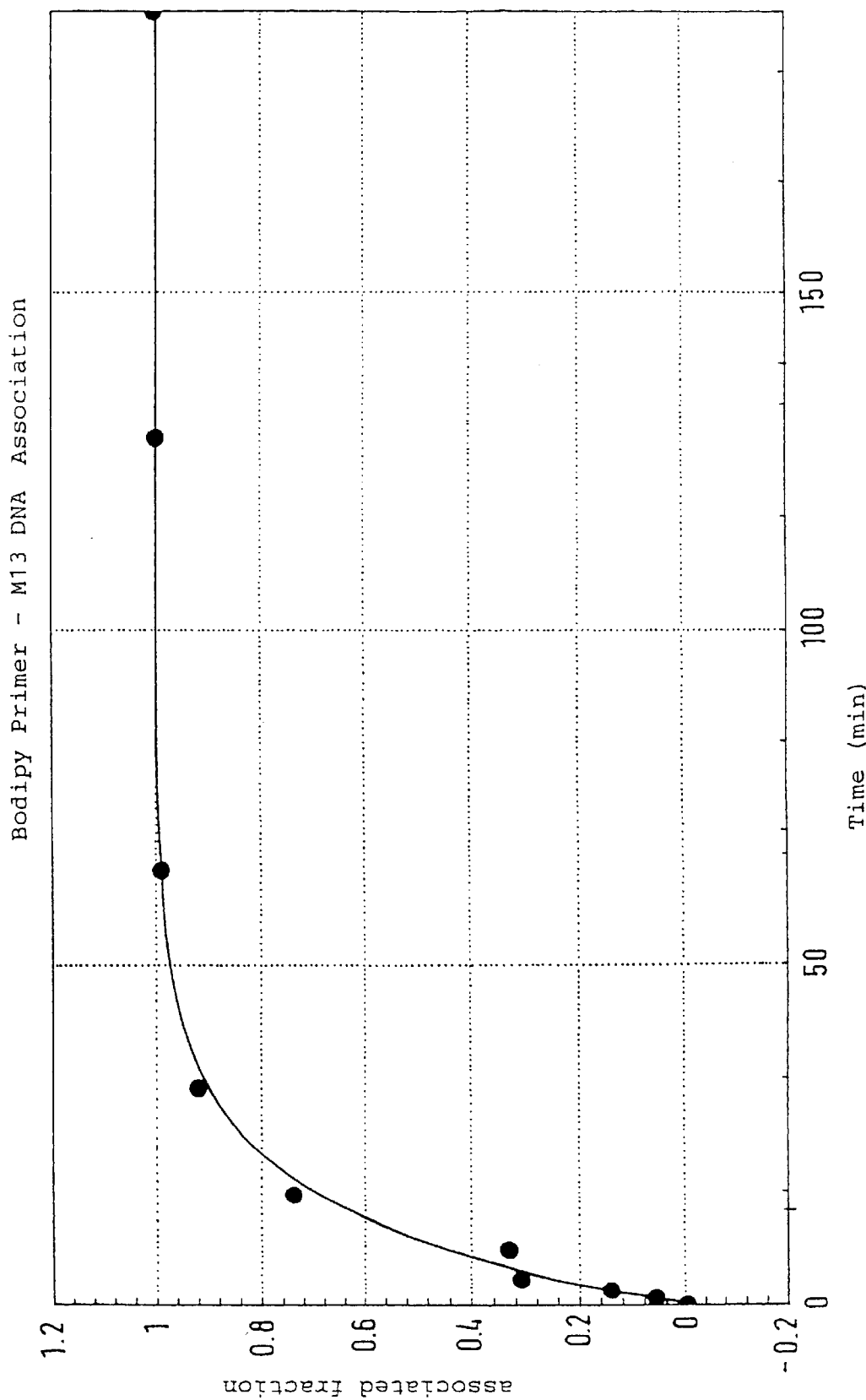

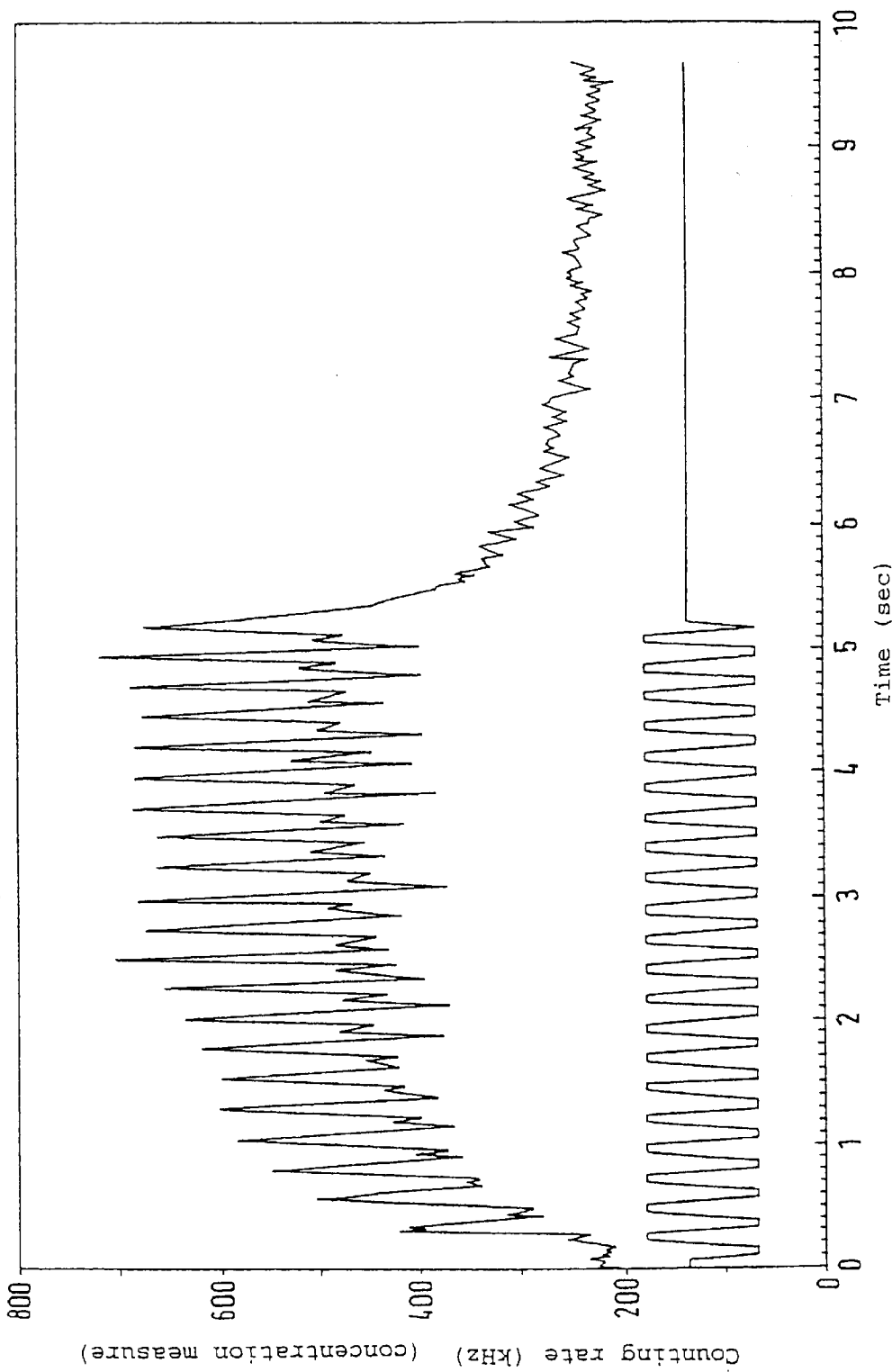

Multichannel Detection of Rhodamine 6G (Single Molecules)

METHOD AND A DEVICE FOR THE EVALUATION OF BIOPOLYMER FITNESS

This is a division of application Ser. No. 08/491,888, filed Jul. 18, 1995, which is as 371 of PCT/EP94/00117, filed Jan. 18, 1994.

The object of the present invention is a method for identifying one or a small number of molecules, especially in a dilution of $\leq 1$ μM, using laser excited fluorescence correlation spectroscopy, the use of said method in particular applications, as well as a device for performing the method according to the invention.

In recent years, analysis of biologically active molecules has been constantly improved in terms of specificity and sensitivity and supplemented by basically novel techniques. In this context, we may refer to cloning methods or the methods of enzyme-based amplification of genetic material to amplify single cells or molecules to such a number that they become apt to conventional analysis. In many cases, however, it would be more advantageous if analytic methods were sufficiently sensitive to qualitatively and quantitatively apply directly to single molecules or ensembles of a few molecules.

Electron microscopy, for instance, is a technique that can detect single molecules. Thus, attempts are made to sequence single DNA molecules by means of tunnel electron microscopy. This is very laborious, however.

Beyond the mere analysis of single molecules, information about state parameters of the molecules, such as their conformations and interactions with other molecules or molecular structures, are important in many fields.

Modern methods of evolutive biological engineering are concerned with highly complex collectives of molecules. Their object is to identify molecules having specific properties of interaction with target structures, that is to measure a particular fitness with respect to a desired function. Such fitness can be reduced to thermodynamic parameters such as binding constants or rate constants.

Sometimes it is less critical for the solution of particular problems to increase the sensitivity of an assay method, for instance when the molecule to be analyzed is present only in small concentrations. Rather, a very large number of samples which have to be analyzed more or less simultaneously must be coped with. If for instance $10^6$ analyses have to be performed within a period of hours, it is obvious that only an analytic method can be considered where the samples can be measured and evaluated within a period of about 1 ms to 1 s as a maximum. The problem underlying the invention is, inter alia, to provide a method which, beyond the mere detection of single molecules, allows for informations about their specific interactions with other molecules or molecular structures to be obtained. Moreover, a very large number of samples is to be analyzed virtually simultaneously.

The method according to the invention is based on a luminescence detection and makes use of a technique which is known per se under the name of fluorescence correlation spectroscopy (FCS). Chromophorous molecular structures having fluorescence properties can be used to obtain information about the molecular environment of a chromophorous ligand. Rotational diffusion and translational diffusion of a luminophore may be measured as well as different paths of energy transfer to interacting molecules, chemical kinetics and the lifetime of excited states.

Based on physicochemical phenomena known per se, the method according to the invention provides novel solutions, making use of spectroscopic measuring parameters, for obtaining information from single molecules or a small number of molecules about the nature of said molecules as well as information about their fitness with respect to a particular interactional function or about the populations of different states of a luminophore which are defined with respect to one molecule.

To date, the method of fluorescence correlation spectroscopy as pursued by the groups of D. Magde (Elson, E. L. & Magde, D. (1974) Fluorescence correlation spectroscopy; Conceptional basis and theory; Biopolymers 13, 1–27) and R. Rigler (Ehrenberg, M. & Rigler, R. (1974) Rotational Brownian motion and fluorescence intensity fluctuations; Chem. Phys. 4, 390–401) for nearly twenty years could not be technically incorporated into a practicable analytical method without difficulty. It has not been possible to meet the above mentioned requirements with respect of measuring times and the light induced bleaching (photobleaching) of the dyes. Rigler et al. were able to determine rotational times of molecules. Magde et al. were able to determine some chemical reaction constants through fluctuation times.

The principle of measurement of FCS is to measure fluorophorous molecules in extremely diluted solutions ($\leq 10$ nM) by exposing a relatively small volume element of the solution to the intense exciting light of a laser. Only the molecules having a corresponding exciting spectrum which are present in this same volume are excited by the light. Then, an image of the emitted fluorescence from this volume element can be formed on a photomultiplier with high sensitivity. If the solutions are diluted, significant variations of the concentration of the molecules present in the respective volume element will arise.

In particular, very diluted solutions will exhibit a Poisson distribution of the number of molecules which are simultaneously present within the volume element in a certain period of time. A molecule which has once diffused into the volume element will leave the volume element again within an average yet characteristic, for this type of molecule, period of time according to its characteristic diffusion rate (translational) and hence will not be observable any longer.

Now, if the luminescence of one and the same molecule can be excited many times during its average dwelling time within the respective observation element, many luminescence signals from this molecule can be detected. In other words, the probability that a molecule which has once diffused into the observation element can be excited once more before it will leave the volume element again is much greater in diluted solutions than would be true for a freshly entering molecule. Though this means that with a correspondingly great possibility the corresponding luminescence signal comes from one and the same molecule rather than from a molecule which has freshly entered the element. Hence, a correlation between the change with time of the incoming emission signals and the relative diffusion times of the molecular species involved can be established.

If the rotation of the polarization plane of exciting light and emitted light is measured as a further parameter, then the rotational diffusion coefficient of the molecules involved from which conclusions about molecular weight, shape parameters or the surrounding matrix can be obtained may also be determined.

It becomes evident that it is even possible to detect single molecules in diluted solutions by exciting one and the same molecule very often (several thousand times) and accumulating the corresponding luminescence signal from many single measurements.

The realization of this measuring principle in practice was impeded by many technical difficulties. Although modern laser technology was employed, the observation element was so large that biologically interesting molecules having low translational diffusion coefficients were present in the observation element during a period whose order of magnitude was about 50 ms. Such a period is significantly too large since it causes strong bleaching of the respective dye ligands employed serving as the luminophore. Frequent excitation increases the chemical reactivity of the luminophorous structure towards molecules of the environment, in particular oxygen, whereby the luminescence is altered or quenched. Of course, photobleaching also leads directly to false measuring data, since loss of luminescence (fluorescence) simulates the molecule's leaving the measuring element and a distinction by standardizing the measuring method is hardly possible or can only be attained by unduly great technical expenditure.

To date, the wide practical realization of this measuring principle in a generally applicable method was hence restricted to within narrow limits which will be overcome, however, by the method according to the invention.

The critical breakthrough on the way to a routine method for the tasks of FCS as defined above according to the invention is achieved by the introduction of ultrasmall measuring volumes (preferably $10^{-14}$–$10^{-17}$ l), with total volumes of the sample being in the $\mu$l-range, the realization of which requires the simultaneous use, according to the invention, of particular elements of excitation optics, single photon detection and sample handling. The measuring volume of the device described in the experimental layouts is $2 \times 10^{-16}$ l which is about 1000 times as small as the measuring volumes described in the literature. Hence, the illuminated area has an approximate dimension of 0.1 $\mu m^2$. Supposing that FCS provides correct data in particular for a concentration of chromophorous molecules of 0.1–10 molecules per measuring element volume, the working concentration will be about $10^{-7}$–$10^{-9}$ M. Measurements with maximum detection efficiency and background discrimination can be technically realized by using confocal optics with high apertures in combination with single photon detection.

Binding constants can then be determined through translational diffusion if reaction time is slow compared with diffusion time. That means that a ligand which is to be observed does not change or changes but hardly its molecular structure during its entering into the measuring compartment and its leaving the same. Otherwise only a correlation is measured describing the mixed state. Here again, the importance of the method according to the invention using very small measuring volumes becomes evident, since the dwelling time of a molecule is about 1000 times shorter than with conventional compartments and hence opens up the usual dimensions of equilibrium constants and rate constants of specific biological recognition reactions, for example ligand/receptor interactions, for measurement.

1. The Significance of the Small Volume Elements According to the Invention

According to the invention, the significance of the small volume elements for the performance of the methods according to the invention and the uses thereof has different, experimentally distinguishable aspects.

The significance of the small volume elements should be seen under the following aspects:

background scattered radiation, especially Raman radiation, life of fluorescence dyes under light exposure, short measuring times, diffusion times of macromolecular complexes, viruses, cells, integrity/preservation of the complexes not present in the volume element, and life of complexes during measurement.

BRIEF DESCRIPTION OF THE DRAWINGS

FIGS. 1 and 2 are flow charts of receptor assays.

FIG. 8 is a flow chart illustrating the preparation of DNA/RNA of FCS-selected genotypes.

FIGS. 11(A)–(E) is a flow chart illustrating the selection of possible assays.

FIGS. 26a, 26b, 26c, 27, 28a, 28b, 28c, 29, 30, 31a, and 31b are graphs depicting measurement results.

Figure 3:
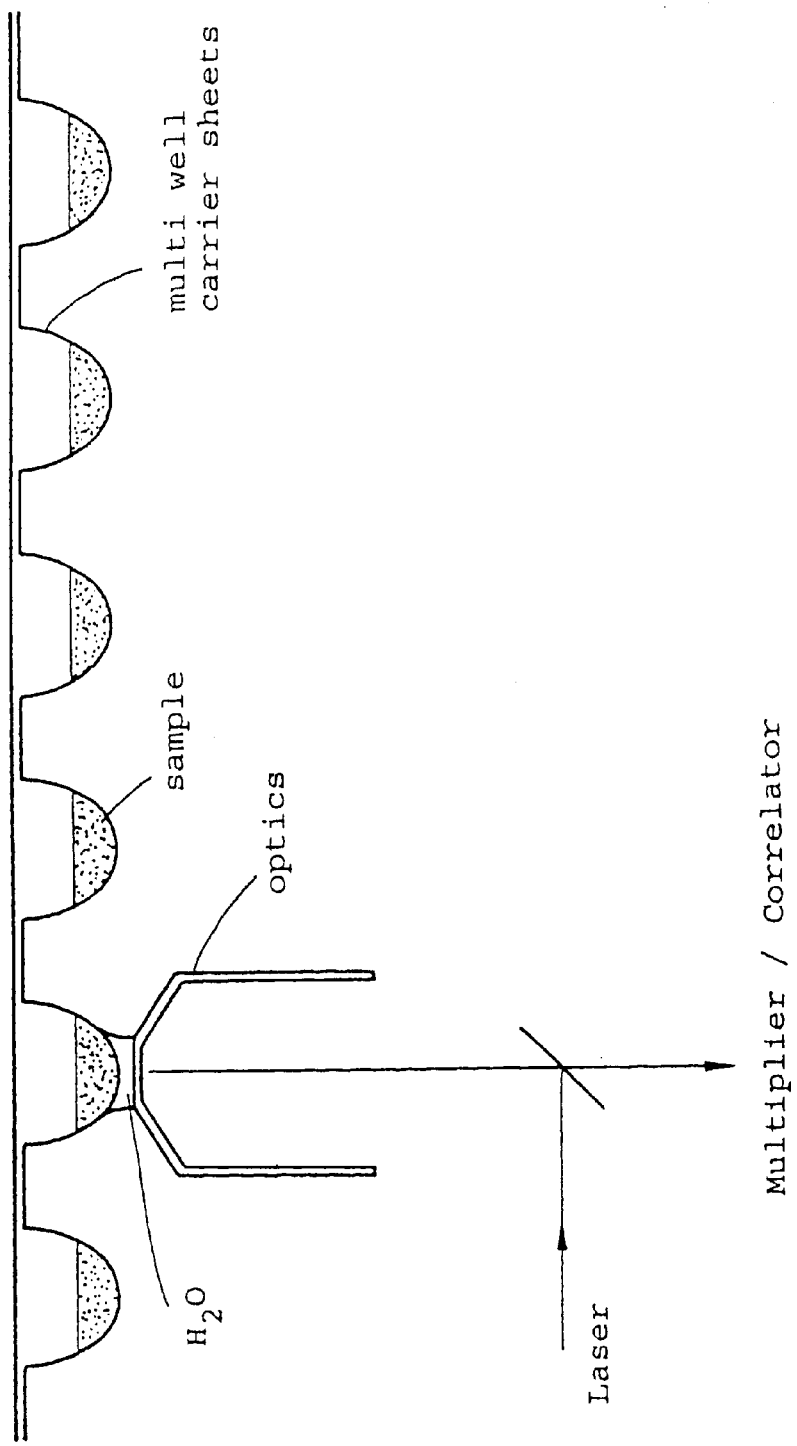
FIGS. 3 and 4 are schematic representations of FCS analyses using multi-well sheets.

From the below explanations, it becomes evident that several parameters have positive effects in the sense desired according to the invention at the same time in realizing small volume elements and, through a cumulative effect, have resulted, according to the invention, in the non-linear/exponential improvement of the methodology which has made the solution of the problem according to the invention at all possible.

A signal-to-noise ratio of 1000 necessary for the measurement of single molecules is attained by small volume elements in the fl- and sub-fl-regions. The deterioration of this ratio follows the third power of the increased radius of the measuring volume ($r^3$). This behaviour was completely neglected in earlier experimental approaches in which a laser beam illuminated the volume of a long column and virtually only diffusion in two dimensions out of the beam was analyzed.

If a larger volume is nevertheless to be analyzed for reasons of measurement technique, then many small volume elements according to the invention can be measured in parallel by multiarray detection and/or different small space elements with distinct space coordinates can be measured in succession. The characteristics of the signal-to-noise ratio is maintained therein for each Gaussian space element as measuring volume. According to the invention, each and every space element is preferably illuminated confocally with prefocused exciting light as in a single measurement of one space element and an image of the space element is formed in the object plane by a pinhole aperture.

The methodological breakthrough of the technology to the safe identification and measurement of single molecules and the possibility of counting single molecules which is necessary for determining equilibrium constants through the number of complexed and free ligands in the measuring volume over a particular measuring period was accomplished by using measuring volumes of $\leq 10^{-14}$ l. This has become possible by employing, according to the invention, pinhole apertures with diameters $\leq 100$ $\mu$m, preferably with diameters $\leq 20$ to 30 $\mu$m, as well as by employing a prefocused laser excitation. With pinhole apertures of this dimension located in the object plane, a diameter of the Gaussian measuring volume of 0.33 $\mu$m to 0.5 $\mu$m can be reached at 60-fold magnification. If optics with a different image scale are employed, correspondingly adapted pinhole apertures must be used. For free rhodamine, this means an average time for the diffusion out of the measuring volume of about 40 $\mu$s, whereas according to the prior art 750 $\mu$s are realized. At the same time it must be said, however, that a reduction of the radius of the Gaussian measuring volume by a factor>10 is not appropriate since the more than 1000 times smaller dwelling probability of a molecule in the measuring volume which is reduced by more than 1000-fold would lead to unacceptably long measuring times. Thus, the optimum of the presented method according to the invention corresponds to realized measuring volumes V of from $10^{-14}$ to $\geq 10^{-17}$ l. Anyway, with visible light the reduced size of the space element cannot be further reduced largely due to the diffraction properties of the light. This could be circumvented, however, by using X-ray radiation according to the invention in case nuclear fluorescences are excited in order to generate measuring signals.

Under the aspects,
that the measuring times be within a range (ms to sec) acceptable for practical applications,
that the signal-to-noise ratio be significantly>1 and especially within the range of 100 to 1,000, and
that the average times of diffusion of smaller molecules, molecular complexes, or molecular fragments (through the measuring volume) do not become too large, lest they be destroyed by exposition to the radiation designated for excitation,
an optimum Gaussian measuring volume of $\leq 10^{-14}$ l and especially $\leq 10^{-17}$ l results.

The signal-to-noise ratio's being quite high is accounted for, in addition to the fact that the measuring volume is small, preferably by appropriate filters being employed. For convenience, these optical filters are interference band filters to suppress Raman scattered light and/or Raman cut-off filters which "cut off" scattered light closely by the wavelength of the radiation designated for excitation, with optical densities of $10^{-7}$ corresponding to a suppression factor of $10^7$.

For the method according to the invention and the device for fluorescence spectroscopy of single molecules, molecular complexes and/or molecular fragments according to the invention, it is critical—in addition to the extremely sharp focusing of the radiation designated for excitation—that there be a confocally located pinhole aperture having an extremely small orifice in the beam path of the radiation resulting from excitation. The size of the orifice of the pinhole aperture in the object plane is selected depending on the image scale and the size of the measuring volume to be imaged in the object plane. With an image scale of 40 (100) and a radius of the measuring volume of $\leq 0.1$ $\mu$m, a radius of the pinhole aperture of 4 $\mu$m (10 $\mu$m) will result as a lower limit.

Background Scattered Radiation, Especially Raman Radiation

The more intense the exciting laser beam passing through the sample and the larger the volume element imaged on the single photon detector, the less intense is the radiation scattered by molecules and solids present in the sample that will reach the detector, that is to say it is more easily discriminated from the sought signal by autocorrelation.

According to the invention, a single rhodamine molecule is measured with a signal-to-noise, ratio of 1000 in a space element of 0.2 fl, if the Raman band of water is suppressed by conventional filters. Prior measurements without using such small space elements could realize signal-to-noise ratios of only $10^{-3}$.

Life of Fluorescence Dyes Under Light Exposure

The fluorescence dyes which are biologically applicable according to the invention have only a limited life. Dyes such as fluorescein are even significantly more light sensitive. For the precise measurement of average dwelling times, especially of large complexes, however, the dye will be excited about 10,000 to 1,000,000 times before the molecule will have left the measuring volume again. Each premature bleaching deteriorates the measuring result since premature bleaching simulates too large a translational coefficient (a smaller molecule).

Diffusion Times of Macromolecular Complexes, Viruses, Cells—Short Measuring Times Particularly large molecular complexes, viruses or cells have extremely small translational diffusion coefficients. In the small volumes according to the invention, viruses and cells can even be handled without significant bleaching of coupled dye labels which have diffusion coefficients of about $10^{-8}$ cm$^2$/s for free M13 DNA and about $5 \times 10^{-9}$ cm$^2$/s for an *E. coli* bacterium. The dwelling time of a bacterium in the measuring volume is about 30 ms. Larger measuring volumes, which have been the only possible ones this far, will result in unacceptably long measuring times until those large complexes will have left the measuring element again through translational diffusion.

Integrity/preservation of the Complexes not Present in the Volume Element

A statistical probability exists, that a dye will react out of the excited state by some chemical reaction and hence bleach. If this happens through light from outside the measuring volume, then the measurement should not be affected since an inactivated dye will not provide any signal at all and hence would not contribute to the measurement. However, the quality of the method is drastically limited by the fact that the effective concentration of measurable molecules and molecular complexes is decreased by premature bleaching of dye-labeled molecules which are still outside the measuring volume and hence the sensitivity is affected. Those negative effects will become quite bothersome if the laser beam is not focused to a maximum extent and if the label molecule is provided with several dye molecules according to a preferred embodiment of the invention, an undeterminable portion of which has already been bleached by prior light exposure.

Life of Complexes During Measurement

A complex of a target molecule to be detected and a labeled test reagent is detectable according to the invention only in the case that the complex remains stable throughout the measuring time. This would not be the case anymore with average complex dwelling times in large volume elements in the range of seconds, if the complexes themselves had a decay time in the range of seconds. This can thoroughly be the case with biologically relevant reactions such as metal ion complexations in which binding constants of $10^6$ l·mol$^{-1}$, for example, are relevant. The small volume elements according to the invention, however, mean so short average dwelling times (<1 ms) that for virtually all interesting complexation reactions a complex will remain stable throughout its dwelling time in the measuring volume.

Multiarray Detection

A multiarray detection according to the invention can be performed by a larger volume being illuminated in a non-optimal way with different volume elements being imaged separately on a multiarray detector, however, and the incoming photons being recorded and evaluated separately during a measurement. This is possible by using multiarray single photon detectors as commercially available. One drawback of this method is the fact that undesired irradiation will result in significant photoinactivation outside the measuring volumes. In a multiarray detection, that is in the parallel FCS analysis of measuring volumes of different space coordinates or in successive FCS analyses of measuring volumes of different space coordinates, it is not advantageous, in the sense of what has just been said, that a relatively large volume element be illuminated in an experimental array while the measurement of the small space elements is performed by simultaneous imaging, measuring and evaluating small space elements arranged in a 2D pattern. In this experimental proceeding (FIG. 24), numerous chromophores will bleach already before having reached the measuring volume by diffusion.

With lower concentrations, accordingly more volume elements will have to be measured. Since the average measuring time for one measurement ranges between 10 and 100 ms depending on the required quality of measured data (signal-to-noise ratio), from 10,000 to 100,000 volume elements can be tested in 1000 s. Hence, extremely low concentrations of $10^{-14}$ to $10^{-15}$ M can be measured. This also means that specific biological interactions with binding constants $k_{ass} \geq 10^6$ mol/l up to $k_{ass} = 10^{15}$ mol/l can be measured.

One example demonstrates how binding constants or reaction rate constants may be measured using the technique according to the invention. The measurement of a binding equilibrium between reactants according to the invention is based on the fact that at least one reactant is preferably chemically coupled to at least one dye molecule and the rotational diffusion rate and/or the translational diffusion rate of the reactant will change during complex formation. If equilibrium constants are not directly compatible with the experimental condition of highly diluted solutions, that is to say, if low binding constants require higher reactant concentrations, this can be achieved, for example, by offering an excess of the non-labeled reactant or by adding an excess of unlabeled reactant to the labeled compound.

The measurement of reaction kinetics through molecular fluctuation using FCS, as has been described by Magne, could not be carried out satisfactorily in the measuring compartments realized this far due to the long diffusion paths. With the measuring technique according to the invention, the determination of the dissociation rate constant of a complex is possible in a range of from $10^{-6}$ s$^{-1}$ up to about $10^3$ s$^{-1}$, which range is particularly relevant for biochemical reactions. Such measurement can be performed, for instance, by interchange of fluorescence labeled label molecules.

The technique according to the invention also allows for the measurement of conformational changes in biological macromolecules as well as the determination of related thermodynamic and kinetic constants. Fluctuations of the structure can be detected, for instance, through measurement of rotational diffusion or through signal changes by so-called energy transfer (Förster transfer).

This method is applicable in DNA/RNA analysis as well (DNA/RNA analysis, see below). In genetic analysis, particularly for the determination of infective pathogens, the sensitivity of the diagnostic method is often critical. This has become evident especially in recent years in connection with the introduction of enzyme-based methods for the amplification of genetic target sequences. It can be expected that by employing this method the necessity of a preliminary enzyme-based amplification can be avoided for several diagnostic methods, whereby problems of contamination with strongly amplified single sequences can be circumvented, for example.

The method can also be used instead of the known diagnostic methods of RIA, ELISA or other methods (see below, receptor screening). One particular advantage of the method according to the invention may be seen in the fact that the system is self-calibrating. Establishments of calibration curves or internal standardization need not to be done. Each experiment obtains its internal calibration from the determination of the molecules considered. For instance, variations of laser intensity will not affect the accuracy of measurement. A problem of drifting with successive measurements does not emerge. Measurements can be repeated at different times without renewed calibration yielding the same results. Calibration of the devices can be omitted.

One preferred application are assays without participation of antibodies as test reagents or for substitution in conventional assay methods which have been based on ELISA, RIA or FIA using antibodies. Considered are all assays employing other molecules in addition to antibodies as specifically recognizing molecules (receptor molecules, test reagents) in order to recognize particular target molecules (ligands). In general, possible receptor molecules, in addition to antibodies, are all molecules or molecular complexes which have specific recognition sites on their surfaces (e.g. antibodies, single-strand antibodies, membrane receptors, soluble receptors, enzymes, structural proteins, polysaccharides, peptides, complex-secondarymetabolites, etc.) or contain specific recognition sites for target molecules inside (e.g. HDL, VLDL, LDL).

If the formation of a specific complex between a receptor and one or more ligands in the general form is of analytical interest and/or if at least one of the involved molecules can be provided with at least one dye label and the complex formation becomes evident through change of rotational diffusion and/or translational diffusion of the dye label, then an FCS assay can be performed. Similar thermodynamic regularities with respect to an advantageous embodiment will apply thereto as apply to the corresponding assays of the ELISA, EIA, RIA or FIA types (see FIGS. 1, 2).

The performance of the method according to the invention becomes evident in particular when compared to technologies presently being in the market. A well introduced method is the so-called FPIA technology of ABBOTT, Chicago, using the so-called TDX system for the related instruments. Here, the depolarization of fluorescence labeled molecules is determined in homogeneous assays.

Depolarization of the emitted light of a fluorescence dye following excitation with polarized light is a property, which primarily depends on the molecular weight of the molecule an its shape parameters. A relatively small molecule will rotate more frequently within the period between excitation and emission of the fluorescent light than a significantly larger molecule would which results in a correspondingly stronger depolarization of the emitted light. This effect is made use of as small fluorescence labeled molecules compete with unlabeled target molecules for e.g. antibody binding sites. Fluorescence depolarization will then provide information about the relative portion of the labeled molecules bound in the complex. However, this method evidently does not reach the desired detection limits. The manufacturer herself gives a lower detection sensitivity of $10^{-9}$ M. The method according to the invention is more sensitive than this by more than two orders of magnitude even without optimization. This is true when the FPIA kits are used according to the invention. By using more sensitive dyes, additional orders of magnitude of increased sensitivity may still be attained. This is very important e.g. in drug diagnostics.

The method according to the invention exhibits its superiority particularly in a quantified assay and in quality depending on varying sample conditions. The degree of fluorescence depolarization depends on the conditions viscosity/temperature of the medium. With increasing viscosity, the degree of fluorescence depolarization of all molecules decreases due to lower rotational diffusion coefficients and immediately affects the results. Similarly interfering effects can be caused conditions of the medium affecting the life of,the excited state. Prolonged life will simulate an increased fluorescence depolarization. In the method of measuring the translational diffusion according to the invention, however, those effects do not adversely affect the quality of the results. In practice, this means a significantly smaller expenditure in sample preparation and scaling of the method and a notably larger range of dynamic measuring width.

2. The Significance of Reaction Rate for Complex Formation

As in the case of nucleic acid reassociation (see below), with other specific recognition reactions the association rate can also be so slow that a homogeneous assay based on this recognition reaction is not practicable. Whereas in inhomogeneous assays reactants are often offered in excess, for instance when working with labeled antibodies, in order to increase the reaction rate of the specific complex formation and the excess of reactants not bound to the complex is removed in a subsequent step, this cannot easily be done in homogeneous assays.

This problem shall be illustrated by means of an example: The detection according to the invention allows for the determination of concentrations of compounds labeled with fluorescent dye in the range of $\leq 10^{-15}$ M. If a fluorescence labeled specific test reagent is employed for a target molecule or a molecular complex, at least three requirements must be met: 1. The difference in size between the fluorescence labeled molecule not bound to the complex and bound fluorescence labeled molecule must be larger by a factor of about 2 in terms of diffusion constant in order to be readily detectable through the different translational diffusions; 2. the binding constant must be sufficiently large to complex the target molecule, 3. the reaction rate of the association must be sufficiently large to realize complex formation within an experimentally acceptable period of time ranging from minutes up to hours at most.

If one complexed target molecule among 100 molecules of the test reagent not bound to the complex can be detected, then according to the invention a concentration of $10^{-13}$ M of test reagent can be employed to detect a formed complex of $10^{-15}$ M. In the equilibrium, complex formation can take place efficiently, if the corresponding association constant $k_{ass}$ for the bimolecular reaction is at least $10^{13}$ $M^{-1}$. Such high binding constants will occur only rarely with biological molecules such as proteins.

The binding constants of antibodies usually are in the range of $10^6$ to $10^{10}$ $M^{-1}$.

The reaction rate constants of antibodies for the bimolecular complexation reaction hardly exceed the range of $k_{ass}=10^7$ $M^{-1}s^{-1}$. The difference in the binding constants principally results from the differences in dissociation rate constants $k_{diss}$ of the complexes which often range between 10 and $10^{-3}$ $s^{-1}$. For the case discussed above, however, a rate constant of $K_{ass}=10^7$ $Mol^{-1}s^{-1}$ means that the half life of association would be around 1000 s already if concentrations of $10^{-10}$ M of test reagent were employed.

According to the invention, several alternatives arise to make use of the sensitivity of the optical detection reaction, being $10^{-15}$ M for a homogeneous assay, for the recognition reaction despite of lower binding constants.

The effective association rate can often be changed dramatically by alteration of the reaction conditions. For nucleic acids it is described below how the association of complementary nucleic acid sequences can be accelerated by 10,000 to 100,000 times. Recognition reactions of sequence motifs on long-stranded DNA proceed faster than could be achieved by pure diffusion control. Probably, the rate-determining step is the arrival of the protein factor at the DNA followed by a fast one-dimensional diffusion step along the DNA to the actual site of binding.

An acceleration can in general be achieved by shortening the diffusion pathways of the rate-determining step of association. This is done, in a rather trivial way, by concentrating the reaction mixture.

According to the invention, the conditions of the medium are varied in the homogeneous assay such that the effective dwelling space of the reacting molecules is reduced without reducing the sample volume as such. According to the invention, this can be done, for instance, by additives such as poly(ethylene glycol)s, dextrane, polyvinylpyrrolidon, chaotropic reagents, organic solvents or combinations thereof which primarily affect the structure of the hydrate water coats. According to the invention, aqueous two-phase systems may also be used to enrich the reactants selectively in one of the phases.

Another possibility is the use of excess components of the labeled reactant. If two dye-labeled reactants are used, which can recognize and bind one analyte jointly, so-called energy transfer complexes can be formed. One dye label serves as an acceptor of the exciting light whose emitted fluorescence light will excite the closely neighboring second dye molecule (10–100 Å) which will then emit light detected as the measuring signal according to the invention. Because the efficiency of energy transfer decreases with the sixth power of the dyes' distance, the reactants can be used in excess. The translational diffusion coefficient of the ternary complex is measured according to the invention.

The use of the dye-labeled test reagent as an excess component is also possible according to the invention, if the uncomplexed test reagent can be modified chemically or by irradiation with respect to its spectroscopic properties such that it becomes spectroscopically distinct from the complex. This is possible, for instance, in the case of intercalating dyes.

The concentration by means of an electric trap according to the invention is described somewhere else in the specification.

If complex formation only weakly contributes to a change in molecular weight and/or shape of a test reagent, such as, for instance, in the use of a labeled antibody against a small ligand, then the use of a second antibody in excess which is directed against the complex according to the invention can render the produced ternary complex detectable according to the invention.

According to the invention, at least two different test reagents with at least two different dye labels, which are able to react with at least one target molecule wherein the fluorescence signals of at least two dyes are measured according to the invention, can also be used. This method can be employed in two ways.

a) Parallel Determination of at Least Two Different Analytes in a Sample.

The experimental problem frequently arises to detect several analytes together in one sample. Instead of two independant assays, detection of at least two different analytes can also be performed independently according to the invention by reaction of two independant test reagents which are labeled with at least two independant and different dyes and preferably can either be excited with light of different wavelengths or independantly detected by light of different emitted wavelengths. This can be achieved, for example, by using two independant optical systems such as those schematically outlined e.g. in FIG. 16.

3. Cross Correlation b) Increasing Detection Specificity by Simultaneous Binding of at Least Two Test Reagents to one Analyte.

Some analytes can be differentiated only with unsatisfying specificity from similar analyte molecules by binding one test reagent. These may be exemplified by homologous nucleic acid sequences which can be dramatically different with respect to their biological activities, such as e.g. their own pathogenicity or the pathogenicity of their products. Proteins, such as tumor antigens, structural proteins, or cell-type specific surface markers, can also be analyzed but unsatisfactorily by binding just one ligand.

According to the invention, a particular molecule can be complexed simultaneously with at least two test reagents which are labeled each with at least two optically distinctive fluorescent molecules. According to the invention, the simultaneous complex formation can be detected either specifically through formation of an energy transfer complex (Förster transfer, see above) or through correlation of the signals of excitation and/or emission having different wavelengths. Binding of different test reagents to one analyte is proven by, time correlation of the distinct optical signals.

The double complexing of an analyte with two differently labeled test reagents not only has the advantage of increased specificity, as discussed above, but also the practical advantage that higher concentrations of each individual reagent can be used. By means of time cross correlation of the fluorescence signals detected according to the invention, the signals of the uncorrelated free test reagents can be efficiently suppressed at the level of electronic signal processing. This method can be used especially well with nucleic acid analytes by employing at least two differently labeled test reagents which will bind to different sequence segments of the analyte. The emitted wavelengths of the respective fluorescences of the different dyes are distinct. Instead of the sole autocorrelation of the detected signals, which is otherwise usually measured, cross correlation of the signals of different wavelengths is measured according to the invention. If both probes are simultaneously bound to the target analyte, then cross correlation will yield the number of molecules and the diffusion time of the doubly labeled nucleic acid segment. Probe molecules which are not bound are visible in autocorrelation, whereas their signals are suppressed in cross correlation.

4. Method and Device for Performing Fluorescence Correlation Microscopy

Thus, cross correlation of fluorescence signals of different dyes chemically linked or physically associated with a molecule or molecular complex can be used to increase sensitivity and enhance specificity according to the invention. To perform the experiments in an optimum way, however, several requirements must be met which can be achieved to particular advantage by the method according to the invention presented herein in the following as well as by a related device.

The method according to the invention pertains to the combination of the method of cross correlation with fluorescence correlation spectroscopy using small measuring volume elements. This method must be clearly differentiated from such correlation methods as employed e.g. in FACS analysis (fluorescence activated cell sorting). Several optical parameters derived from a large complex such as a cell are also measured simultaneously therein, e.g. the forward light scattering in combination with a fluorescence signal or the simultaneous measurement of distinct fluorescence signals. In the cell sorter, the signals of single droplets are measured in which single cells may be present. Therein, by correlation of signals to identify cell types and subtypes is only meant the intensity distribution of different signals which is detected integrally throughout the droplet. Correlation is considered therein only to mean the parallel detection of several parameters with respect to their individual intensity. The method described herein time-links two stochastic processes, the diffusion characteristics of different chromophores in a small space element. On the level of a cell, this means virtually that the method according to the invention is able to distinguish between different molecules bearing a chromophore and being present in the measuring volume whereas in the cell sorter, the concentration of this chromophore is determined integrally in the droplet, irrespective of whether it is part of a small molecule or it occurs in a complex or bound to a cell.

Cross correlation in connection with FCS analysis is intended to mean the following methodology: A volume element is illuminated by a laser beam or X-ray beam which is as strongly focused as possible. The intensity of the electromagnetic radiation is chosen so high that a large percentage of molecules that can be excited by the radiation exist in the excited state. The fluorescent light emitted by them is detected by confocal imaging by means of a pinhole aperture in a single photon measuring device so that only a small volume element of the elongated cone of light is measured. When a molecule migrates into said volume element by diffusion, it is excited and measured through the emitted light as long as it remains inside this measuring volume element. The average dwelling time is characteristic for the size and shape of a molecule, a molecular complex, or a cell.

In this way, molecules being present at different concentrations can be distinguished or simultaneously counted by correlation spectroscopy. For instance, binding constants for complex formations of e.g. receptor/ligand interactions or kinetic constants such as decay rates of such complexes can be determined in this way. The method will yield optimum results if particularly few molecules with fluorescent properties are present in the volume element per unit of time. This is the case for concentrations in the range of $10^{-9}$ and below. Conversely, however, the problem arises that complex formation with a second reactant will not proceed any faster than by $10^7$/s. For equimolar concentrations for two reactants of $10^{-9}$ M, this means a reaction time of more than one minute. Shortening of the reaction time can be achieved, for instance, by using an excess of the fluorescence labeled reactant. With a reactant concentration of $10^{-9}$ M, complexes with target molecules with a concentration of $10^{-12}$ M can be detected in this way after minutes of reaction time. With lower concentrations, the signal-to-signal ratios of complex and free ligand become too high to allow for reliable concentration measurements. Another experimental problem arises if the binding constant of a complex to be measured is not high enough to employ ligand concentrations of $\leq 10^{-9}$. Virus antigens, nucleic acids of pathogens, or certain hormones, however, have to be detected in concentrations which are significantly smaller than $10^{-9}$ M. A typical application field is the diagnostics of tumor antigens through monoclonal antibodies which often have a low binding constant as well as not too high a specificity in distinguishing the tumor antigens of a dedifferentiated cell from the antigens of the respective differentiated cell. Cross correlation using two different chromophores allows to increase sensitivity and specificity in the sense discussed above.

At least three chromophore bearing molecules or molecular complexes need to be distinguished experimentally: free ligand with chromophore 1, free ligand with chromophore 2, complex with chromophore 1, complex with chromophore 2, and complex with chromophore 1 and chromophore 2. Only a complex bearing both chromophore 1 and chromophore 2 throughout the period during which the complex is present within the measuring volume is indicative of a target molecule to be detected such as a tumor antigen or a pathogen, such as a virus, or a related DNA or RNA.

Now, in cross correlation the signals of chromophore 1 and chromophore 2 are correlated. Only in the case that a molecular complex is excited in which in one and the same window of time, wherein the molecular complex is present within the measuring volume, both types of chromophore are detected, these signals are assigned to a complex bearing both chromophores.

Critical requirements for a successful cross correlation are:

The distance between chromophores 1 and 2 on the target molecule must be small compared with the dimensions of the measuring volume, so that both dyes are hit by the exciting light simultaneously within the error limits of the measurement, when they enter the measuring volume and leave it again (distance in the complex<0.1 $\mu$m).

The measuring volume must have the same dimensions for both dyes, so that both dyes, when linked to one another, are in contact with the respective exciting light within an identical window of time.

Both measuring volumes must have the same space coordinates within the error limits of measurement.

Solving this problem is in no way trivial. For instance, one problem is the fact that light of different wavelengths will result in different image sizes due to different refractive indices, as is well known. It would be disastrous to the measurement, however, if two lasers with different wavelengths illuminated unequally sized volume elements due to unequal focusing, or if detecting on the photo multiplier covered different measuring volumes.

According to the invention, this problem is solved either by using only one laser with one exciting wavelength in connection with the use of two dyes with strongly overlapping exciting spectra which can be distinguished, however, by the so-called Stoke shifts of at least two emitted wavelengths. Alternatively, volume elements having identical space coordinates are illuminated by two independant laser light sources. For convenience, the optics of confocal imaging is color compensated in both cases, i.e. corrected for both emitted wavelengths, so that one and the same space element is measured for both wavelengths.

According to the invention, imaging optics which is conventional in microscopy is used for imaging the fluorescent light of different wavelengths which will image light of different wavelengths with identical scaling. For the performance of the method according to the invention it is also critical, however, that space elements of identical size, identical intensity profile, and identical space coordinates be illuminated for both wavelengths. This is achieved by using, according to the invention, a device on the side of excitation optics in which both laser beams are prefocused before entering the sample wherein either two fixedly adjusted optics having different magnification values are employed so that, as a result, both wavelengths are prefocused with the same dimensions and geometry of the beam, or else a device with fixedly adjusted prefocusing optics is used, that is in combination with a variable beam expander for the second beam path or by employing variably adjustable beam expanders for prefocusing in both beam paths.

For convenience, the device is realized as a compact double microscope whose two objective lens arrays, oriented to two opposing sides of the measuring compartment to be illuminated, can be shifted along their optical axes. The optics for the incident light beams and for the light beams emitted by the molecules, molecular complexes, vesicles, or cells of the measuring compartment are arranged on two sides of a common guiding or supporting device for each "moiety" of the double microscope. Each of the incoming light beams are deflected towards the objective lenses by dichroic mirrors. The returning light beams penetrate these dichroic mirrors rectilinearly to hit a detector after having passed diverse optical elements, such as lenses, confocal elements, and filter devices.

For convenience, the optical axis of the light beams impinging on the dichroic mirrors is oriented perpendicular to the shifting direction of the two objective lenses. The two light beams of different wavelengths, superimposed, impinge on mirrors located one behind the other, the first of which in the beam path is a dichroic mirror. One of the two light beams is deflected by this dichroic mirror whereas the other rectilinearly penetrates this dichroic mirror to be deflected by the reflecting mirror behind in the direction opposite to that of the first light beam. The deflection directions of both light beams are parallel to the shifting direction of the objective lenses. The deflected light beams are again deflected by reflecting or dichroic mirrors to pass through the optics for the incoming light beams. This arrangement of the optical elements of the double microscope has the advantage that the two objective lenses along with the optics for the light impinging on the measuring compartment and proceeding therefrom can be displaced without the need to displace or shift the light generation sources along with them. The light generation sources which are, in particular, laser sources, can be positioned remote from the double microscope; only the relative position between the light generation sources and the site of the double microscope where the two light beams are superimposed and fed in must not change.

The device can also be employed in the case when it is necessary to cover fluorescence signals from the measuring volume over the total $4\pi$ solid angle. In particular, this may be the case when it is critical to cover all emitted photons in the detection of one single molecule. In this case the device described would be used in such a way that only one exciting wavelength is employed and both detecting optics together cover the total $4\pi$ solid angle.

FIG. 1 illustrates a receptor assay for related effector molecules using receptor bearing cells wherein the receptors have specific binding properties as to a ligand L. The ligand is provided with a dye label according to the invention. According to the invention, the molar ratio and the total concentrations of receptors and ligand are selected to advantage such that about 50% of the receptors are occupied and about 50% of the ligands remain unbound. In the analysis according to the invention, this can be seen by the fact that about the same number of emitted light signals are detected from molecules with fast translational diffusion as are detected from molecules with slow translational diffusion (schematic drawing on the upper right; the step on the left corresponds to the free ligand, the step on the right corresponds to the receptor bound ligand).

When a potential active substance is added, a shift of the equilibrium indicates interaction of the candidate active substance with the specific receptor binding. In the case of an antagonistic activator or blocker of the receptor function, displacement of the labeled ligand will be observed (the signal only corresponds to that of the free ligand). The same signal can be obtained if an allosteric interaction of the active substance with the receptor or with the ligand prevents binding of the labeled ligand.

In an analogous way, a potential active substance can also enhance binding of a ligand to the receptor so that measurement of bound ligand will be increased (lower right).

The assay can also be performed in the case that the cell bears more receptors which do not interfere with the specific reaction observed.

If the equilibrium in a receptor recognition reaction is not quickly reached, it may be of advantage to make the labeled ligand and the potential active substance compete for the receptor simultaneously.

FIG. 2 describes the use of potentially different receptors on different cells which, however, will possibly recognize a defined natural ligand with the same specificity and binding strength, but will transmit different signals. Potential active substances could be of interest to selectively activate or block those receptors. This can be achieved with mutants/ variants of the natural active substance as well as with active substances which are not structurally related.

For instance, the assays for the respective target receptors are first performed separately. Here, the rules which are given in the legend of FIG. 1 will apply. A potential active substance is primarily assayed for interacting effectively and specifically with one of the studied receptor bindings and thus for allowing to separate different receptor functions (possible cases on the lower left). With effects acting in the same direction, measuring results such as shown on the lower right can be found.

As will be set forth in more detail below by means of specific examples, FCS assays according to the invention are especially prominent because they are not limited to antibody mediated specificity, are equally useful for molecular, cellular, tissular systems in homogeneous or in solid phase assays, allow for the determination of thermodynamic parameters (binding constants) and kinetic parameters (rate constants), allow for non-destructive investigations of living systems (cell cultures, tissue), and unspecific interactions with surfaces do not interfere when analysis takes place in solution.

5. Screening of Pharmacologically Active Substances Through Binding of Known Fluorescence Labeled Ligands to Unknown Receptors Which may be Present on Cells or on Natural or Artificial Vesicle Structures Natural as well as chemically synthesized pharmacologically active substances exist the target molecules of which are not known. Those target molecules may be extracellular molecules (e.g. protease inhibitors), surface membrane receptors (e.g. insulin), soluble mediator receptors (steroid hormone binding receptors), or cellular structural proteins, or enzymes.

Hence, according to the invention the extremely important problem can be solved to find, characterize and optionally to isolate the pharmacologically important target molecule of a known active substance:

search for orphan receptors revelation of the mechanisms of pharmacological action search for analogous active substances search for and distinction between different receptor molecules, preferably in distinguishable biological targets (different cell differentiation, tumor/non-tumor, pathological/non-pathological, etc.).

Pharmacokinetics

According to the invention, pharmacokinetic investigations may also be performed:

after different intervals of time following administration of a particular active substance, tissue samples or body fluids can be analyzed in competitive experiments using freshly added dye-labeled comparative substance.

Figure 19:
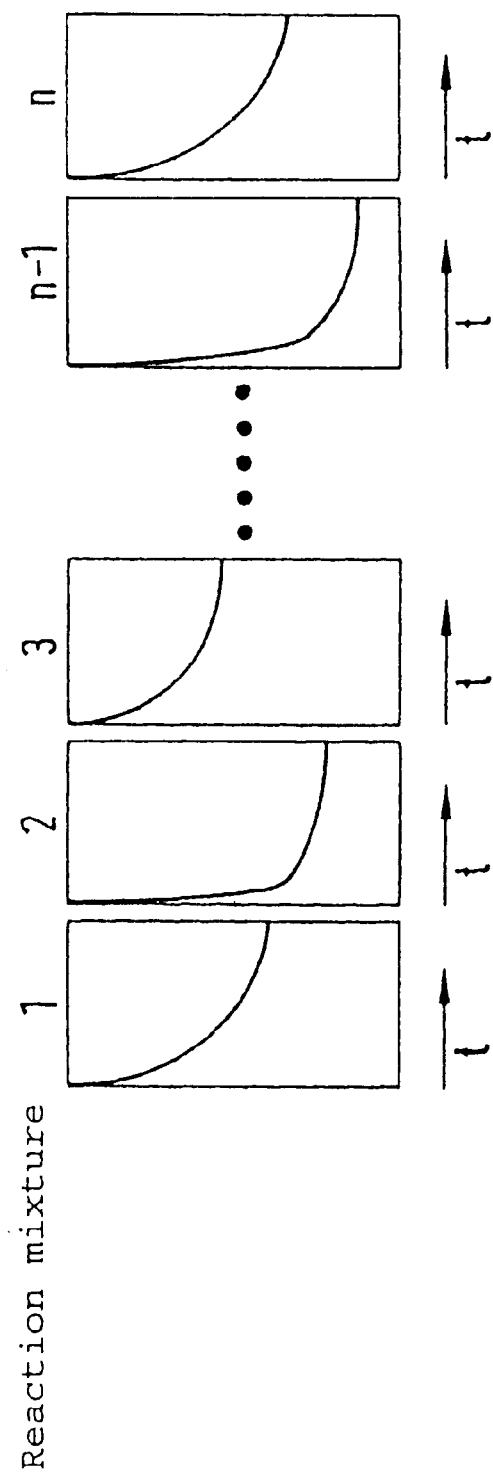
FIG. 19 is a flow chart illustrating FCS experiments performed in parallel.

Distinguishing Between Target Molecules of Active Substances Through the Dissociation Rate Constant of the Complex If an excess of dye-labeled active substance is added to a mixture of different complexes between receptors and the active substance, then nearly each dissociated molecule of the active substance will be replaced by dye-labeled active substance. Optionally, the experiment may be carried out with reverse labeling as well. For example, a typical problem is the analysis of different cell lines in order to detect distinct receptors (example: tumor surface antigens, protein P binding receptors type I, II, III). Typically, a diagram such as that depicted in FIG. 19 will be found, if many samples are analyzed simultaneously. According to the invention, large amounts of analyses are analyzed in an experiment simultaneously and/or repeatedly over a long period of time, when dissociation rate constants are slow, by analyzing the determination of the ratio of initially bound and dissociated active substance iteratively in all positions after fixed intervals. FIG. 19 contains a schematic drawing of the results.

In this way, different receptors or antigenic determinants may be assayed, for example, which form complexes of different thermodynamic stability with a specific target molecule in one and the same sample or in different samples with e.g. different cell types or differentiation stages, whose dissociation rates ($k_D$) are drastically different while their reaction rates values ($k_R$) are often comparable. Thus, biological guiding structures for so-called orphan drugs or orphan receptors or members of multifunctional molecular families can be detected by means of functional assays.

In practice, advantages in handling especially arise from the fact that working in homogeneous solution allows for very short incubation times for routine analyses in the nM range which are virtually no longer relevant (range of seconds to minutes), and there are no extensive washing steps or secondary incubations. As sample carriers, sheet-like carrier systems are preferably used which make it possible, according to the invention, to approach the liquid sample close to the objective without contact and hence without contaminations (FIG. 3).

FIG. 3 illustrates the use of carrier sheets having wells thereon such as described or used, for instance, in the patent applications PCT/EP 89/01320, PCT/EP 89/01387, PCT/DE 91/00082, PCT/DE 91/00081, PCT/DE 91/00083, PCT/DE 91/00704. The reaction carriers, referred to as multi-well sheets, bear wells which can receive the samples for FCS analysis according to the invention. They are controlled by a two-dimensionally positionable sheet insertion device such that the bottom of the sample containing well is approached closely to the objective, so that the liquid sample volume is not further away from the edge of the objective than about 100–1000 µm. $H_2O$ is the preferred medium between sheet and objective, to which the correction of the objective is preferably related (see above). The sheet is optically clear and chemically inert with respect to both the exciting light of the laser and the emitted light. In a preferred procedure, the sheets are sealed by a cover sheet. Sheets are preferred which have a distance between wells corresponding to the commercial microtitration format or Okasaki format, since automatic pipetting devices for those formats are available in the market in great numbers. Moreover, sheets as reaction carriers are low-polluting, easily disposed and can be filed space-savingly in the sealed state.

6. Analysis of Ionic Molecules

Charged molecules (cations and anions) can be analyzed specifically within the measuring compartment of the method according to the invention by employing an "electric trap". This can be done, for instance, by inducing a molecular flux through the measuring compartment wherein, with or without superimposing by a mechanically induced flux, an electric field causes concentration of particular ionic molecules in the observation compartment or a single molecule is transported into the compartment directedly. This can be achieved by a rectified field, e.g. between the outlet ends of two capillaries with a fiel strength in the range of about 1 V/1 µm. According to the invention, it can also be accomplished to make one or more trapped molecules oscillate in an alternating electrical field in the observation compartment as soon as they have entered this volume element (see below).

Technical Description of the Device According to the Invention

7. Optics

The method according to the invention can be performed technically with microscope optics of high quality with respect to the image quality of the focus. In particular, the lens system before the emergence of the exciting light must be chromatically and spherically corrected. Preferably the system Neofluar of the company Zeiss, Oberkochen, Germany having a high numerical aperture≧1.2 N.A. is used with or without cover glass or separating coat. The operating distance is 0.17–0.9 mm. The objective is corrected for water and offers maximum numerical aperture with maximum operation distance. Oil immersion objectives are less suitable. According to the invention, the light quantity is limited by a confocal pinhole aderture in the object plane behind the microscope objective.

8. Laser Light Source

As laser light sources for wavelengths of >200–1000 nm continuous lasers are preferably employed, especially lasers of the argon, krypton, helium-neon, helium-cadmium types as well as tunable diode lasers (red to infrared regions), each with the possibility of frequency doubling. According to the invention, the use of pulsed high frequency lasers of ≧10 MHz is also possible.

9. Laser Intensity

A laser intensity of 0.5 mW is already sufficiently high that a few percent of the dye molecules in the observation volume are excited. With a laser intensity of 5 mW, the percentage of excited molecules is already 50%. Thus, further increase of the laser power does not appear appropriate for increasing the light efficiency.

10. The Luminophore

Possible luminophores or fluorescent dyes apt to be coupled are a great number of fundamental dye structures as well as oligomers of those dyes as employed for a long time in fluorescence spectroscopic detecting methods. Preferred dyes are those which either do not themselves contribute to specific, interfering interactions with target molecules or are employed specifically making use of specific binding properties such as being capable of nucleic acid double-strand intercalation, as has been proposed in P 42 34 086.1 (Henco et al.).

Preferably, the dyes employed have an absorption coefficient between about 30,000 and 100,000 with a quantum yield of 0.1–1.

For example, dyes from the coumarin series, or rhodamine B derivatives with a high content of hydrophilic residues to prevent hydrophobic interactions, or dyes based on thiazole orange fundamental structures which are capable of intercalating in double-strands have proven to be suitable.

For the measuring method according to the invention, resistance of the dyes to photobleaching (bleaching stability) is an important property. However, as has been mentioned earlier, it is no longer of outstanding importance for the performance of the measurement since measuring times have shortened by some orders of magnitude as compared with measuring compartments which are about 1000 times larger when very small measuring volumes according to the invention are employed.

11. Significance of the Triplet State

According to the invention, dyes are preferred which do not tend to form triplet states.

When selecting dyes, it is of great importance to select those dyes which have a very low tendency to form triplet states. Each triplet state entered raises the probability of a chemical reaction, does not provide a signal or provides a signal with an undesired wavelength, and extends the period until the molecule is ready to be excited into the singlet state again.

If dye multimers are employed for labeling, particularly those based on hydrophilic dyes such as certain coumarin derivatives, then measuring time can be shortened significantly. The larger number of individual measuring values has the result that less events of molecular passage through the measuring element must be pursued to obtain sufficient measuring accuracy.

12. Measuring Compartments

Figure 4:
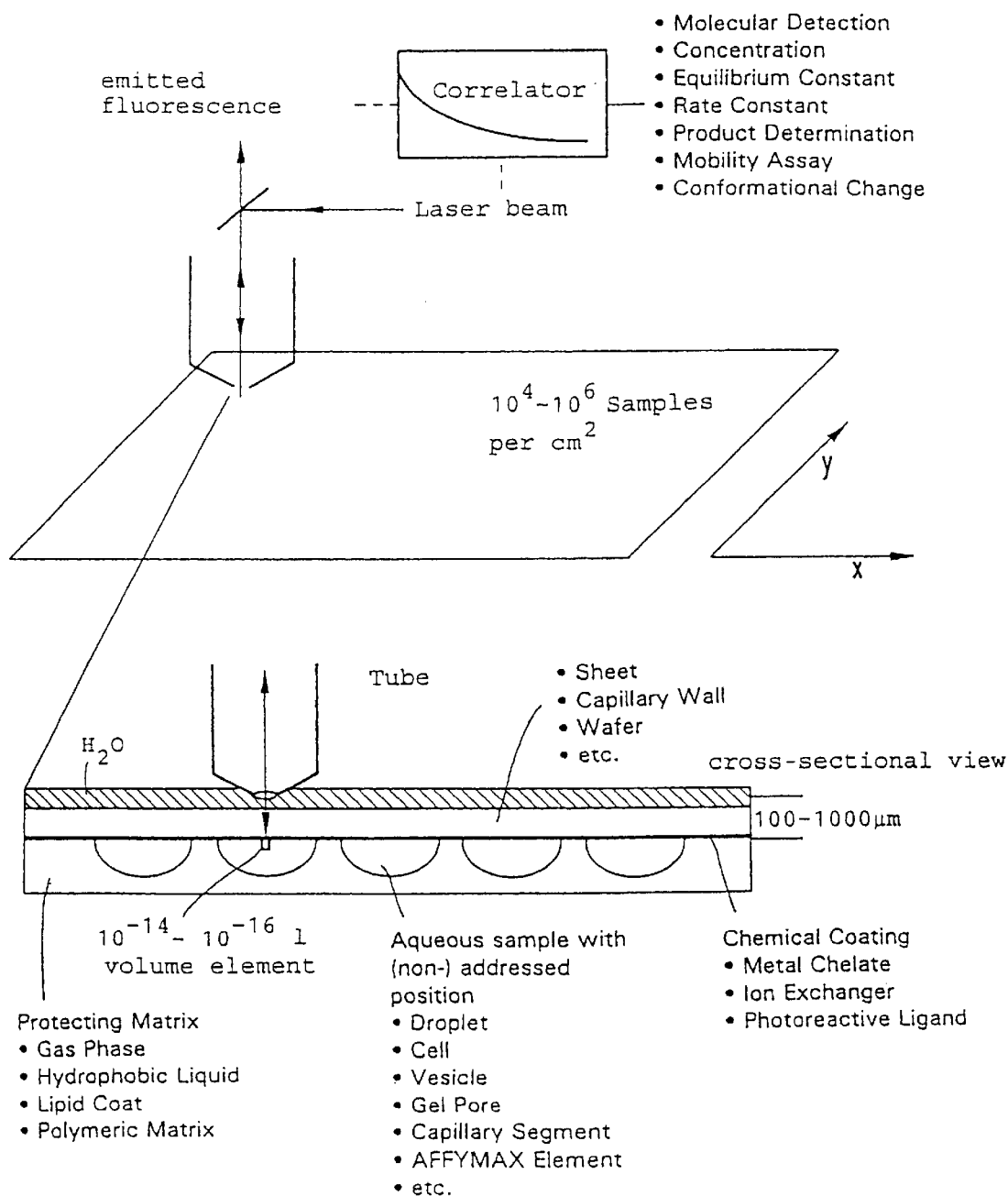

According to FIG. 4, the measuring compartments must be approached to the emergence objective of the laser-focusing optics at 100–1000 $\mu$m. In the simplest case, this is done by means of a drop hanging on the objective itself and containing the molecules to be analyzed. Such a measuring set-up can be used only for a few analyses since the risk of contamination between different samples is high. Techniques comparable to those of conventional microscopy with cover glass and oil immersion can be employed. The method according to the invention uses water immersion and very thin glass or plastics sheets to separate the aqueous sample from the optics. The sheets can at the same time serve to seal the compartments underneath in the form of flat carriers or in the form of capillaries.

For the application of screening large numbers of samples, as occur in experiments with evolutive optimization of biopolymers, membranes are also used which are chemically modified on the side directed to the sample. Preferred modifications are surface structures having specific binding properties, such as e.g. ion-exchange properties to fix nucleic acids, and/or specific binding properties with respect to proteins, such as antibody coating or coating with chelating agents, especially NTA (nitrilotriacetic acid) or IDA (iminodiacetic acid), to selectively fix recombinant proteins or peptides with binding oligopeptides, such as $(His)_6$, which can be bound to surfaces through metal chelates with high binding constants ($k_{ass} \geq 10^{10}$) in order to analyze them for their respective properties of interaction with target structures.

13. Molecular Trap

Another possibility for the described detection of single molecules in small volume elements is the use, according to the invention, of a molecular trap using an electric field, which shall be described later. This kind of analysis can be applied, however, only to molecules apt to interact with the electrical field, such as ionized molecules.

14. Detection

Detection of the measuring signals preferably takes place through the optics of a fluorescence microscope with single photon counting wherein an avalanche diode detector is preferably used. For instance, the use of SPC-100 and SPC-200 of the manufacturer EG & G has proven to be appropriate. Signal analysis is performed with a digital correlator or a multichannel counter MCS.

Method and Application

15. Characterization of Molecules

The correlation method directly reveals three characteristic molecular quantities: the number (N), the translational diffusion coefficient $D_t$, and the rotational diffusion coefficient $D_r$. The latter two are a function of molecular size and shape (i.e. radius, shape and volume) and provide information about changes of the molecule, e.g. by enzyme cleaving or complexation with other ligands, etc. Because measurement of diffusion correlated diffusion times can be performed quickly and with high sensitivity according to the invention, the method for analyzing molecular sizes and their distribution in a population in solution can be used without the need of chromatographic separation.

16. Determination of Binding Constants

As R. Rigler has shown, analysis of the correlation function for molecules reacting with one another has the result that the interaction can be determined my measuring the number of molecules N and the weighting factors of the characteristic diffusion times. In the case that the value of the reaction rate constant is slower than diffusion time, which always will be the case in specific reactions, the correlation function is given as the sum of the weighted diffusion times:

$$G(t)=1+1/N(x(1+t/\tau_x)^{-1}+y(1+t/\tau_y)^{-1})$$

where x, y, and $\tau_x$, $\tau_y$ are the proportions and diffusion times of molecules X and Y. $\tau=\omega^2/D$. $\omega$ is the radius of the sample volume and D is the diffusion constant.

In the case that reaction rate constants are faster than diffusion times, the correlation function becomes $$G(T)=1+1/N(1+4<D>t/\omega^2)^{-1}$$

where $<D>=xD_x+yD_y$.

If $D_x$ and $D_y$ are different, the binding of a (small) ligand to a large target molecule as the receptor (protein, nucleic acid, antibody) can be followed in a simple way without molecular separation processes that are usual in so-called inhomogeneous assays. Corresponding relationships can also be deduced for the rotational diffusion coefficients or rotational diffusion times. The high measuring sensitivity exceeds that of radioisotope methods as known from the radioimmunoassay techniques (RIA) These are equally good only when labeling with high specific radioactivity. When performed according to the invention, molecular separation processes and time-consuming calibration can be omitted. Hence, the correlation method represents an alternative to the radioimmunoassay used today. According to the technique described above, a fluorescence labeled antigen whose binding to an antibody is analyzed in competition with the antigen to be determined in homogeneous phase or inhomogeneous phase (solid phase coupled) is employed instead of the radiolabeled antigen reagent. One advantage of the method according to the invention is based on the fact that undesirable radioactivity can be omitted while at the same time increasing the sensitivity of the measuring method.

17. Products of Enzyme Reactions

Where enzyme catalysis results in a change of molecular structure and molecular weight, the formation of reaction products can be followed through the change of the number of molecules and of diffusion times. Typical applications are replication and cleavage of nucleic acids, cleavage of proteins and peptides, but also selection of catalytic antibodies.

18. Molecular Dynamics in Membranes and Cells

The possibility to measure the rotational diffusion of large molecules in viscous environment using the FCS method is of particular importance for the analysis of the dynamics of specific receptors on cell surfaces, but also inside the cell. At the same time, binding of labeled ligands can be measured by measuring rotational diffusion and translational diffusion at cellular structures, such as receptors etc. Examples are neurotransmitters, tissue factors, such as growth hormones, but also cationic ligands such as $Ca^{2+}$.

The method according to the invention can also be performed involving molecules that do not fluctuate or fluctuate very slowly. This is the case, for example, if measurement takes place in highly viscous media, in gel matrices or tissues, using solid phases or with very large molecular complexes or cells involved.

Figure 5:
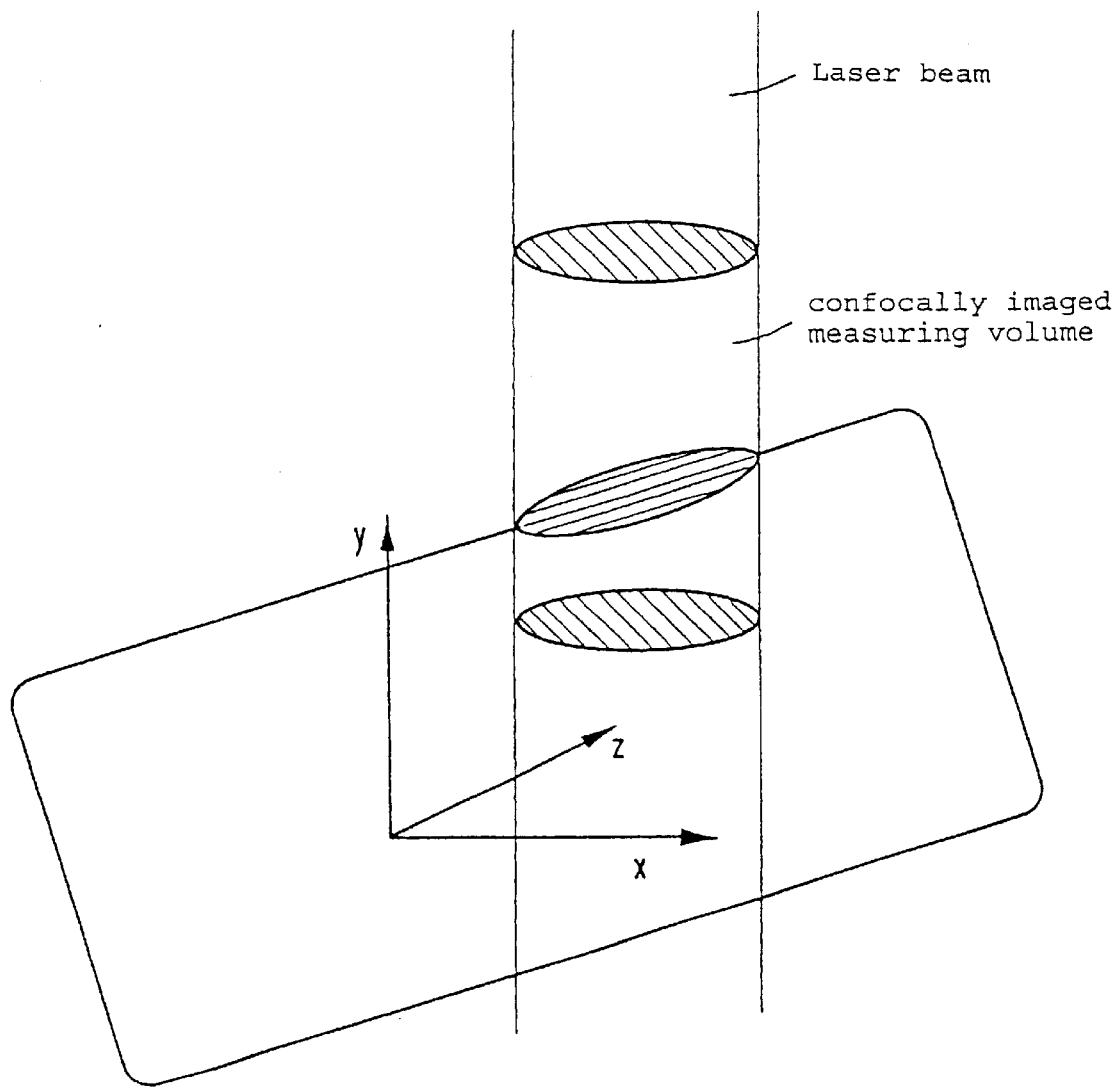
FIG. 5 is a schematic representation illustrating the measurement of molecules using FMS.

Surprisingly, even cells can be measured in aqueous suspension despite of their large masses. Brownian motion and turbulences are sufficiently high to move e.g. a membrane segment with its receptors into the measuring volume and out again without intervening bleaching phenomena of the dye labels occurring. Schematic FIG. 5 depicts the measurement of nearly stationary molecules according to the invention. As indicated by the rectangle, for instance, they may be present as membrane receptors on an immobilized cell (rectangle). The coordinate axes illustrate the analysis, according to the invention, of non-fluctuating molecules as well by forced relative motion of the measuring volume with respect to the stationary element. This can be done by a relative change of the laser coordinates, of the coordinates of the measuring volume, or of the coordinates of the sample volume, or of a combination thereof.

When fluctuation is strongly limited or the dye labels are bound in a stationary way, fluctuation with respect to the measuring volume must be forced according to the invention. This is achieved by forced motion of the sample volume and the measuring volume contained therein (e.g. vibration, flow) and/or continuous or discontinuous change of the positional coordinates of the measuring volume within the sample volume. This is preferably done by changing the focus and/or by changing the position of the illuminated volume element. In the special case of a fixed label molecule, the relative motion with respect to the positional coordinates of the measuring element thus forced exclusively determines the "apparent" translational diffusion of the bound dye. To achieve discrimination of dye molecules which are coupled to non-fixed molecules, the forced relative motion must be slower than that of the non-fixed molecules.

The procedure described according to the invention is possible in the case that the time of translational diffusion of the slowly diffusing complex is irrelevant for analysis and rather the absolute or relative number of the dye labels linked thereto is of interest. This is the case, for instance, in determining receptor binding constants on cell cultures or in tissues.

The method according to the invention allows for the measurement of molecular and/or cellular mobilities in an especially advantageous way. Such determinations are of great interest in technical, biological and medical terms and often are only possible by using specialized technical methods which have not become wide-spread. The following selected examples, according to the invention, may be mentioned: determination of spermatozoa mobilities for fertility determinations, mobility of macrophages, activity of contractile elements, mobility of membrane proteins in natural or artificial membranes, mobility of actively or passively transported molecules. Preferably, this is done by labeling the cells, molecular complexes or molecules of interest with specific dye-labeled ligands, such as labeled antibodies or antibody derivatives, or by direct labeling with a dye label.

One critical advantage of the procedure according to the invention is the possibility of screening pharmacologically active substances through binding of known fluorescence labeled ligands to receptors known per se which may be present on cells or natural or artificial vesicie structures. Presently, a preferred direction of research in searching for receptor binding active substances consists in cloning certain receptors, such as the family of protein kinase receptors, first and expressing them separately. Then, these target structures are immobilized individually, e.g. in ELISA plates, and analyzed using ELISA assays. To do this, a considerable amount of research and personnel is required to which the risk must be joined that a cloned and isolatedly expressed receptor changes or loses its functionality or specificity.

According to FIGS. 1, 2), it is possible in the case of the invention to completely omit cloning of receptors. Cells or fragments of natural cells or cloned cells can be employed since receptors must only be used in concentrations whose values are within the range of the reciprocal binding constant for the specific ligand interaction. This also suppresses the risk of unspecific interactions with other ligands or receptors that may occur with high reactant concentrations. Hence, the presence of other receptors does not interfere with the assay.

If different cells/cell lines are used in an assay with a single type of labeled ligand, differences in the functional behavior of the receptors may possibly also he distinguished through competition with mutants or variants of the binding ligand. A differentiated receptor function with respect to one and the same effector in different tissues appears to be a not unfrequent regulatory mechanism (e.g. TNF, kinines) (see FIG. 2). This effect can be used pharmacologically by employing selective ligand variants which recognize but one receptor type.

Figure 26A:
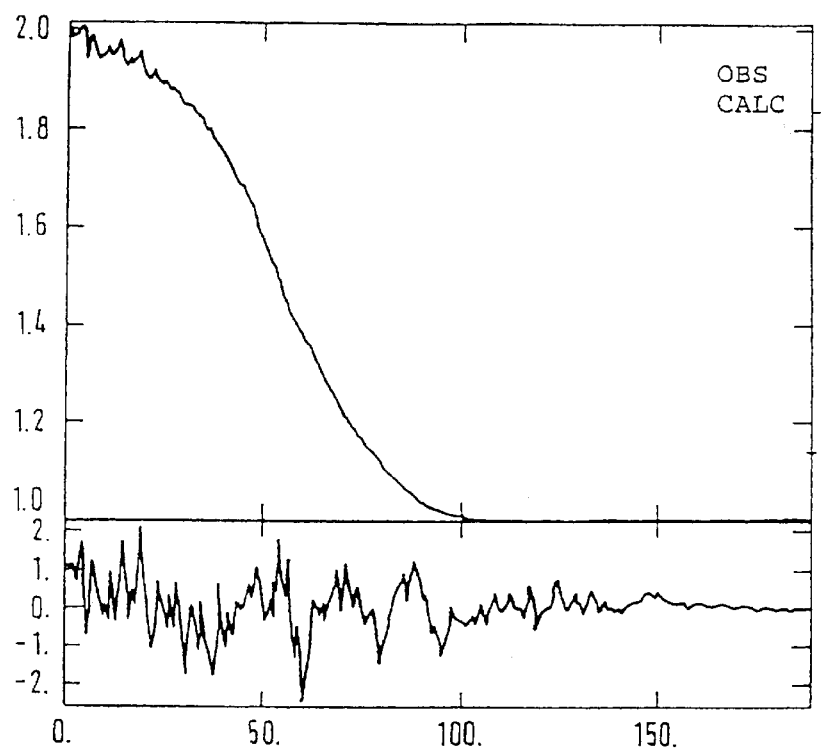
Figure 26B:
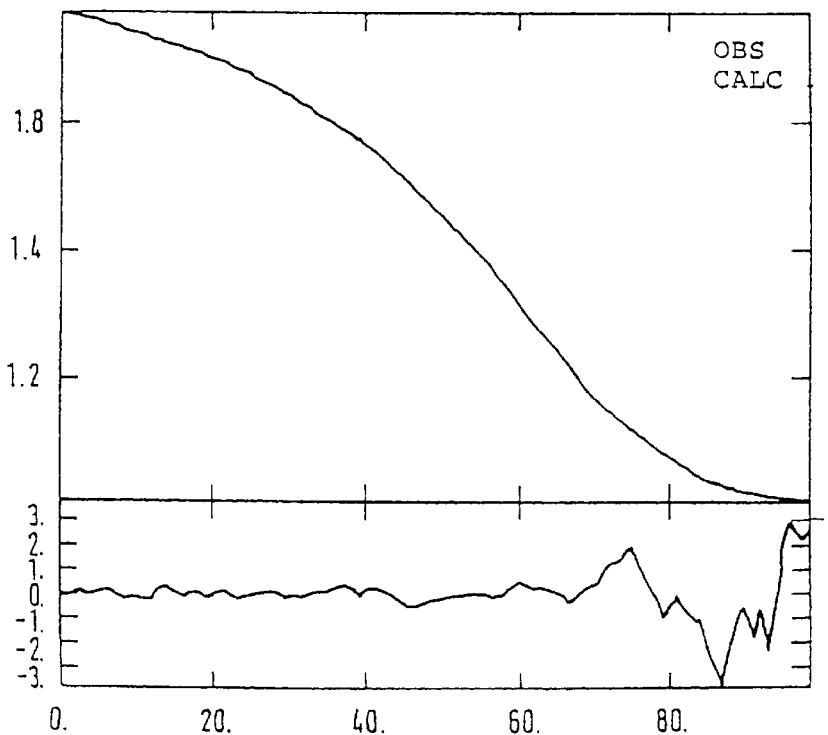
Figure 26C:
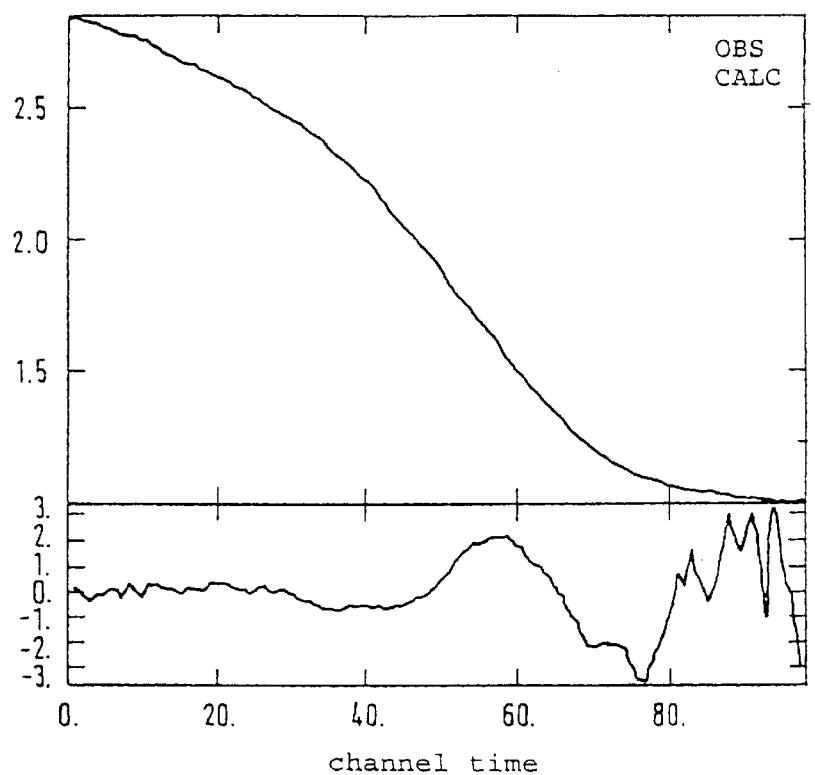
Figure 27:
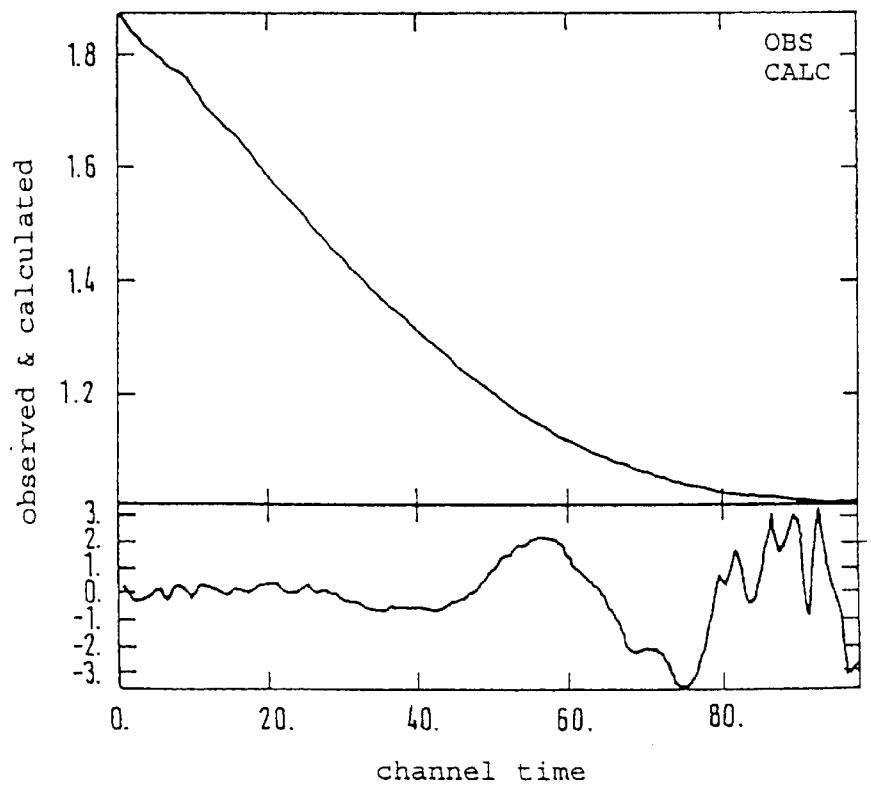
Figure 28A:
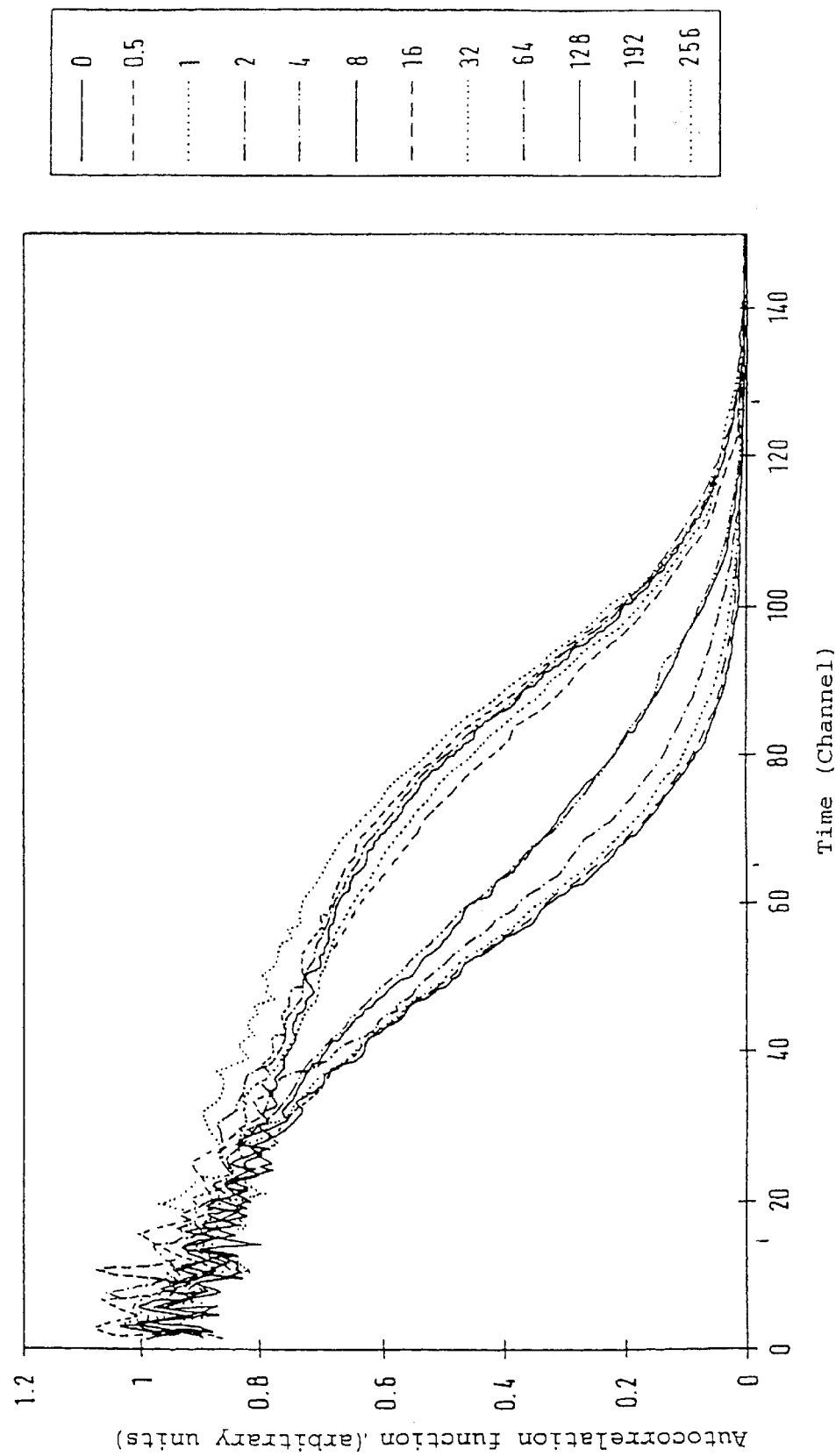
Figure 28B:
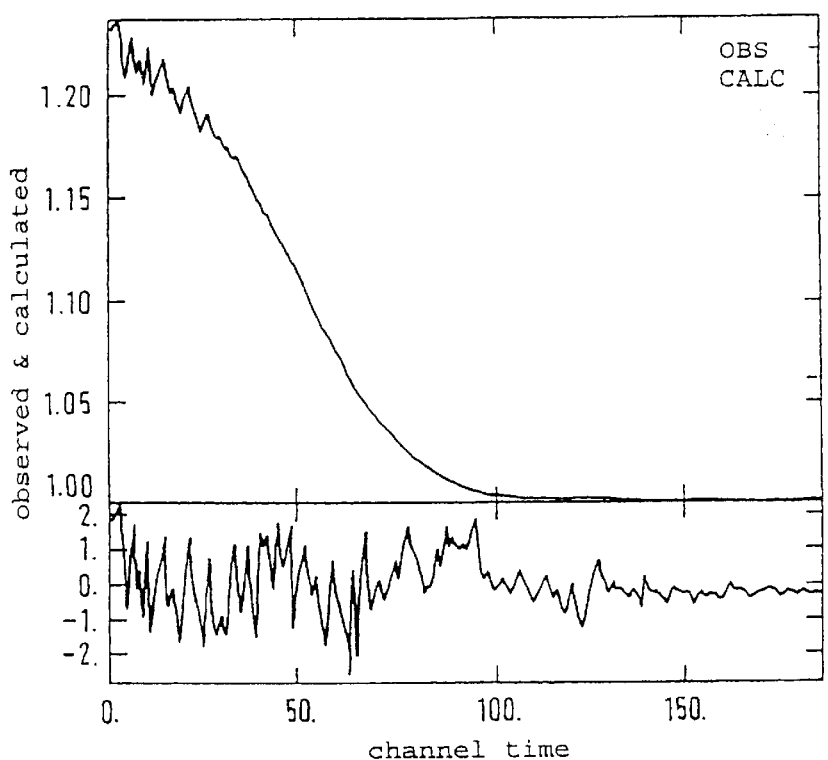
Figure 28C:
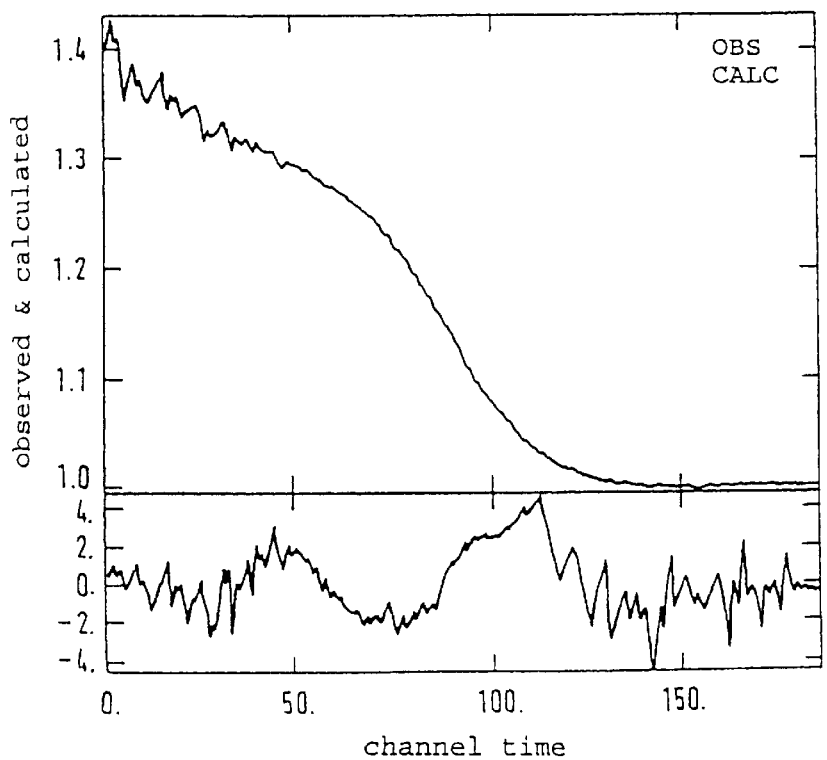

FIGS. 26 to 28 show the use of the FCS method according to the invention (i) for the determination of the behavior of a fluorescence labeled ligand with respect to association with a receptor of the outer cell membrane, (ii) for distinguishing between bound and free ligand, and/or (iii) for measuring ligand mobility in the case of a passage into the cytosol.

Alternatives (i) to (iii) taken together are an example for employing the method according to the invention in a dynamic laser scanning microscope with which three-dimensional imaging of the mobility of a labeled molecular species can be achieved, inter alia. From the distribution of concentrations of a particular molecule thus obtained, conclusions about the localization of this molecule can be drawn. This method also allows for an evaluation of the molecular state in the respective cellular or tissular compartments, such as e.g. association with compartmentalized target molecules (e.g. sense/antisense interactions with virus nucleic acids).

(i) to (iii) are examplified by the human epidermal growth factor (EGF) with a cell-bound receptor (EGF receptor) from rats. The cells bearing EGF receptors are NBD2 rat bladder cells derived from a respective tumor tissue. The cells are surface-fixed on Petri dishes in PBS buffer (phosphate buffered saline). They had been grown beforehand in standard medium until a confluent monolayer had been reached. The medium contained EGF labeled with tetramethylrhodamine. For excitation, laser light of 500 nm wavelength of an argon laser (0.5 mW) had been chosen. The free EGF factor has a rotational diffusion coefficient of $\tau_{Dfree}$=0.145 ms. Its concentration was 6 nM. FIG. 26$a$ shows the autocorrelation function of free EGF.

After 30 minutes of incubation with the cellular monolayer, an autocorrelation function according to FIG. 26$b$ is found in the case that the measuring volume comprises the region of the outer cell membrane (see also FIG. 5). 88% of the ligand detected by measurement is present in the receptor bound complex with the related diffusion time $\tau_{Dcomplex}$=14.54 ms. This time is a quantity relating to the diffusion of the receptor in the cell membrane. With the diffusion time $\tau_{Dfree}$=0.145 ms, 12% of the ligand are covered. About one EGF receptor is present in one space element. The related membrane surface is $0.5 \times 10^{-8}$ cm$^2$. After 30 minutes of washing, the autocorrelation function shown in FIG. 26$c$ is found from which the following can be seen: about 0.5 EGF receptors per measuring volume still retain the ligand bound with high affinity.

If the FCS measuring volume lies within the cytosol of a cell with a portion which at least predominates, then FIG. 27 is obtained (EGF in the cytosol). 38% of the internalized EGF is hindered in mobility (either through binding to receptors or through the influence of a viscous medium) (diffusion time $\tau$=3.3 ms), and 62% of the EGF has the same mobility as the free factor.

FIG. 28$a$ shows the interaction of a DNA oligonucleotide having the sequence M13/pUC (−21) primer (5'-TGACCGGCAGCAAAATGT-3') (SEQ ID NO:1) with a viral single-strand DNA of bacteriophage M13 which contains the corresponding complementary sequence. The oligonucleotide is labeled with Bodipy (Molecular Probes) at the 5'-C$_6$ position. The course of the association reaction with time was measured according to the invention in DNA in 10 nM tris buffer, pH 7.5, and 0.18 M sodium chloride. The variation of the successive autocorrelation functions reveals the kinetics of association. Autocorrelation was determined after 0, 0.5, 1, 2, 4, 8, 16, 32, 64, 128, 192, and 256 minutes. The diffusion time of the free primer is 0.17 ms, and 2.9 ms when complex-bound. FIG. 29 shows the course of the association as experimentally revealed as % fraction of the primer in the associated complex. A reassocation rate of 0.07 min$^{-1}$ results.

FIG. 28$b$ shows the example of autocorrelation of the labeled primer DNA. FIG. 28$c$ shows the autocorrelation function of a mixture of free and M13 DNA bound primer.

Cells of a measuring compartment can be analyzed in situ and in an essentially nondestructive way. This is especially relevant for pharmacokinetic investigations.

19. Kinetic Reaction Parameters

The possibility to determine diffusion times in terms of fractions of seconds allows to analyze the kinetic interaction of two molecules with high association constants and to determine recombination and dissociation rate constants. This is of special interest for the characterization of the interactions having high biological specificity, such as antigen/antibody, ligand/receptor, and the like interactions. Analysis of particularly slow processes with constants up to $10^{-6}$ s$^{-1}$ is easily possible due to the advantage of self-calibration inherent to the method according to the invention (FIG. 19).

20. Detection of Single Molecules

Figure 6:
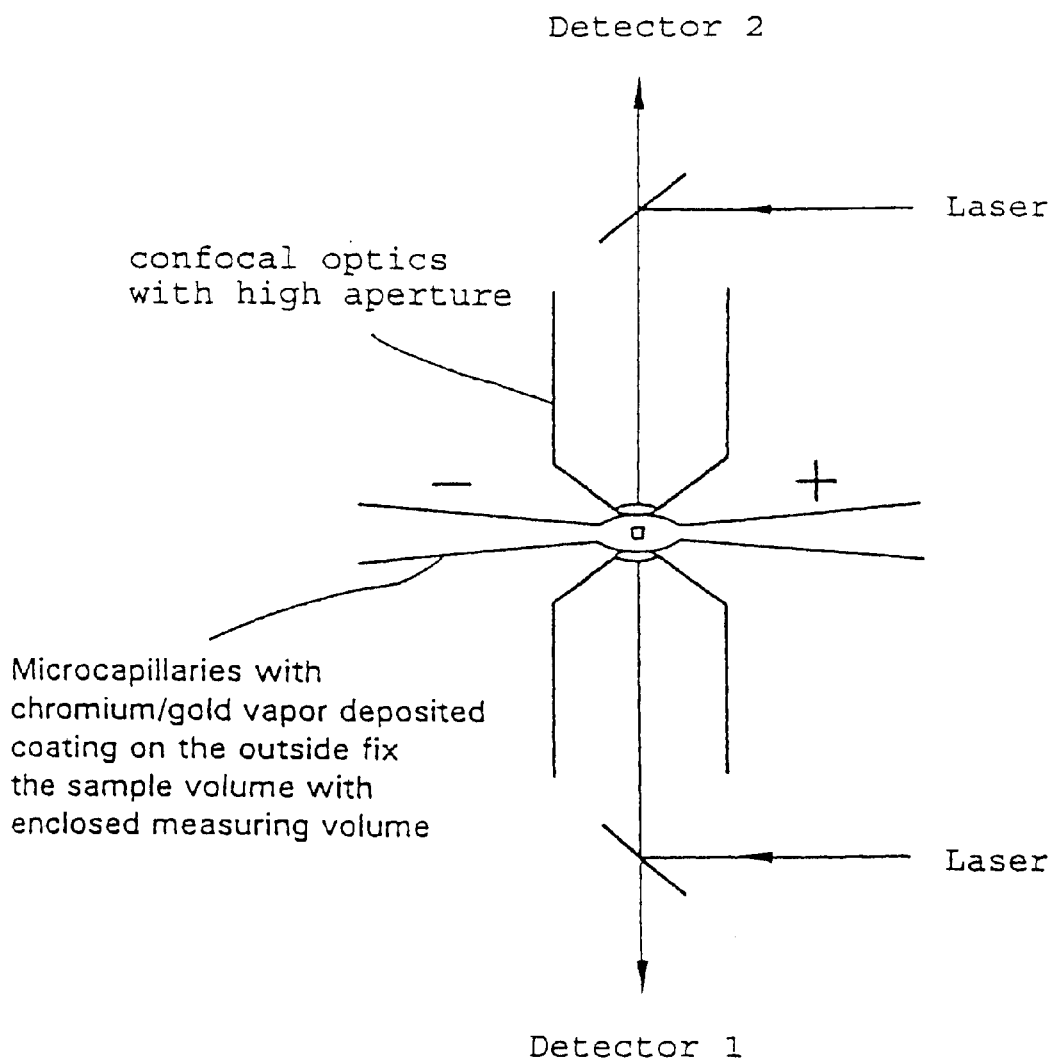
FIG. 6 is a schematic representation illustrating the detection of single molecules in an electric trap.

The high sensitivity of the measuring method allows for the observation of single molecules during their motion through at least one detecting laser beam. By using so-called "molecular funnels" in the form of special glass pipettes having outlets of $\leq 1$ $\mu$m, single molecules can He brought by flux into a laser beam having a diameter of 1–5 $\mu$m. By the action of electric fields, Brownian motion is restricted such that each molecule will pass through the site of maximum intensity of the laser beam. The arrangement of the optical units with opposing detectors and immersion optics makes sure very good photon flux as well as accuracy and efficiency of the detection of the luminescence emitted in all directions of space (FIG. 6). For instance, the arrangement is useful for the analysis of the sequences of single DNA or RNA molecules with the aid of exonucleolytic degrading (J. H. Jett et al., U.S. Pat. No. 4,962,037), but also for the detection of single molecules provided with label and charge.

21. Detection of Single Molecules by Using Electric Molecular Traps in Stationary or Alternating Field Single ionized molecules can also be held in the observation volume element by forced directed translation in an electric field. Alternatively, single or repeated translation through the volume element can be forced. This is preferably done in an arrangement which is shown schematically in FIG. 6. A flux of molecules passes a larger sample volume in the center of which the observation volume is located. By an electric field which may be a stationary or an alternating field, migration of charged molecules through the observation element can be forced. In this way, molecules can be quasi-focused. This "molecular focusing" is important in the case that only one or a few molecules are present in the total volume element which will have to be detected quantitatively.

To do this, the sample volume is preferably fixed as a microdroplet between the outlets of two microcapillaries as have been described by B. Sakmann and E. Neher. The capillaries are vapor-coated with a conductive metal layer, preferably gold on chromium priming, which is in contact with the aqueous buffer system at the outlets of the capillaries. The measuring element is located inside the sample droplet wherein the emergence objective of the microscope is in direct contact with the droplet or the droplet is separated from the objective by a sheet.

Once a single molecule or molecular complex is detected in the measuring element after having left the end of the capillary, kinetic data can also be obtained. It is not very complicated to technically realize a field or temperature jump in the small volume element. If reaction complexes exhibit a Wien effect or have a sufficiently high reaction enthalpie, those parameters can be used in relaxation methods, e.g. to determine reaction rate constants.

Figure 20A:
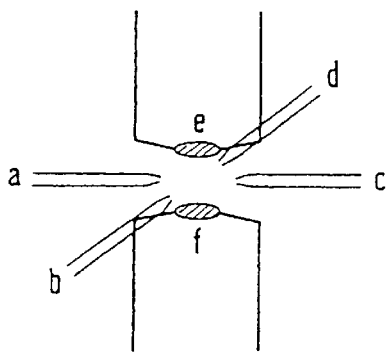
FIGS. 20a, 20b, and 20c are schematic representation illustrating embodiments of an electric trap according to the invention.
Figure 20B:
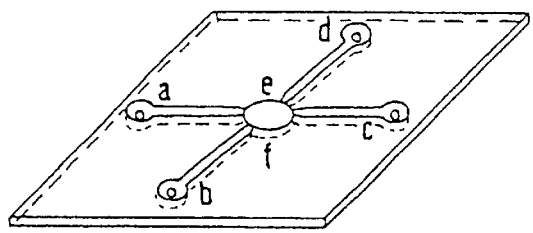
Figure 20C:
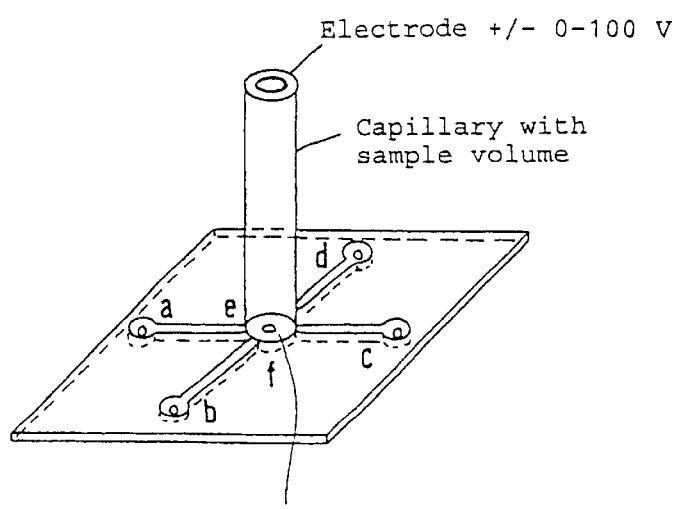
Figure 21A:
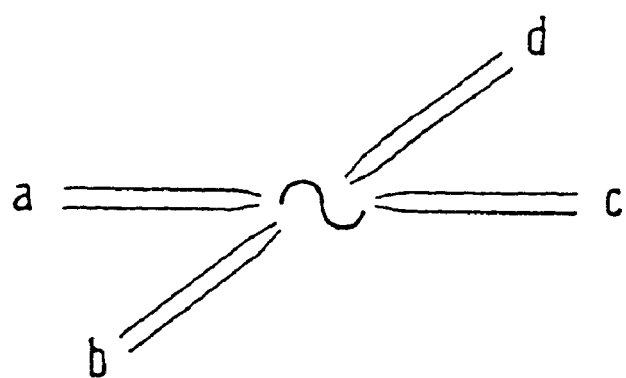
FIG. 21a is a schematic representation illustrating molecular detection according to the invention.
Figure 21B:
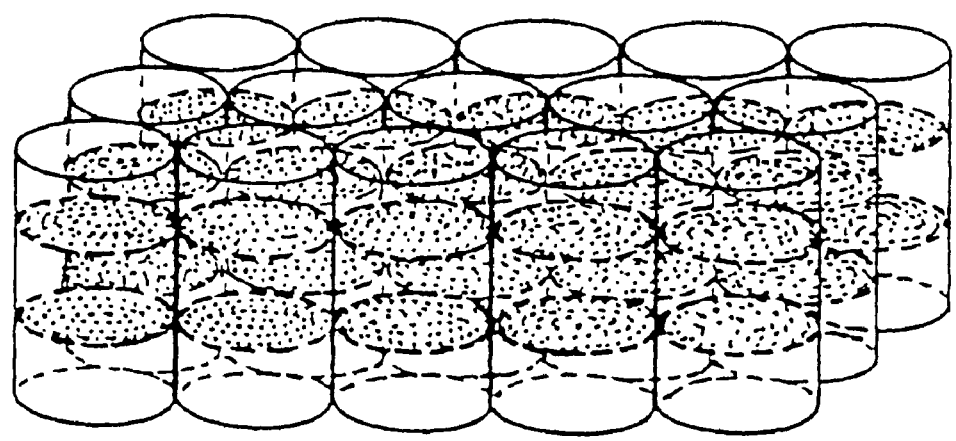
FIG. 21b is a schematic representation illustrating a multi-element detector.

The principle of single molecule detection with carrier-free, electrically mediated concentration of charged molecules, such as nucleic acids, in the measuring volume is of great significance for the analysis of single molecules in highly diluted solutions. Two aspects are prominently important therein: the active transport according to the invention of one or a few molecules from a larger sample volume of 10–1000 µl into the measuring volume of about $10^{-9}$ µl means a concentration by a factor of $10^{10}$ to $10^{12}$ (FIGS. 20, 21).

One molecule per ml means a concentration of about $10^{-21}$ M. With a concentration as described, this means a final concentration of $10^{-9}$ M in the measuring volume. Thus, as described in the section DNA analysis, hybridization with simultaneously concentrated dye-labeled probes can be performed with fast reaction rates.

This means a notable progress for diagnostics. In this way, diagnoses with a sensitivity not realized hitherto can be performed, particularly while omitting enzyme-based amplification procedures and the problems related thereto, such as risk of contamination by amplification products. This is of special importance in bacteria and virus diagnostics.

If the viruses or bacteria are present in diluted solutions and are not contaminated with a large excess of accompanying nucleic acids that are also negatively charged the analysis can take place without preliminary separation of contaminating nucleic acid. This is the case, for instance, in forensic analyses when extremely small amounts of biological material is to be genetically analyzed. In clinical analyses, this is the case with cell free supernatants of body fluids, such as sputum, urine, or plasma.

A large amount of accompanying nucleic acids may interfere with the concentrating process and the subsequent hydridization. However, the nucleic acid can be preliminarily enriched, e.g. by means of specific hybridization methods. To do this, certain nucleic acids are extracted from a large volume, e.g. by offering a molar excess of solid phase coupled counter-strand probes which preferably are not homologous with the probe, and are thus separated from contaminating, accompanying nucleic acids. Subsequently, the nucleic acids are released to concentrate them in the measuring volume according to the invention.

In principle, other molecules can also be concentrated in the measuring volume by means of the electric trap according to the invention. A specific character of being charged of the target molecule is required which is either an intrinsic property of the molecules, such as in the case of nucleic acids, or a charge established by conditions of the medium, or a charge generated by reaction with a particular ligand.

In a preferred procedure according to the invention, the specific dye-labeled probe or the labeled ligand in detection reactions other than for nucleic acids can be construed such that the test molecules are transported into the measuring segment, mediated by the electric field, only after the specific complex formation has already happened. According to the invention, this is achieved by the non-complexed probe being uncharged or even bearing opposite charge with respect to the target molecule and the complex of receptor-target and ligand to be concentrated in the measuring volume.

FIG. 30 shows the movement of charged molecules in a dipole trap. Variations of concentration and oscillations of negatively charged rhodamine labeled dUTP molecules in water in a laser illuminated volume element are shown at an oscillating electric field with a field strength of 10 kV/cm and a frequency of 4 Hz. The optical axis of observation runs perpendicular to the field gradient (see FIG. 6). The effect of concentrating the molecules in the measuring volume becomes evident. This concentration effect is cancelled in the moment when the field is switched off and the molecules leave the observation volume element by diffusion. Comparable results can be obtained by means of opposing microcapillaries as described in FIG. 6.

Figure 31A:
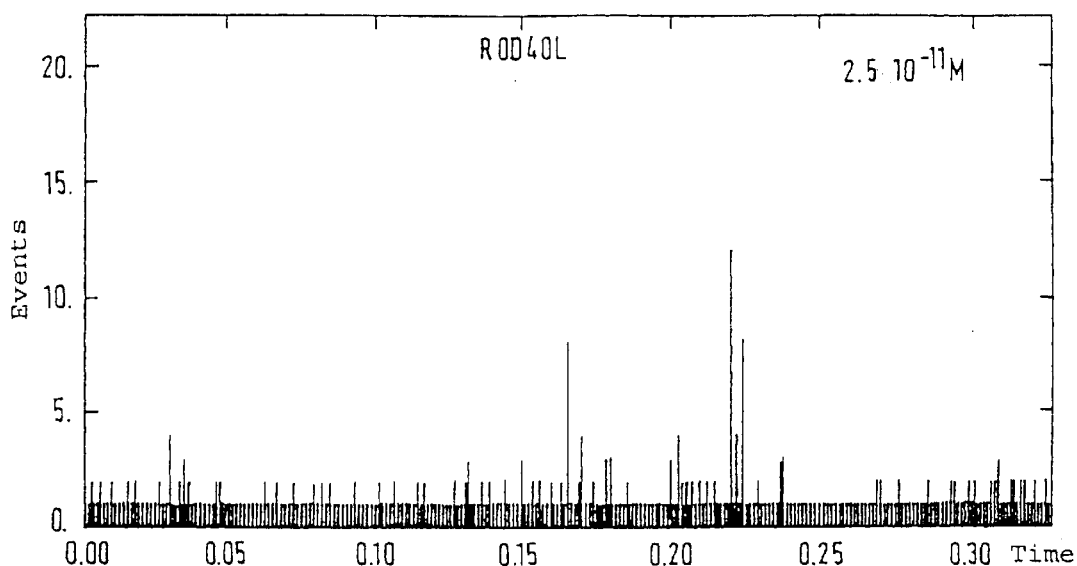
Figure 31B:
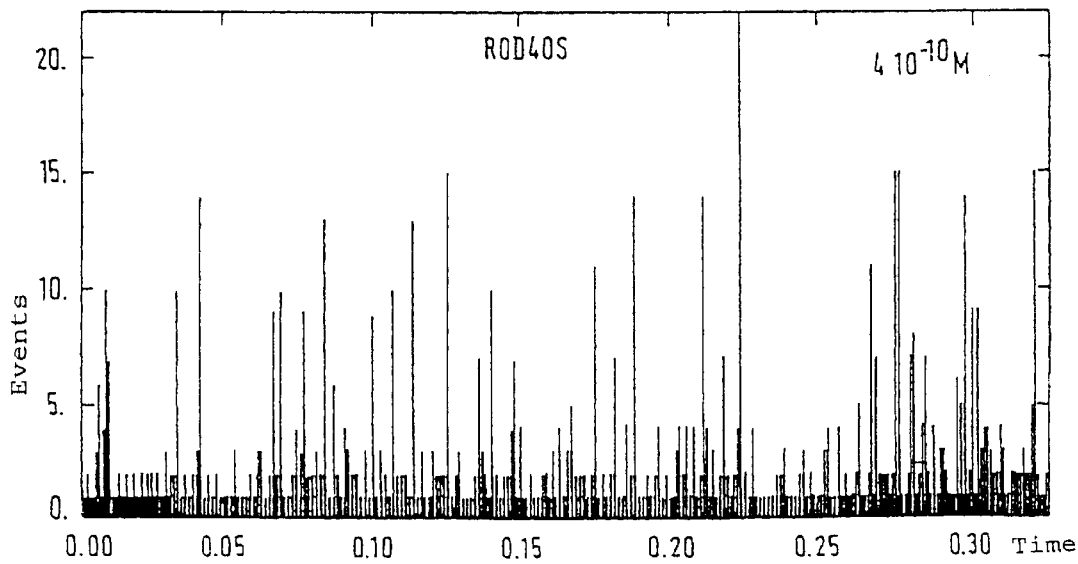

FIG. 31 shows photon showers of single rhodamine 6G molecules in water. By photon shower is meant the sum of the detected photons received while the molecule is present within the Gaussian measuring volume. Thus, the possibility of reliable detection of single molecules with a single chromophor has been proven. FIG. 31a: $2.5 \times 10^{-11}$ M; FIG. 31b: $4 \times 10^{-10}$ M. The channel time was $4 \times 10^{-5}$ sec in each case=diffusion time; Gaussian measuring volume 0.24 fl.

22. PNA (Protein-like Nucleic Acid)

Particularly suitable molecules according to the invention are those whose behavior of binding to nucleic acids is an especially tight one because they are uncharged or even contribute to electrostatic stabilization of a complex through a charge opposite to that of the phosphate backbone. Molecules capable of hybridizing must not necessarily have the chemical character of a nucleic acid. So-called PNA molecules have been described which can be used according to the invention to particular advantage.

In the case of a relatively long-chained nucleic acid target this can be achieved by the excess negative charge of the target molecule determining the electric charge and the electrophoretic separation behavior and e.g. overcompensating the opposite charge of a probe molecule. In this way it can be achieved that the complexed target molecules are selectively concentrated in the measuring segment after completion of the hybridization whereas the excess of labeled probe molecules is eliminated from the measuring segment.

For instance, the method according to the invention also allows for direct detection of single virus particles in a volume of about 100 µl–10 ml (corresponding to $10^{-20}$–$10^{-22}$ M) of serum fluid without enzyme-based nucleic acid amplification procedures.

For the nucleic acid based positive detection in serum samples serving as an example herein, the following requirements must preferably be met:

The mentioned amount of serum fluid must contain at least one virion with nucleic acid (DNA or RNA) accessible for hybridization.

The solution must contain a highly specific nucleic acid probe according to the invention as a test reagent with fluorescence labeling. The length of the probe must be chosen such that high specificity with respect to the target sequence is ensured because RNA molecules might possibly occur in the serum in high molar excess.

When choosing the length of the probe, the stability of its binding to the complementary RNA or DNA must be considered. The dissociation rate ought to be below $10^{-5}$ sec$^{-1}$, if possible. This means that the hybrid will remain stable for about one day even after the free probe molecules have been removed, i.e. when the equilibrium at a presumed concentration of $10^{-20}$ M lies entirely on the side of the dissociated molecules. According to the invention, this happens when the free probes are diluted by electrophoresis later, preferably to $10^{-20}$ M.

When hybridizing, the probe must be present in so high a concentration that association and hybridization take place within seconds to minutes. According to the invention, low concentrations can be used if the substances discussed below are added to the hybridization medium to accelerate association.

The probe is chemically linked to at least one, preferably more fluorescent dyes according to the invention. The electrophoretic mobility of the free probe should be different from that of the complexed probe. This can be achieved simply by making use of size differences or differences in conformation or, according to the invention, by using probe derivatives with a modified, neutral or positive, charge character.

The analysis according to the invention takes place in the device claimed according to the invention combined with a specialized electrophoretic unit described in a preferred embodiment.

It consists of an electrophoresis cell with capillary outlet (diameter about $10^{-3}$ mm) and is combined with the single molecule fluorescence device (FCS) according to the invention.

Figure 12:
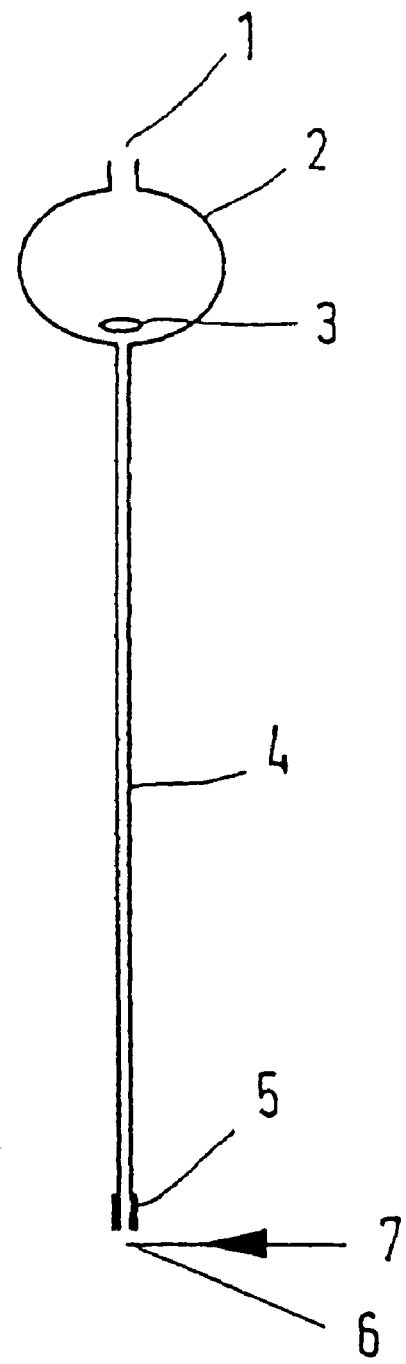
FIG. 12 is a schematic representation illustrating an electrophoresis cell.
Figure 13:
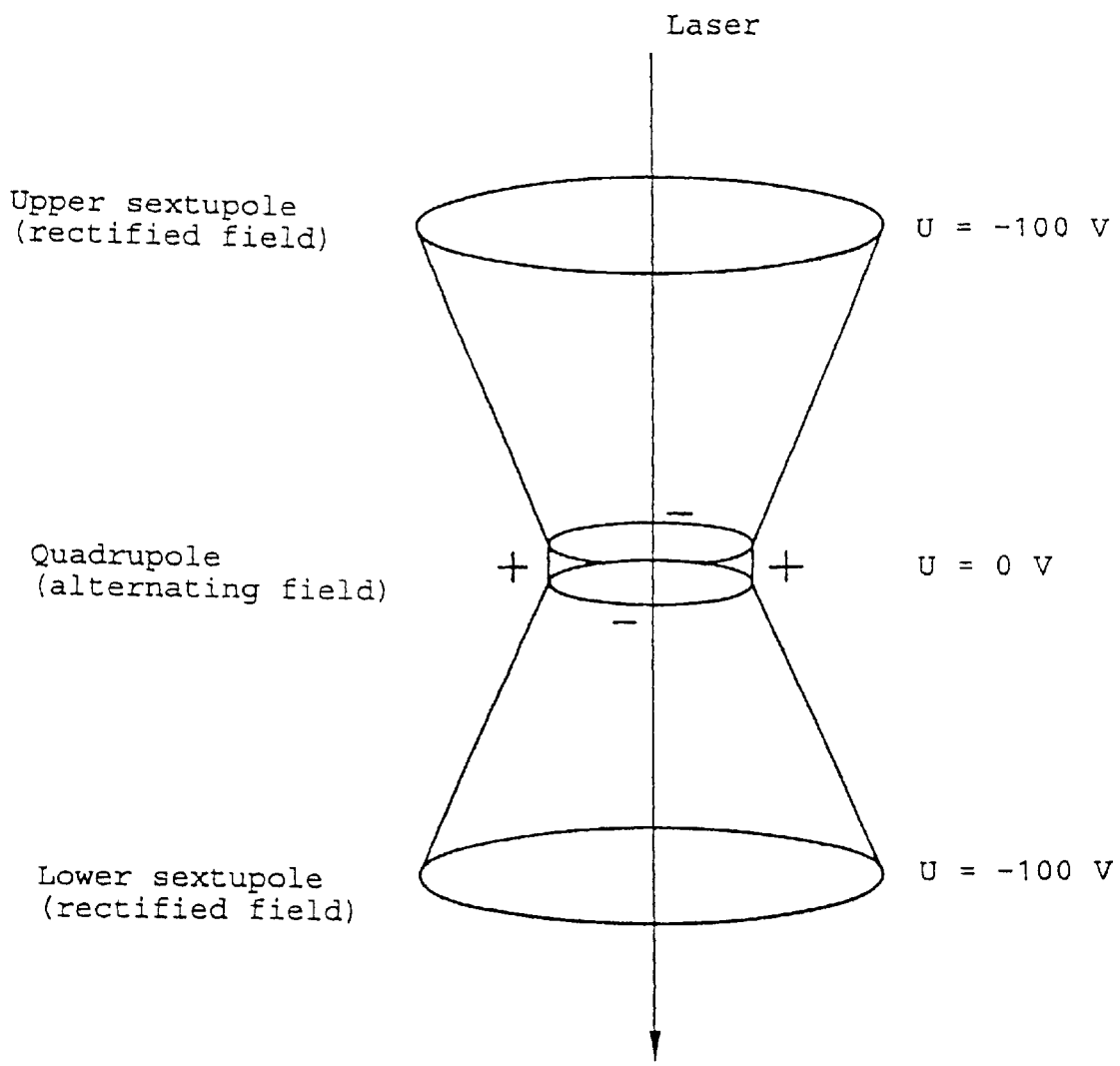
FIG. 13 is a schematic representation illustrating the field about a laser beam.

FIG. 12 schematically describes a preferred embodiment of electrophoresis cell. It contains (1) at least one opening for the addition/collection of the sample to be analyzed and/or a washing solution; (2) wall electrode; (3) ring electrode; (4) Neher capillary; (5) golded tip as an electrode; (6) droplet outlet; (7) laser beam.

The electrophoresis cell is filled with the measuring sample to which a primer solution is added as accurately dosed as possible. Between the wall and ring electrodes, a voltage is applied e.g. over a time switch resulting in a concentration of probe and hybrid in the ring electrode within minutes. Thereafter, high voltage is preferably applied—again over a time switch between wall electrode and capillary tip. The length of the capillary should be such that from this point separation of free probe and hybrid will take place due to electrophoresis as properly as possible. The free probe should appear at the outlet of the electrode within a period which is clearly different from the period after which the measuring impulse of the hybrid comes in so that at this time the concentration of unbound primer is sufficiently diluted. Preferably, the solution comes out as a droplet so that no back diffusion can take place. Both time spans: $T_s$, after which the impulse of the free probe will appear, and $T_z$, after which the impulse of the hybrid will appear, are fixed, if possible. The hybrid will appear in a microdroplet at a given time and can even be detected in terms of single molecule fluorescence. Optical measurement can also take place before the exit from the capillary.

Detection of single molecules is difficult if the disturbing signals from the free probe are too strong. Single molecules per ml means $10^{-20}$ to $10^{-22}$ M. Because of the reaction times, however, probe concentration for association must be about $10^{-10}$ M. In this case, the combination with electrophoresis according to the invention allows for a very much sharper separation than with the described difference measurement of an unseparated mixture. In addition, the hybrid which is possibly formed appears within a volume, whose order of magnitude is $\leq 10^{-12}$ l, at a time which can be accurately calculated, and thus it is well detectable for the method according to the invention. By selecting appropriate fluorescence labels, fluorescence can be made optimal.

23. Device for Preparative Selection of Desired Labeled Complexes in Terms of a Single Molecule Sorting Method With or Without Combination With a Molecular Trap In case a molecule, molecular complex, virus, or cell has been recognized by FCS as a desired target molecule, the possibility exists for direct preparative enrichment. This assumes that by electrophoretic migration the respective molecule is present at a defined place at a defined time shortly after measurement and can be electrophoretically separated there.

Measurement of Mobilities in an Electric Field, Running Time Measurements in Capillary Electrophoresis, Running Time Correlation, Sequencing Through measurement of the mobilities of molecules or molecular complexes in an electric field, e.g. using methods of capillary electrophoresis, information about the nature of the molecules can be obtained. Thus, amino acids of a protein or peptide as products of Edman degradation, for example, with fluorescent label can be determined through this electrophoretic mobility. In recent years, sequence analysis of peptides and proteins has become increasingly important. It has been a critical break-through to use analytical amounts of a protein in gas phase analyzers as commercially available by now. In this way, the proteins from single spots of two-dimensional gels (O'Farrell gels) can be sequenced.

The efficiency of this method could be significantly enhanced further if the sensitivity of analytical determination of the degradation products in a subsequent capillary electrophoretic evaluation could be increased. Compared with conventional detection methods, peak determination by FCS in combination with running time determination (running time correlation) allows for surprisingly high sensitivity. Thus, analytical amounts of peptides and proteins which can be obtained by capillary electrophoretic methods are sufficient for sequence determination. As the initial amount, a single cell may be enough to be able to perform sequence analysis for a protein contained therein. On the other hand, the sensitivity of the method allows for the structure of a substantially longer sequence of 2D gel electrophoretically separated proteins, peptides or cleavage products to be determined.

An enzyme-based amplification reaction such as PCR cannot reach such sensitivities without considerable additional steps. The known problems with enzyme-based amplification relating to contaminations with highly amplified products do not occur in the method according to the invention.

The method according to the invention in combination with electrophoresis is not limited to application for nucleic acids. Proteins and protein complexes or low-molecular chemical ligands can also be provided with charge carriers that allow for analysis according to the invention. For instance, negatively or positively charged oligopeptides can be coupled to antibodies prepared by recombinant techniques in order to subject them to electrophoresis under non-denaturing conditions. Thus, even lower virus titers can be detected, for instance when antigen analyses of surface proteins are performed which occur in large numbers per virion or are,even secreted isolatedly into the serum.

A variation of the electric trap to detect single molecules is the incorporation of a quadrupole instead of a dipole. By applying an alternating field in the plane of the quadrupole, a charged molecule can be prevented, at appropriate field strengths, from thermally diffusing out of the quadrupole region. If two additional electrodes are arranged, according to the invention, above and beneath the quadrupole (sextupole), then charged molecules will drift, after an appropriate voltage has been applied between the outer sextupole electrodes and the average potential of the quadrupole, into the alternating field of the quadrupole and be concentrated there.

The sextupole electrodes can be formed by metal coated glass surfaces of two microscope objectives. If a single molecule is present in the volume of the sextupole of about 40 μl, then this corresponds to a concentration of $4 \times 10^{-20}$ M. With a voltage of 100 V between the sextupole electrodes and the quadrupole plane (distance about 1 mm), a nucleic acid molecule will drift into the quadrupole plane within about one second. The molecule now held within the quadrupole plane is present in a volume element of about 6 fl corresponding to a concentration of about $2.5 \times 10^{-10}$ M and an increase in concentration by a factor of $6.4 \times 10^9$. Its presence is proven by determining the number of molecules (N=1) and the diffusion time which is characteristic for this molecule.

The voltages and voltage differences actually employed in the quadrupole and/or sextupole depend on the ionic strengths of the analyte solution.

When a position-sensitive detector is used (avalanche photodiode detector), whose different elements represent different space portions or quadrupole planes, the electric field gradients can be arranged, through a feedback arrangement between detector elements and the poles (electrodes) of the quadrupole, such that the molecule is always held at a fixed position within the quadrupole. This position is defined by the respective detector element.

24. Electric Trap

For convenience, the "electric trap" mentioned above is realized by arranging the measuring compartment with essentially equal distance between two positively (negatively) charged poles (electrodes) lying on a common axis which goes through the measuring compartment. In the plane perpendicular to this axis there are at least two and preferably four electrodes between which an alternating electric field is formed. The electrodes are arranged in such a way that they or pairs of them are facing each other. To these electrodes a rotating alternating electric field is applied in which the positively (negatively) charged molecules are located. Due to the electric charge of the two electric poles perpendicular to the alternating field, the molecules are restrained from movement out of this alternating field. When the double microscope is used which has been mentioned above and will be described in more detail later, the electric poles are preferably the supports of the two opposing objective lenses in the common focus of which the measuring compartment is arranged.

When the electric trap is used in routine analyses, it is important that a target molecular complex get from a relatively large sample volume (10–100 $\mu$l) into the very small measuring volume for observation. To achieve this, the charged target molecule is brought, for convenience and according to the invention, over a large potential gradient into a volume element with zero potential out of which or inside which it can be controlled by multipolar fields, e.g. quadrupolar fields, e.g. for fixation in and/or controlled motion through measuring volumes. Preferably, this is done in a capillary with a length of several millimeters or centimeters (FIGS. 20, 21) which will receive the sample and at one end of which a voltage of e.g. +100 (or –100) V is applied and the other end of which lies at a potential of 0 V. The electrode lying at 0 V has a pinhole behind which there is e.g. a quadrupolar alternating field on a low voltage level (see FIG. 20). According to their electrophoretic mobility $\mu$=ca. $10^{-4}$ to $10^{-6}$ cm$^2$/Vs, target molecules quickly migrate into the pinhole and then move on into the geometrically adjacent quadrupolar field. The capillary is made of e.g. glass or quartz, if it is desired to superimpose electroosmotic effects on electric migration as is done in capillary electrophoresis. Alternatively, capillaries made of e.g. Teflon with uncharged surfaces can be used in which case electroosmotic effects can substantially be excluded.

25. Fitness Determination of Variant Spectra in Large Sample Collectives

Within the scope of evolutionary screening assays, the method according to the invention is useful for the determination of the binding of ligands to molecules (proteins, peptides, nucleic acids, antibodies) which are to be selected. The extreme measuring sensitivity achieved by the method allows, in particular, for analysis of highly specific interactions, which are e.g. of particular physiological or biochemical interest. The interaction is measured through binding of a ligand or labeled ligand or through competition of the unlabeled ligand with a labeled inhibitor. Thus, fitness determinations of variant spectra can be performed primarily in large sample collectives.

Fitness parameters may be:

affinity parameters kinetic parameters enzymatic parameters under Particular medium conditions of the test.

26. Sample Carrier Systems for Genotype/phenotype Couplings

In the analysis according to the invention and in the evaluation of large sample collectives of phenotypic variants it is critical that the corresponding genotype, e.g. the encoding plasmid or the encoding mRNA, can subsequently be singled out to continue the evolutionary process. This problem is by no means a trivial one. The process will be the more successful, the more selectively this singling out is done, that is the more precisely the corresponding genotype can be isolated without contaminating it with sequences coding for useless phenotypes.

27. Test Cells

With medium sample numbers (<10,000) volume elements can be employed which are arranged in fixed spatial separation and are referred to as test cells hereinbelow. These can be parts of a sheet system comparable to those described for PCT/EP 89/01320, PCT/EP 89/01387, PCT/DE ;91/00082, PCT/DE 91/00081, PCT/DE 91/00083, PCT/DE 91/00704, wherein individual volume elements contain samples in sealed sheet elements. From the sealed elements, Phenotypes which have once been identified can be isolated along with their encoding genes or mRNA transcripts by direct mechanical access.

28. Microcompartmentalization

The method, according to the invention, of optical measuring and evaluation of variants in ultrasmall sample volumes also allows for very small total sample volumes in form of a microcompartmentalization which cannot, however, be handled in a trivial way. This is true for both individual filling and selective emptying of the compartments to prepare a genotype identified as being positive.

Microcompartments can be built up from regular and irregular porous carriers, such as capillary elements arranged in the parallel as described in the patent application DE 42 37 383.1, or flat carriers made of porous materials such as glass with controlled pores or capillaries whose volume elements are separated one-dimensionally within the capillary but of which pairs are in direct contact.

A particularly preferred form of microcompartmentalization is depicted in FIG. 4. Under an optically transparent flat carrier, the volume elements present in a sample to be analyzed in the form of recombinant or natural cells or artificially vesicular elements with their respective phenotypes and genotypes are applied. In another embodiment, volume elements are established only during application to the carrier or thereafter. Gel or vesicle forming polymers, especially polymers based on thermoreversible structures, such as caprolactam derivative polymers, are especially preferred.

Application can be performed first from a homogeneous solution with subsequent segregation of the polymers to form separate aqueous volume elements, or through application of microdisperse droplets by means of a piezo-controlled microdispenser.

In the way described, the contents of cells can also be analyzed. For example, cells can be enclosed in the described vesicular structures and later lysed at higher temperatures. In this case, at least partial mixing of the solution enclosed in the vesicles and containing reactive molecules or molecular complexes with the contents of the lysed cell will occur. Reactive molecules can be e.g. nucleic acid probes, enzymes or proteins which will undergo specific interactions or reactions, which can be detected and quantified by the FCS method according to the invention, with cellular components. This technique is analogous with in situ hybridizations or cell specific protein staining.

Carriers for simultaneous fixing of nucleic acids and the phenotypic molecular structures to be analyzed, such as those described in the application of K. Henco et al., DE 42 37 381.6, are also useful as a preferred reaction carrier to achieve genotype/phenotype coupling.

Of course, carriers such as those employed by S. Fodor et al. within the scope of the so-called AFFYMAX technology in which the genotype is defined by its x/y position on the carrier can also be used.

29. Photomarking of Selected Phenotypes

Figure 7:
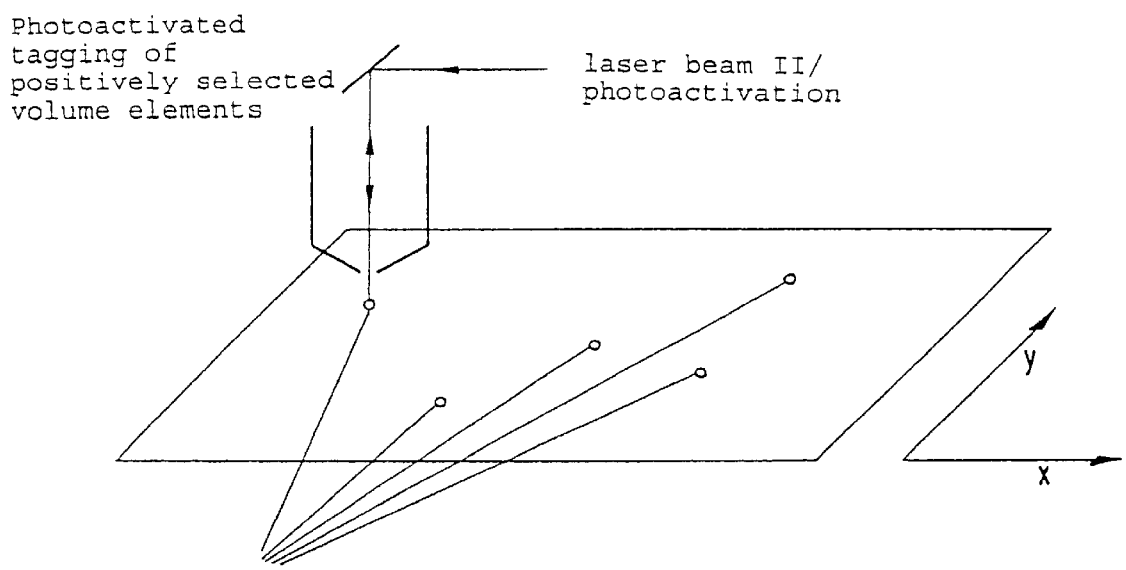
FIG. 7 is a schematic representation illustrating the tagging of selected genotypes using FCS.

One preferred possibility of addressing and marking of variants selected according to the invention within their respective volume elements is photooptical marking of their position by using the described analytical optics (FIG. 7). This may be done by reflecting in light of a wavelength by which a photoactivatable coating on the surface of the carrier can be excited to produce, e.g. by selective discoloring, a reaction product which is easily recognized. The light signal is activated if correlation analysis indicates a given predefined valence of the respective volume element analyzed.

A conventional photoreactive coating can be employed therein. An additional light source, preferably also a laser light source, may be used, or the laser employed for analysis may be used. Discrimination between measurement and marking of the position by photoactivation can be achieved e.g. by using a frequency doubler for the marking reaction. The x/y positions of desired elements can also be collected by electronic data storage.

After marking of the positions on a carrier, the desired nucleic acid can be obtained from the corresponding volume element, for example, by mechanical access.

30. Photoactivation of Selected Phenotypes and Genotypes

Instead of marking the selected volume element, marking of the corresponding genotype itself according to FIG. 7 has proven to be particularly useful according to the invention.

According to the invention, several alternatives are preferred:

(1) photoactivated attachment of the nucleic acids to surface structures of the volume element,
(2) photochemical activation of nucleic acid specific ligands,
(3) photochemical inactivation of nucleic acids in all volume elements except the positively selected ones.

Within the meaning of alternative (1), psoralen derivatives can be employed, for instance, which chemically link nucleic acid counter-strands to one another, as double strand intercalating reagents, under 360 nm light exposure. Such ligands can be chemically linked, for instance, with the carrier surface (FIG. 8).

In this way, a sufficient number of phenotype encoding plasmid copies can be attached to the positively selected surface segments during the screening. Subsequently, all nucleic acids that have not been fixed can be washed off. Then, the selected nucleic acids can be subjected to an enzyme-based amplification reaction directly on the surface.

Alternatively, the nucleic acids can be recovered by making use of the reversability of psoralen linking. This may be done, for instance, by light of 260 nm wavelength. According to alternative (2), the nucleic acid binding ligands can also be linked to other molecular elements which allow for ready subsequent purification and separation of undesired nucleic acid structures. This may be exemplified by: coupling of DNA or RNA recognizing ligands, particularly photoactivatable psoralen derivatives or intercalating dyes, coupled to affinity ligands, especially biotin, avidin, streptavidin, immunoglobulin, oligopeptides, or oligonucleotides.

According to FIG. 8, after light-induced chemical linking of those compounds with DNA or RNA from the positively selected volume elements it becomes possible to purify DNA and/or RNA from all volume elements together and simultaneously separate them from the nucleic acids which have not met the selection criteria. Separation can preferably take place by hydrophobic chromatography, affinity chromatography, or by using magnetic particles, wherein the surfaces have appropriate properties of binding to the ligand of the adaptor molecule. Preferred examples of such specific coupling are: oligo-dT/oligo-dA, avidinstreptavidin/biotin, NTA-IDA/(His)$_6$ and similar known complex forming agents.

In the subsequent step, the purified nucleic acids thus pooled can either be directly subjected to an enzyme-based amplification reaction or to cDNA synthesis, or can first be decoupled from the ligand by reversion of the photochemically induced linking.

In the sense of the invention, one could also think of selectively inactivating the nucleic acids which do not meet the selection criteria of the analysis [alternative (3)]. This can also be done with cross-linking substances such as psoralens, wherein cross-linking will occur in such a way that the structures thus cross-linked are no longer capable to be amplified in successive enzymatic reactions. However, one drawback of this method is that inactivation must be accomplished quite completely because otherwise the enrichment factor for the positively selected volume units is adversely affected. In the methods of alternatives (1,2), the yield of enrichment is not of prevalent importance. By means of enzyme-based amplification methods, very low numbers of copies can also be enriched to be covered according to the invention. However, for most of applications it is advantageous if as large as possible a fraction of the nucleic acids from a positively selected volume element can be preparatively covered. This can be achieved e.g. by means of optics illuminating a larger volume element than the volume element considered in the analysis.

31. Fraction Analysis/flow Injection Analysis/GC/MS Coupling

Flow injection analysis with coupling to analytical/preparative separation methods is of particular importance in coupling methods according to the invention to methods of unsharp chemical or biochemical reactions to find active substances or optimize (DE 43 22 147 and WO92/18645) chemically or enzymatically generated quasi-species.

As has been set forth above, the present method is particularly useful for the analysis and evaluation of molecular collectives which are complex in terms of number and have been preliminarily generated in an evolutionary process. Functional analysis of complex systems with molecular diversity, however, is also of considerable significance in cases apart from that. Diversity does not only emerge due to evolutive systems in terms of replicative mechanisms just as compartmentalization of subpopulations does not only occur in cellular or vesicular structures.

In synthetic chemistry, very complex systems of different molecule types are produced deliberately or unintentionally wherein a given kind of complexity can also we selectively generated. Microorganisms or plants synthesize a variety of secondary metabolites from which a great number of pharmacologically active structures have already been derived. With chromatographic methods, such as HPLC, FPLC, gas chromatography etc., such compounds can be efficiently separated and isolated, as is well known.

The method according to the invention does not only make accessible parallel analysis of mutants/variants from so-called replicative systems, such as nucleic acids or proteins, but also those from chemically or metabolically complex mixtures. Conventionally, to date the procedure was to first purify complex mixtures preparatively in individual fractions, to analyze them chemically and/or reveal their structures and, if possible, to make them enter biological assays individually in the form of pure substances.

Now, with the method according to the invention, preparative use of the fractions or individual materials, which are present only in analytically small amounts at first, e.g. for pharmacologic assays can be achieved. In a preferred embodiment of the method according to the invention, the obtained fractions are directly linked to an FCS assay. Producing individual substances before they positively respond to the respective problem in FCS assays is omitted. Blind screening for active substances as presently performed can be replaced by the possibility to selectively investigate fractions containing active substances.

Analysis of functional compounds in complex mixtures of materials is an ambitious task of pharmaceutic chemistry. Primarily, the complex mixtures of natural substances from microorganisms and plants already mentioned are known. Japanese institutions and companies have achieved a lead in screening natural substances with respect to the other nations which is difficult to be caught up on by persistently, since the first antibiotics had been introduced, establishing extended banks of purified substances with revealed structures which can be introduced into a screening in each new assay. This is much simpler than cultivating organisms each time anew, especially since the risk of repeated detecting, meaning double developments of active structures which are known per se, is avoided in this way.

Due to its advantageous properties, the method according to the invention can renounce on this proceeding and nevertheless allows for analysis of very extended and complex mixtures, since individual-molecules are covered virtually as pure substances. One should remember that a single microorganism can synthesize more than one thousand complicatedly structured secondary metabolites some of which can only be present in small amounts and cannot be identified by their functions in an analysis of the entire mixture of an extract. According to the invention, mixtures of substances from a microorganism or a mixture of several microorganisms or plant extracts can be separated first e.g. by chromatography to test the individual fractions for the presence of functional compounds preferably "on-line" in a capillary at the end of a separation matrix (see FIG. 9).

Figure 9:
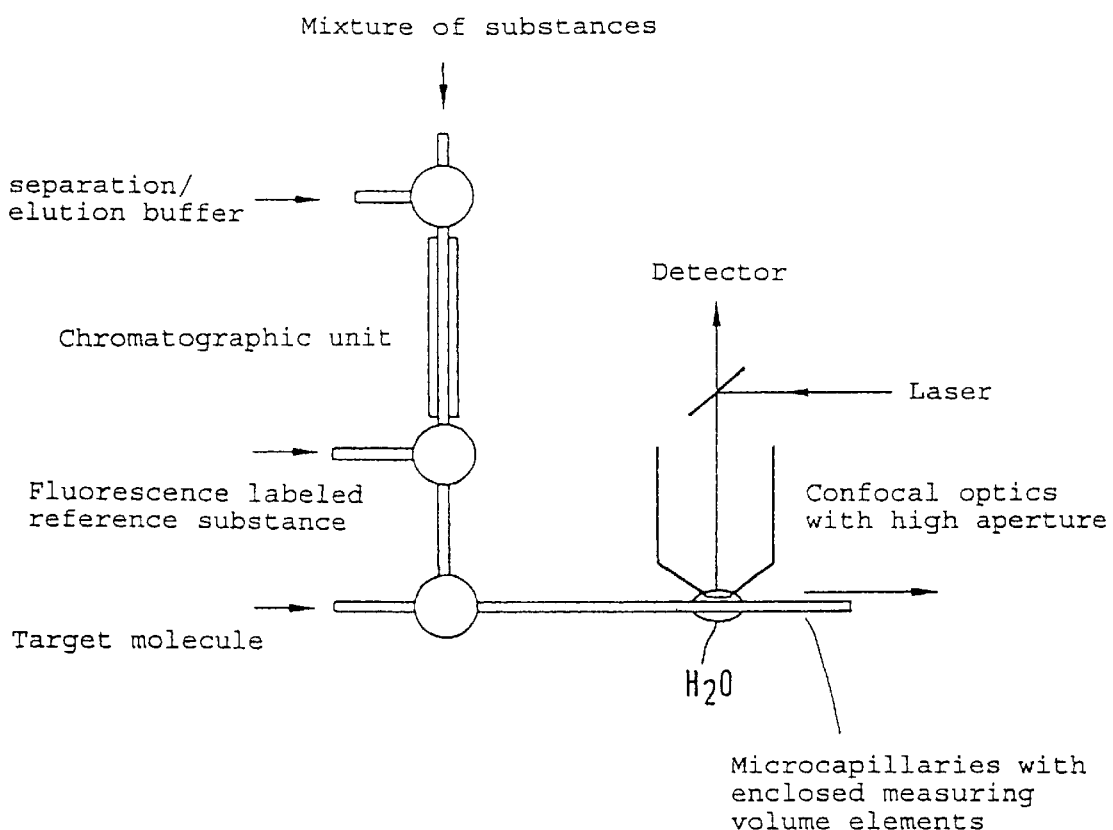
FIG. 9 is a schematic representation illustrating the analysis of mixtures following chromatographic separation.

The schematic FIG. 9 is explained hereinafter. According to the invention, complex mixtures of substances can be analyzed through coupling with a chromatographic separation. After chromatographic separation, a labeled reference molecule is added to the fractions continuously and at a fixed concentration, to which the specifically binding target molecule is also added at a fixed concentration. As described in FIG. 1, the respective concentrations are preferably chosen such that about 50% of the molecules involved form a complex, so possible interfering substances from the separated mixture can be detected with maximum sensitivity.

Thereafter, the combined samples pass the detection unit through a capillary flow tube. The fractions are analyzed for specifically shifting the considered binding equilibrium.

Synthetically produced mixtures such as, for instance, mixtures of diverse substituted or unsubstituted alkyl residues in alkylation reactions, when complex synthon mixtures are used, can also be analytically covered as described above. It is no longer necessary then to separate the compound formed from its reaction mixture and to characterize it after each reaction step.

In a preferred embodiment (FIG. 9), aliquots of the substance to be analyzed for interference are first added to the individual fractions before the mixture is contacted with a solution containing the receptor, in order that possible competition reactions can be measured. Alternatively, if a receptor is already occupied, a slow dissociation rate constant could colicate detection of a displacement reaction. Receptor displacements reactions which are slow allow for the measurement of the change with time, i.e. of $k_{diss}$.

32. Screening of Complex Mixtures for Biofunctional Interaction Properties With Concomitant, Rough Evaluation of Parameters for Physical Interaction With Target Molecules If a mixture of different substances is to be analyzed, according to the invention, for properties of interaction with target molecules, e.g. in LC/FCS coupling, upper or lower limits for binding constants allowing for corresponding quality evaluation of respective guide structures can be directly estimated. This shall be illustrated by the following example:

10 $\mu$g of a mixture of substances is applied onto a LC separation device containing 1000 substances in which the individual sought substance is contained only in an amount of 0.1%. This corresponds to an absolute amount of 1 ng. After separation of the fractions, this amount of substance is present in a volume of 5 $\mu$l. With an assumed average molecular weight of 200 Daltons, this means a concentration of $10^{-6}$ M. If the target molecule, e.g. a receptor, is added at a comparable concentration, then complex formation can be accomplished within a given period of time only if the reaction rate exceeds a given maximum value and the binding constant is $>10^6$.

The detection reaction can be coupled to a parallel HPLC/MS or GC/MS analysis in order to directly obtain structural data for the compounds identified as being active.

The small expenditure of substances of the analytical method according to the invention also allows for the use of the analytical method according to the invention in competition with different alternative methods of biosensor technology which can suffer from problems of signal drifting when used in on-line analyses. Instead of the chromatographic unit described above, a sample dispenser may be used.

DNA/RNA Probe Assays

When the potential detection sensitivity of the technique according to the invention is fully utilized, a specific problem arises in DNA or RNA probe technique. On a molecular level, the detection reaction according to the invention requires the formation of double-helical structures made of single strand structures which are at least partially complementary to each other, wherein the single strands involved may consist of DNA or RNA or mixtures of DNA and RNA fundamental structures which may bear chemical modifications, wherein said modifications in particular may pertain to the base structure, especially those which alter the luminophorous properties of the bases and/or those bearing substituents which have properties of specific binding to specific molecules or molecular complexes and/or are luminescent substituents.

The formation of double-helical structures, however, is a relatively slow reaction (hybridization, cot kinetics). In experimental practice, this means, for instance, that reassociation of genomic DNA from cells is a process which will last for weeks and months, depending on the experimental conditions, so that the experiment cannot actually be carried out completely. Only repetitive genomic segments, which may occur e.g. in a number of >100,000 per eukaryotic genome, can be rehybridized (Davidson & Wetmur).

An approximative formula which can very well be used in practice describes the reassociation of a denatured double strand fragment:

$$t_{1/2} = N \times \ln 2 / (3.5 \times 10^5 \times L \times c_0)$$

$t_{1/2}$ yields the half life of the reassociation in seconds at an ionic strength of 1 M at $T = T_m - 20$. L is the length of the probe fragment, N is the length of unit sequence, $c_0$ is the molar concentration of nucleotides, and $3.5 \times 10^5$ is an approximative value for the intrinsic rate constant of the association.

Since the reaction rate depends on the sum of the concentrations of the two reactants (+ and − strands), there are two possibilities in general to accelerate the reaction of reassociation. Since the excess component determines the rate, in conventional blot assay the probe is usually used in excess to subsequently separate the excess probe in washing steps. With the introduction of enzyme-based amplification reactions, such as PCR (polymerase chain reaction), it is also possible to amplify the target nucleic acid to be detected to such an extent that it will determine the reaction rate. However, if amplification reactions are intended to be dispensed with in the method according to the invention, or the detection is to be performed without troublesome separation of the probe component in a one-pot procedure, one or more process steps and procedures may be combined according to the invention.

The sensitivity of the detection of viral or bacterial pathogens in the gas phase (air germs) or in solutions or suspensions in small sample volumes, as are sufficient for the detection according to the invention, can be increased by using simple filtration steps. They can be extracted from large volumes through filters or filter systems and incorporated in small sample volumes. An alternative is concentration e.g. through coated magnetic particles.

For DNA/RNA analysis, probes with intercalating substituents can be employed. The use of those chromophorous ligands is especially preferred, whose fluorescence behavior changes or is enhanced during intercalation. Especially useful are substituents of the thiazole orange class. In the intercalated state, their fluorescence efficiency is about 1000 times larger than in the free state. Thus, it is possible to measure a specific complex formation through intercalation at a thousand-fold excess of non-dye-intercalating probe.

By using oligomeric or multimeric dyes linked to a probe, the sensitivity can be further enhanced by a factor of 10 to 100, since less individual events must be detected to produce the required signal.

Excess concentration of a double strand analyte is not necessarily desirable to accelerate the reaction. Thus, an undesirable displacement of already associated probe from the complex may result if a counter-strand of the analyte present in excess hybridizes with the complex further up or down.

According to the invention, this problem is solved by taking care that the excess of analyte be present only in the form of a polarity without a counter-strand, such as generated, for instance, by unsymmetrical priming in a PCR reaction, or by run-off production of specific RNA sequences by means of RNA polymerases as naturally occurring in cells or being generated in homogeneous amplification reactions such as 3SR.

The displacement reaction can also be prevented by intercalating substituents thermodynamically stabilizing the complexes (e.g. acridine dyes) or by initiating irreversible cross-linking (psoralen derivatives) (see patent application P 42 34 086.1).

If the use of a labeled probe in the range of $10^{-12}$ M is possible through optimization of the above discussed parameters according to the invention and hence an analyte (counter-strand) in the range of $10^{-14}$ is still detectable, then the reaction kinetics of reassociation (complex formation) becomes unacceptably slow. Using the approximative formula mentioned above, it can easily be calculated that a fragment of the length and unit length of 200 nucleotides would take about 23,000 minutes (16 days) to reassociate if 10 half lives should be waited out before the optical measurement by the method according to the invention.

By using a combination of organic solvents based on phenol and chaotropic salts such as thiocyanates or perchlorates, the reaction kinetics can be accelerated to about 100,000-fold (Kunkel et al.). Those methods have not proven successful in practice in filter assays. They can be combined, however, with the method according to the invention which is preferably performed in solution. In this way, not only the reaction rate of the example mentioned above is shifted into the range of seconds, but the solution at the same time prevents degradation processes by the action of e.g. ribonucleases on RNA analytes.

The method also allows for the differential detection of large vesicle complexes as are necessary for a differential diagnosis in lipid metabolism if distinction between different transport vesicles LDL, VLDL, and HDL is sought. Therefor, relatively complex electrophoretic methods must be employed to date the quantification of which is not easy. Dye-labeled vesicles can be distinguished according to the invention by mobility and/or rotational diffusion measurements. The vesicles may be stained with fluorescence labeled specific antibodies. Alternatively, fluorooporous label molecules can be specifically and permanently incorporated in the vesicle structures.

Functional Assays of in Vitro Translation Products

The use of the screening technology according to the invention is of particular importance for the analysis of replicative molecules in the form of proteins or peptides in combination with in vitro protein biosynthesis. In vitro protein biosynthesis avoids recombinant cellular systems. However, the effectivity of in vitro protein biosynthesis is so small that detection of the function of the synthesis product is not possible without expenditure. In average, no more than one peptide or protein molecule is produced from an mRNA molecule. The result can be even worse. The sensitivity of the method according to the invention, however, allows for determination of function since mRNAs must be used in the synthesis mixture only in the $\mu M$ concentration range and below and a small sample volume is sufficient for the analysis.

Determination of Molecular Size Distributions

In the analysis of polymeric chemistry, it is important to determine polymer distributions. This can be achieved in a simple way by using the method according to the invention which hence represents an alternative to ultracentrifugation methods and physical flow methods. Herein, the inherent fluorescence of an oligomer or polymer may be used or association or coupling of luminophorous ligands can be observed.

In situ hybridization is a method in which the specific double strand formation between a labeled Nucleic acid probe and a complementary target nucleic acid is performed in a geometrically fixed arrangement of the object to be analyzed. The object to be analyzed can be a surface fixed preparation of molecules or molecular complexes. Examples include preparations of chromosomes, transcription complexes, or translation complexes. In routine analysis, surface fixed tissue slices or cells from cell cultures are often important.

Dynamic Laser Correlation Spectroscopy

Due to its sensitivity, the method according to the invention allows for the localization even of single hybridized or, in the case of ligands other than nucleic acids, complexed ligands which are coupled to a fluorescence label. The advantage of the method according to the invention is based on the high sensitivity of the detection of single molecules. This allows for direct analyses where otherwise the use of an enzyme-based amplification reaction would be necessary or high local concentration of target molecules would be required, such as in the case of polytene chromosomes. The use of double or multiple labeling in the method according to the invention whereby the relative position of interesting structures can be determined is also claimed.

Figure 10:
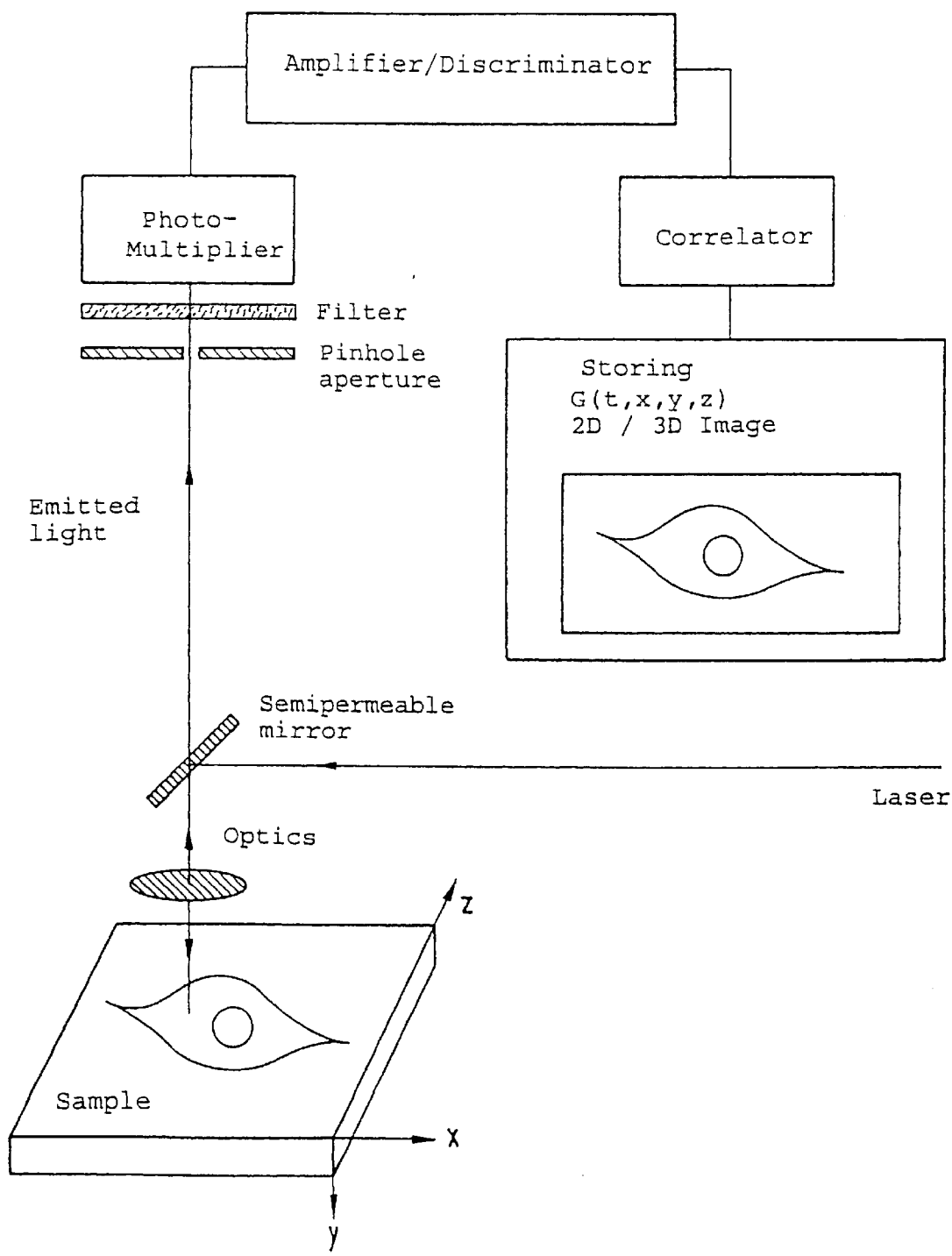
FIG. 10 is a schematic representation illustrating a laser correlation microscope.

The method according to the invention with confocal imaging of smallest volume elements by using a pinhole aperture for the analysis of dynamic processes can be used, according to the invention, in combination with the corresponding method used in a laser scanning microscopelin order to obtain a high spatial resolution of structures. Whereas with the laser scanning microscope fluorescence intensity alone is used as a measuring quantity, the "laser correlation microscope" according to the invention employs the correlation function and the dynamic contents thereof in the measuring element defined by the space coordinates (x,y,z) which is imaged two- or three-dimensionally (FIG. 10). In this way, two-dimensional (cross section) or three-dimensional images of the dynamics of a labeled molecule (rotational, translational diffusion, chemical kinetics) e.g. in a cell or in another biological object can be depicted.

The schematic FIG. 10 is explained hereinafter. The organization in principle of the optics according to the invention is depicted. The sample is contained in a sample holder which can be shifted within a given defined screen by a two- or three-dimensionally controllable piezo drive. The respective related volume elements are analyzed for dynamic processes and as a whole assembled into a two-dimensional (cross section) or three-dimensional image by a computer.

33. Determination of Epidemiologically Conserved Gene Segments

Through determination of the dissociation rates of hybrid double strands, homology estimations can be performed in analogy to the determinations of dissociation rate constants described above. This is of great importance in epidemiological analysis of diverging pathogens as in the HI virus. To develop diagnostic probes and to evaluate their reliability, several gene segments of different origin must be examined for those parameters (see FIG. 22).

Method for Simultaneous Testing of a Plurality of Mutations on a Target Genome

Figure 23:
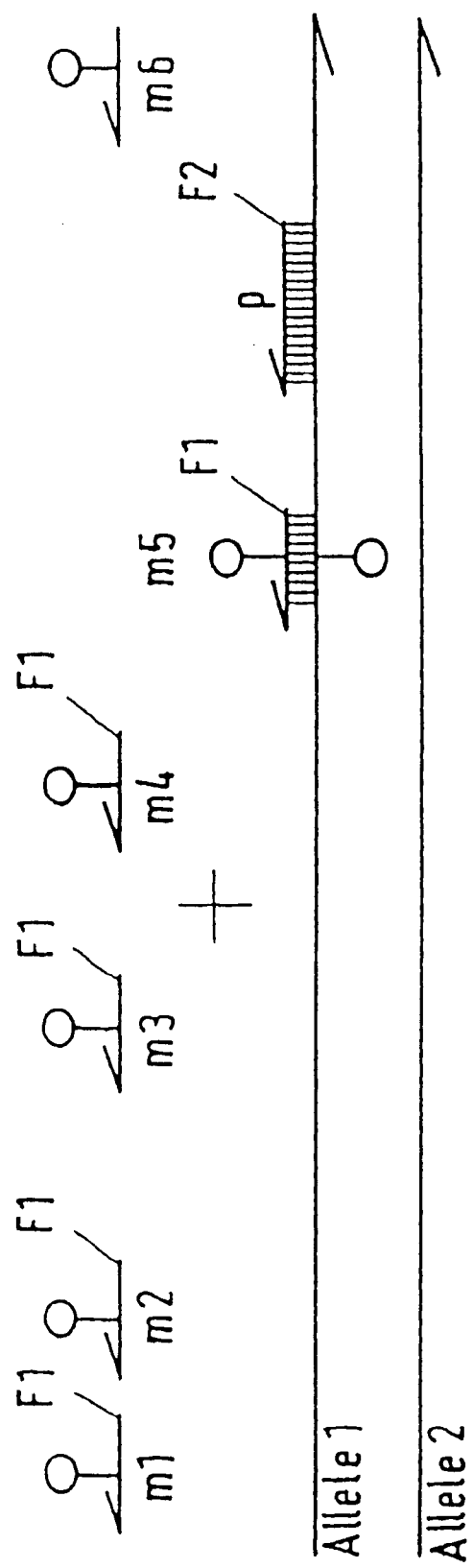
FIG. 23 is a schematic representation illustrating a method performed according to the invention.

In the analysis of genetic diseases, the problem frequently arises to assay for the presence of a great number of possible mutations simultaneously. This is the case especially with dominant genetic diseases or X chromosome encoded diseases. With recessive diseases, it is often important to evaluate whether a particular point mutation occurs only on one allele or on both alleles simultaneously (see cystic fibrosis with more than 30 mutations described to date). The procedure according to the invention allows for simultaneous analysis for different mutations in one sample (FIG. 23).

Detection of Single Bacteria Through the Binding Specificities of Surface-expressing Bacteria For a great number of important applications of modern biotechnological research, it would be extremely advantageous and efficient, if in a method detection of a single bacterium or virus with functional surface proteins could take place instead of the detection of a functional biomolecule in a given sample volume. The critical advantage lies in the coupling, which is often very interesting, of a phenotypical expression product, e.g. a natural or recombinant surface protein, to its genetic template.

The genome of microorganisms comprises about $10^7$ nucleotides. By shotgun expression, subgenic fragments of an average length of 100 amino acids can be expressed by methods known per se. Considering the variation of reading frame (factor 3) and an assumed non-coding complementary strand, $10^8$ recombinant bacterial clones contain each segment about 100-fold. $10^8$ recombinant bacterial clones which are contained in 1 ml of a suspension of 10D can be examined individually for e.g. their properties of binding to IgE from an allergically responding patient by the method according to the invention in about 24 hours. The bacteria correspondingly characterized will have to be singled out or at least to be highly enriched, and to be biologically expanded, or the corresponding genome segment will have to be amplified and characterized by enzyme-based amplification methods.

Such problems are connected with methods for the evolutive optimization of peptides and/or proteins by using mutagenesis methods and selection methods such as described, for instance, in WO92/18645. Within 24 hours, about $10^9$ bacteria can be screened by their properties of binding to specific dye-labeled substances for the presence of a bacterium expressing a surface protein/peptide having the ability to interact with the target molecule at a given concentration. The corresponding bacterium can be cloned from such a reaction mixture by conventional methods.

Another important application spectrum results from the so-called genome project for, the functional mapping of gene segments from genomic libraries, cDNA libraries or libraries of subgenic structural elements (Shape Space). In this way, the functions of genomic and/or subgenomic segments from extended collectives, e.g. their behavior of binding to target molecules, can be determined.

The use of the methodology described of functional assignment of genetically encoded peptide segments will become very important especially in allergologic research. The assignment of immuno-dominant epitopes on allergens (e.g. Aspergillus, milk protein, α-amylase) is of extraordinary importance and represents a problem that has been difficult to solve to date. Typical problems occurring in practice are:

The determination of the IgE binding molecules in a mixture of substances which is usually ill-characterized. For instance, answering to the question which is important which contents of soya lecithin are immunogen: the pure substance alone, the pure substance in its interaction with impurities of the preparation, or the interaction with structures of the host organism. According to the invention, the different substances in the mixture can be differentiated with labeled IgE from patients.

By expression of subgenic gene segments, the immunodominant epitopes can be localized and characterized by the method mentioned above. With these results, evolutively analogue functional molecules lacking the corresponding immunodominant regions, e.g. a less immunogenic α-amylase, can be generated by the methods described in WO92/18645, and the specific epitopes can be prepared simply by standard methods of genetic engineering and be used as pure test reagents or for desensibilization.

The Device

Figure 14:
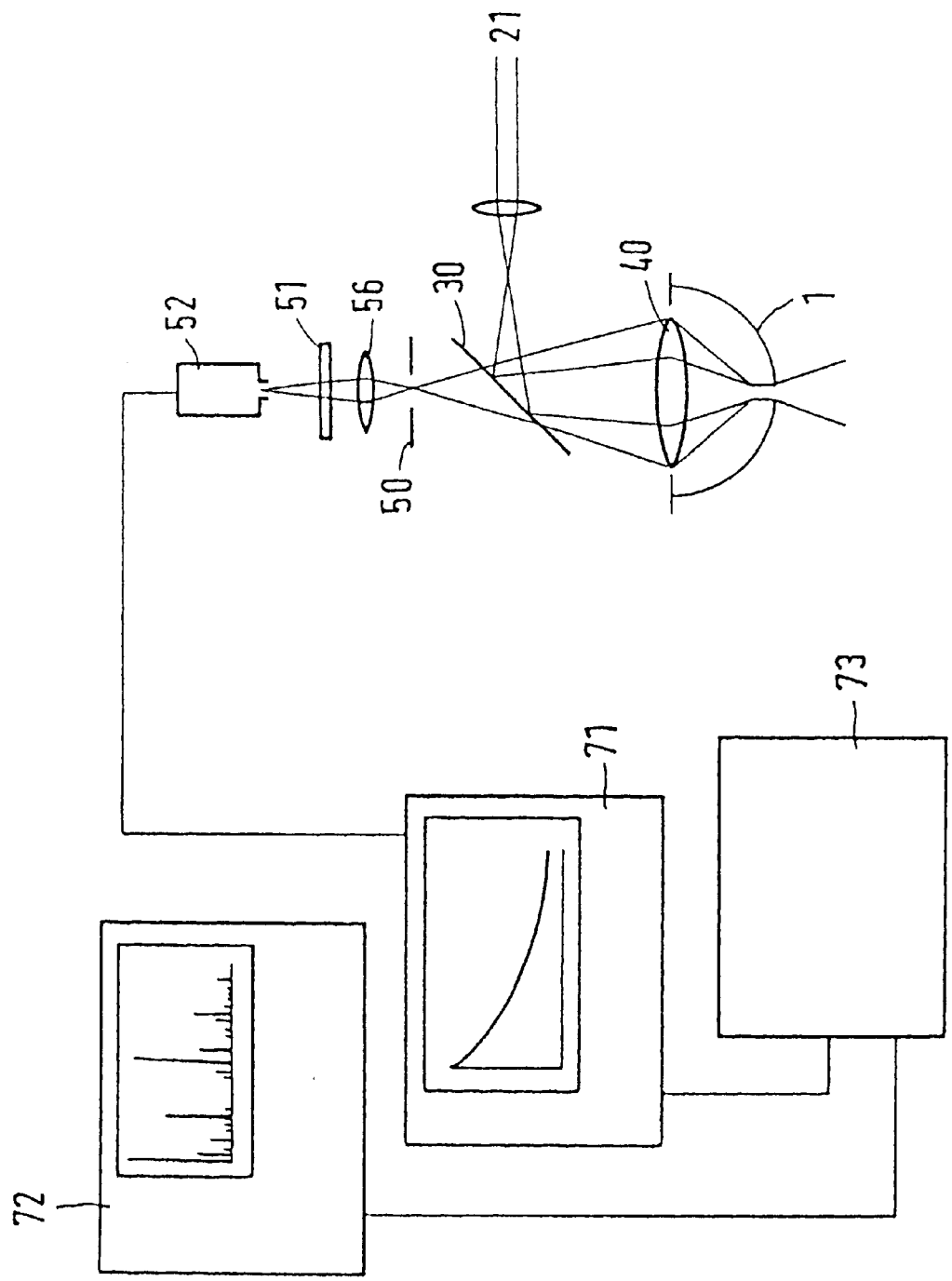
FIG. 14 is a schematic representation illustrating a measuring array device including a prefocused laser beam.

The measuring array is a device which is particularly useful for performing the method according to the invention due to the diffraction-limiting focusing of a laser beam in the arrangement described below. According to FIG. 14, the device is characterized by a prefocused laser beam. By introducing a combination of focusing lens and exchangeable microscope optics with constant imaging distance, the diameter of the prefocused laser beam can be varied. After deflection by a dichroitic mirror, the prefocused laser beam is imaged on the sample volume which is present, for instance, on a carrier or in a hanging drop 1 by means of air or water immersion optics with or without a cover glass. Usually, the fluorescence emission is taken up and imaged by the immersion optics in an angle of 180° with respect to the direction of the exciting light. In the object plane 25, there is a pinhole aperture which is then imaged in an appropriate scale on a semiconductor detector element (avalanche photodiode) after passing appropriate cut-off or interference filters. The appropriate scale results from adjusting imaging of the sample to the dimension of the photodiode. Preferably, the photodiodes are realized relatively small, as in the range of 100 μm, so that they can "replace" pinhole apertures in terms of a confocal detector. In a special embodiment of the device according to the invention, the diodes can also be arranged in ensembles in the form of detector arrays.

Imaging of the pinhole aperture 50 can take place using a beam splitter 60 on, for instance, 2 detector elements 53, 54 that are optimized for different emission wavelengths. Instead of the pinhole aperture, one or more semiconductor detector elements (an array), for example, can be placed in the image plane.

In a preferred embodiment, the device according to the invention, which can be divided mentally into a unit for the generation of diffraction-limiting focusing of a laser beam and an observing unit, has the following construction elements. The appliance 20 for prefocusing a laser beam 21 further contains a dichroitic mirror 30 in the beam path of the laser to deflect the laser beam 21. The laser beam generated by diffraction-limiting focusing is imaged after deflection by the dichroitic mirror 30 by means of another lens 40 into the sample which is positioned, for instance, on a carrier or is present in the form of a hanging drop 1.

Optionally, the observing unit has filter appliances 51, photon counter appliances 52, a correlation appliance 71 and/or a multichannel scaler appliance 72. The measuring signal can optionally be processed and/or evaluated in a computer assisted way.

Figure 15:
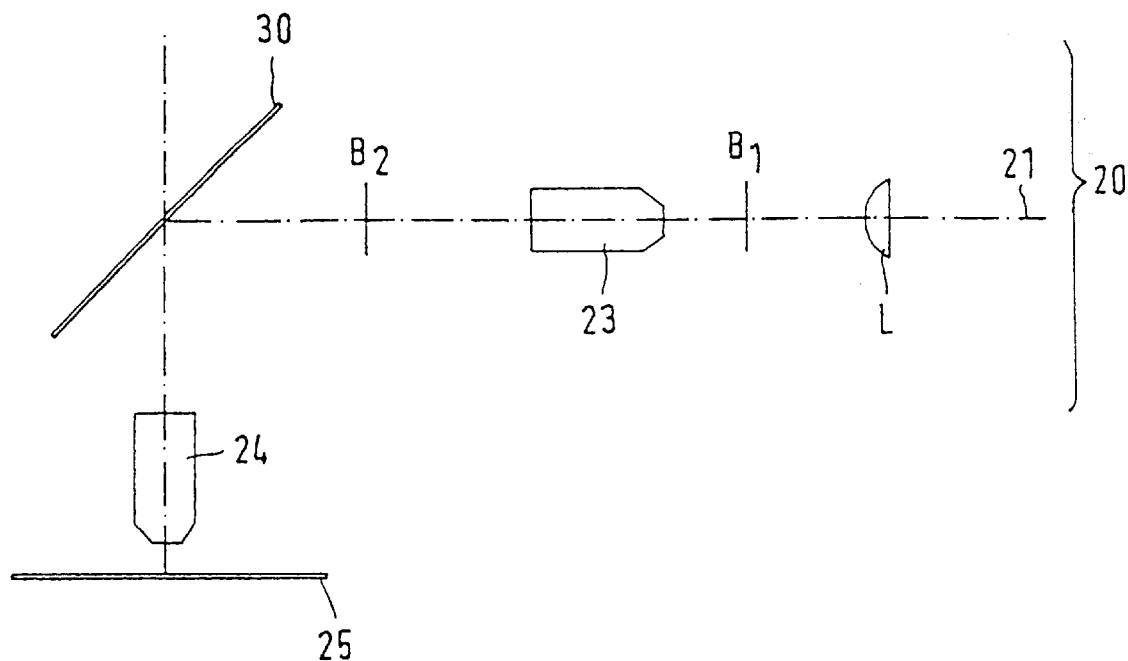
FIG. 15 is a schematic representation illustrating a prefocusing appliance for a laser beam.

FIG. 15 shows schematically the prefocusing appliance 20 for prefocusing the laser beam 21. By the lens L 22 and an array 23 corresponding to microscope optics the collineated laser beam 21 is imaged on the image plane $B_1$ through the lens 22. The array 23 images the laser beam on image plane $B_2$ as a first image. Preferably, the array 23 is provided with an exchangeable arrangement of lenses, for instance in the form of a microscope nose piece. The diameter of the prefocused laser beam 21 can be varied therewith.

Figure 16:
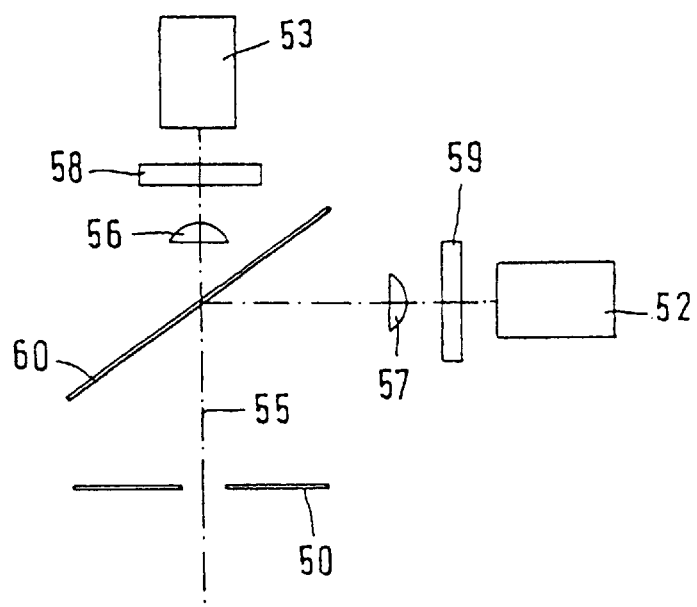
FIG. 16 is a schematic representation illustrating the arrangement of a preferred embodiment of the device according to the invention.

In a preferred embodiment of the device according to the invention, the detection unit consists of two detectors 52 and 54 and has a beam splitter 60 partitioning the light 55 emitted from the sample to the detectors 53 and 54. This arrangement is schematically shown in FIG. 16. It is advantageous therein, that the emitted light 55 from the sample 1 passes imaging lenses 56, 57 and filter elements 58, 59 prior to entering each of the detectors 53 or 54. In particular, it is advantageous that the detectors 53 and 54 each can detect light of different wavelengths. This can be achieved by selecting suitable filters.

If the detector elements are placed in the image plane in the form of a detector array, the use of the pinhole aperture 50 can be dispensed with. The detector elements should then preferably have a size of <100 μm. Another preferred embodiment of the device according to the invention has a pinhole 50 in the beam path 55.

Figure 25:
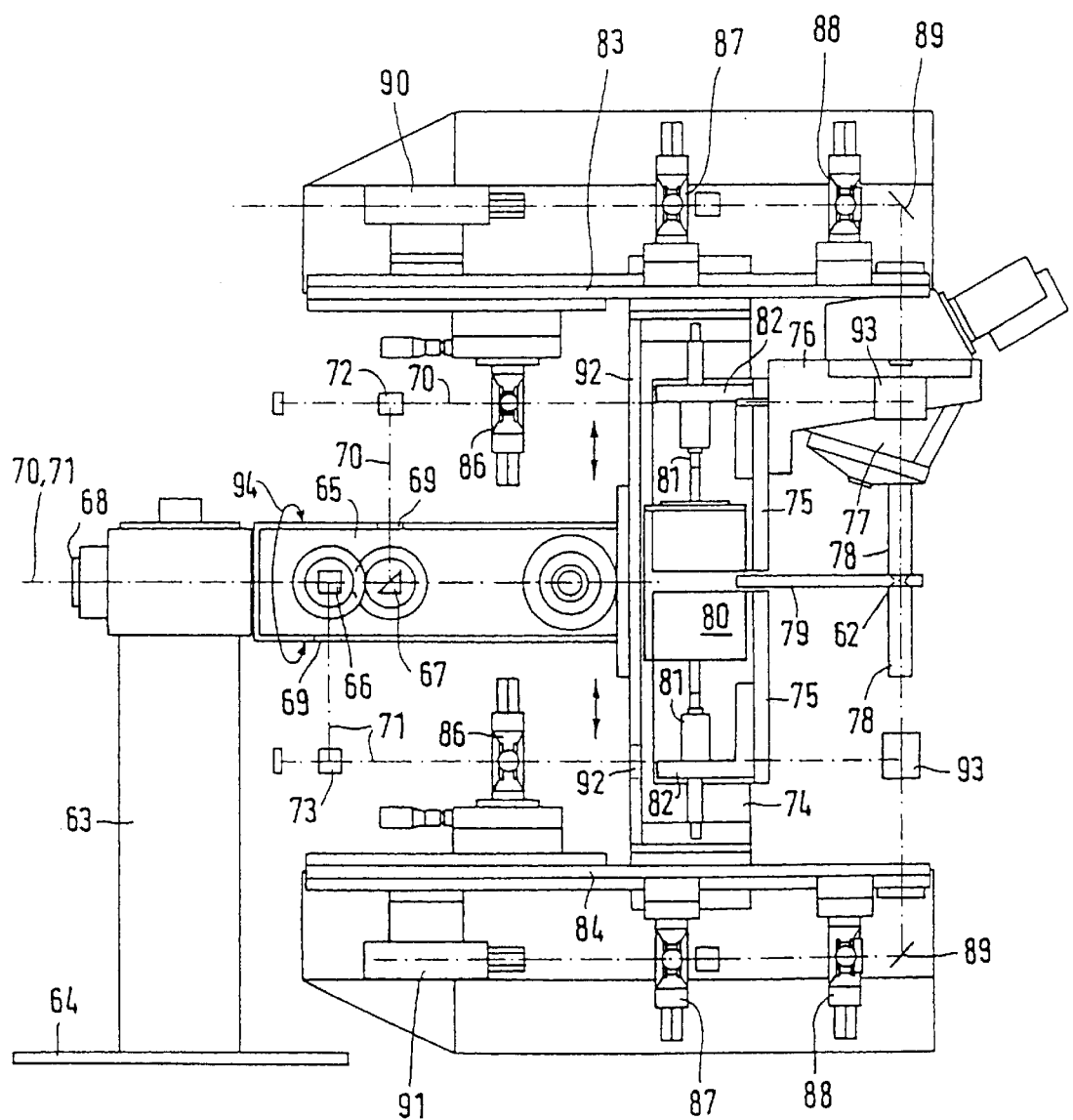
FIG. 25 is a side view of a double microscope.

In FIG. 25, a double microscope as used for investigating a measuring compartment (sketched out at 62) is depicted in side view. The microscope has a vertical support 63 (rectangular tube) provided with a sole plate 64. On the upper end of the support 63, a central supporting arm 65 is pivoted to rotate around a horizontal axis. The central supporting arm 65 is devised hollow and provided inside with optical elements, such as a beam splitter 66 and a 45° reflecting mirror 67. The bearing axis 68 of the supporting arm 65 is devised hollow, wherein two superimposed laser beams are radiated axially into the supporting arm 56 alongside the ideal rotation axis and there impinge on the beam splitter 66 and on the mirror 67 (broad roof prism) in the beam path behind. Through the beam splitter 66 and the mirror 67, the two superimposed laser beams are guided out of the supporting arm 65 on two opposing sides; at these sites, the supporting arm is provided with openings 69 (glass cover plate).

The two laser beams 70, 71 leaving the supporting arm 65 impinge on the beam splitters 72, 73 which deflect laser beams 70, 71 so that their direction is parallel to the axial direction of supporting arm 65.

At the free end of supporting arm 65, a supporting arm 74 is attached which is arranged in such a way relative to supporting arm 65 that both arms together form a T-shaped configuration. At the front side of supporting arm 74 facing away from support 63 there are guiding appliances 75 for guiding longitudinal shift of body parts 76 which in turn bear an objective nose piece 77 with the objective lens 78. The relative alignment of the two nose pieces 77 is such that the objective lenses 78 are facing one another and are lying on a common optical axis, while between the two objective lenses 78 the specimen stage 79 is located which in turn is held by supporting arm 74. Inside the supporting arm 74 there is a double spindle drive 80 with two spindles 81 having opposite threads. The spindles 81 are in thread-connection with arms, 82 projecting into supporting arm 74 and connected to the body parts 76. Thus, when the double spindle drive 88 is driven, the two body parts 76 are moving, depending of the driving direction, towards one another or away from one another, so that the focuses of the two objective lenses can be joined.

A double guiding system is connected with each of the two displaceable body parts 76. Each of those double guiding systems is embodied in form of a twin fish tail slide rail 83, 84. These slide rails 83, 84 are arranged facing the two ends of supporting arm 74 at the faces and are shifted along with the body parts 76. The two slide rails 83, 84 project beyond supporting arm 74 on both sides (side of glass slide and of connection with supporting arm 65) while being parallel to the supporting arm 65. The inner sides that are facing each other are provided with optical elements 85, 86 for prefocusing the laser light coming from the semi-transparent mirrors or beam splitters 72, 73. On the sides of the two slide rails 83, 84 that are facing away from each other, more optical elements (lenses, apertures, filters and the like) are located in order to affect the light coming from the measuring compartment. 88 are the pinholes and 89 designates biconvex lenses for imaging the pinhole apertures on the detectors to detect the fluorescence radiation. Furthermore, at the outer sides of slide rails 83, 84 that are facing away from each other, there are reflecting mirrors 89 being aligned in an angle of 45° and deflecting the light coming from the measuring compartment 62 towards the optical elements 87, 88. In addition, the actual detectors 90, 91 (avalanche photodiodes) which convert to electric signals the information from the received laser light required for further processing in cross correlation are located on those sides of the slide rails 83, 84.

The operation mode of the double microscope shown in FIG. 25 is as follows. Through the bearing axis 68, the two superimposed laser beams (70, 71) of different wavelengths are entering supporting arm 65 where one of the laser beams 71 is reflected by the beam-splitter element 66 by 90° to one side and the other laser beam 70 is reflected by 90° in the opposite direction via the mirror 67 after having penetrated beam splitter 66. The laser beams 70, 71 leaving openings 69 of supporting arm 65 impinge on the beam splitters or semitransparent mirrors 72, 73, from which they pass the optical elements 86. Thereafter, the laser beams penetrate supporting arm 74, to which end the latter is provided with elongated holes 92 on its sides facing the support 63 and the specimen stage 79 (in FIG. 25, only the elongated holes 92 facing support 63 are depicted). Then, the laser beams 70, 71 further run through the body parts 76 where they impinge on equally semitransparent mirrors 93 from where they run through the nose pieces 77 and the objective lenses 78 to impinge on the measuring compartment 62. The light reflected by the measuring compartment 62 penetrates the semitransparent mirrors 93 without deflection and is sent to the optical elements 87, 88 at the outer sides of slide rails 83, 84 by the reflecting mirrors 89. Thereafter, it impinges on detectors 90, 91.

In order to be able to adjust, depending on the objective lenses 78 used which are identical, the focuses of those lenses onto the measuring compartment 62, the body parts 76 and along with them the slide rails 83, 84 can be shifted, as has been set forth above. Since the semitransparent mirrors 72, 73 are held on the sides of the slide rails 83, 84 that face each other, as are the optical elements 86, the distance of the semitransparent mirrors 72, 73 from the reflecting mirror 67 and the semitransparent mirror (beam splitter 66) changes when the body parts 76 and the slide rails 83, 84 are shifted. In the regions following the semi-transparent mirrors 72, 73, where the laser beams 70, 71 are running parallel to the supporting arm 65, the distance of those beams from said mirrors is changed. According to this, their relative position within the elongated holes 92 of supporting arm 74 changes. From this it becomes apparent that all optics which are located outside the central support-ing arm 65 are moved when the focuses of the two identical objective lenses 78 are changed while the two possible directions of movement coincide with the directions of the laser beams 70, 71 leaving the central supporting arm 65.

The entire double microscope has an extremely compact construction. All elements are arranged such that the weights are "essentially uniformly" distributed. The operator of the double microscope facing the specimen stage 79 is not hindered by optical elements and appliances of the micro-scope in his working area. The central supporting arm 65 and hence the total of the optical appliances of the double microscope can be rotated (see arrow 94). The central supporting arm is held at the support 63 by two bearings which are tensioned axially to one another so that no bending will occur. The position of one of the two objective lenses 78 can be positioned with extreme accuracy by a piezoelectrically or otherwise driven and working adjusting element (not shown) in order to be able to balance an offset of the common focus of the two objective lenses 78 from the position where the measuring compartment 62 is located on the specimen stage 79.

In addition to the optical elements which are described and depicted herein, such as lenses, filters, reflecting mirrors, semitransparent mirrors, additional optical elements can be positioned in the beam path of the laser beams 70, 71, if this is required or recommended by the examinations to be performed.

Figure 17A:
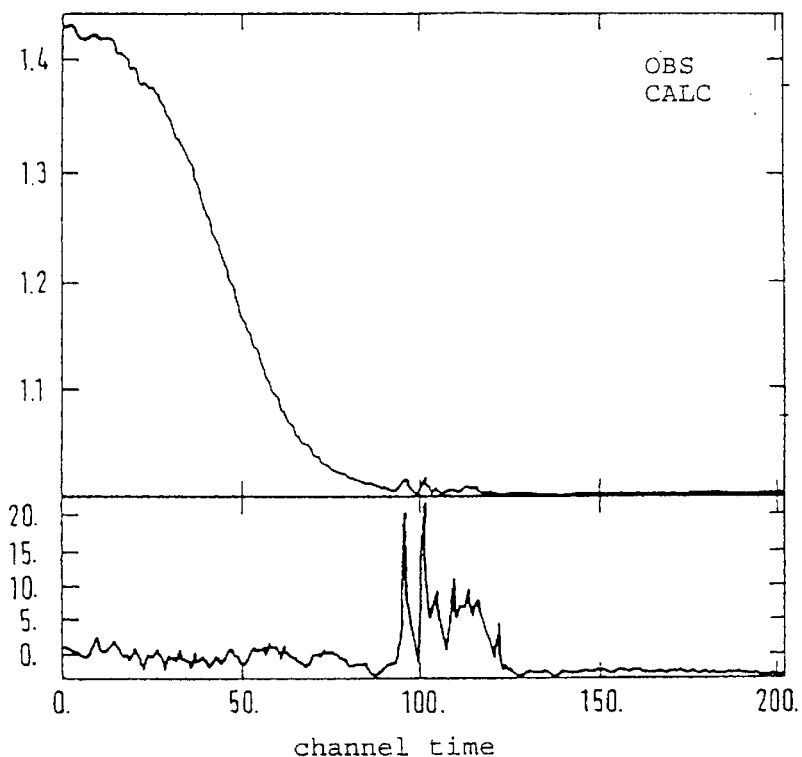
FIGS. 17a, 17b, 18a, 18b, and 18c are graphs of measurement results.
Figure 17B:
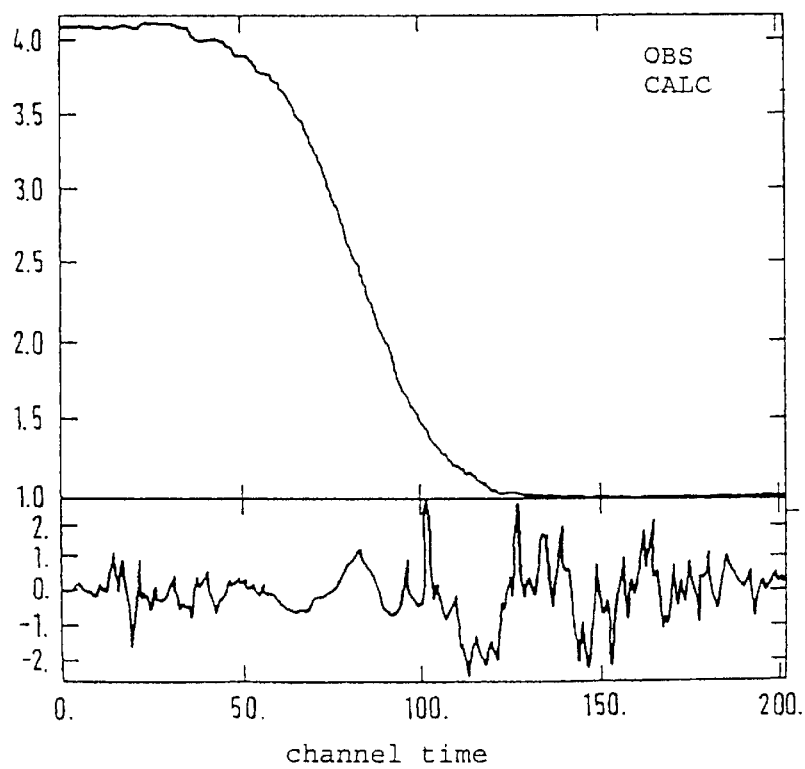

FIG. 17 shows a deoxyribonucleic acid labeled with rhodamine. The ordinate exhibits the normalized intensity correlation function. The abscissa is a logarithmic time axis. The concentration are given in terms of labeled molecules per volume element ($2\times10^{-16}$ l). FIG. 17a) shows the mononucleotide uracil, two molecules per volume unit, whose diffusion time is 0.067 milliseconds. FIG. 17b) shows a DNA with 500 base pairs corresponding to 0.3 molecules per volume unit having a diffusion time of 1.8 milliseconds.

Figure 18A:
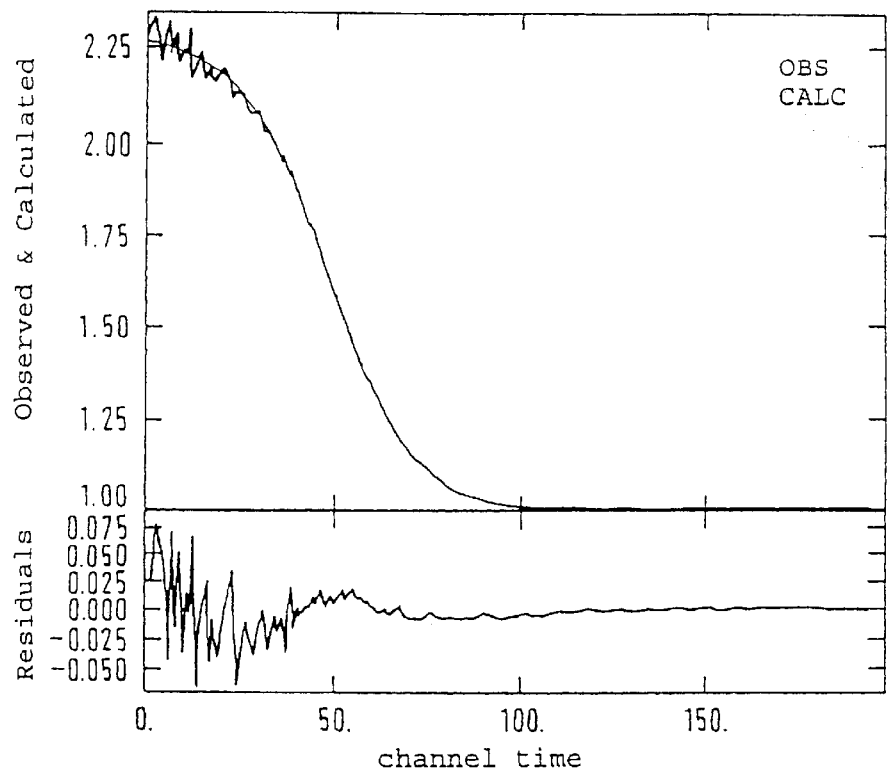

FIG. 18 shows the interaction of a fluorescence labeled receptor ligand with cell-bound receptors (β-adrenergic receptors) in human lymphocytes. The axes of the system of coordinates are as described in FIG. 17 above. FIG. 18a) shows the labeled ligand in BSS, 10.7 molecules per volume unit with a diffusion time of 1.1 milliseconds.

Figure 18B:
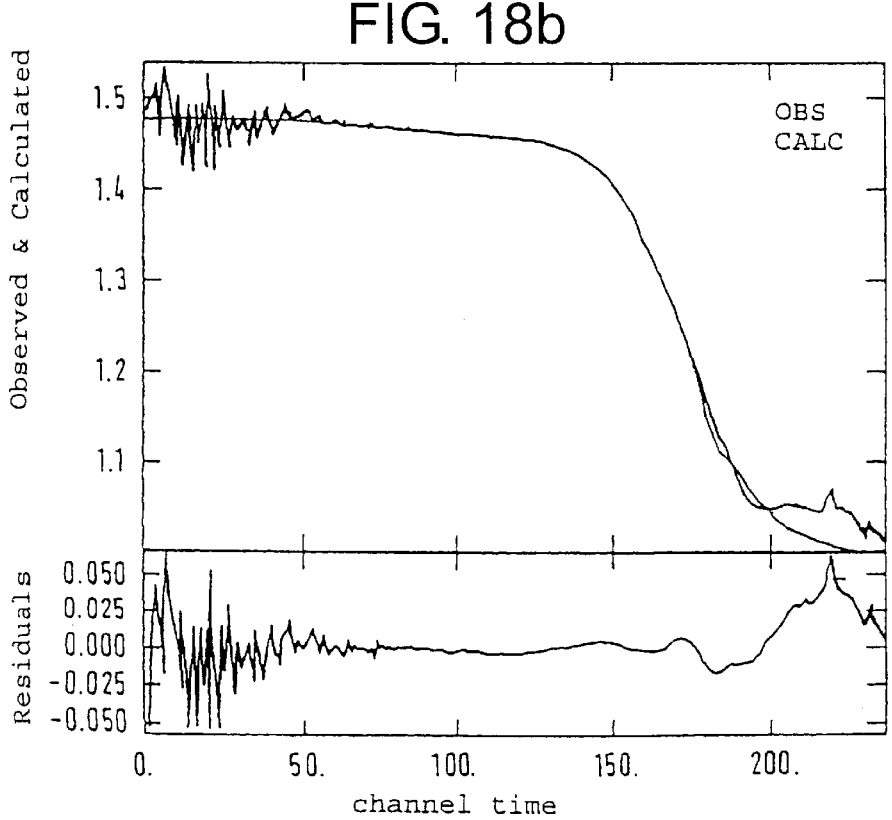

FIG. 18b) shows the lymphocyte receptors labeled with ligand in BSS, 72 molecules per volume unit, diffusion time 13 sec.

Figure 18C:
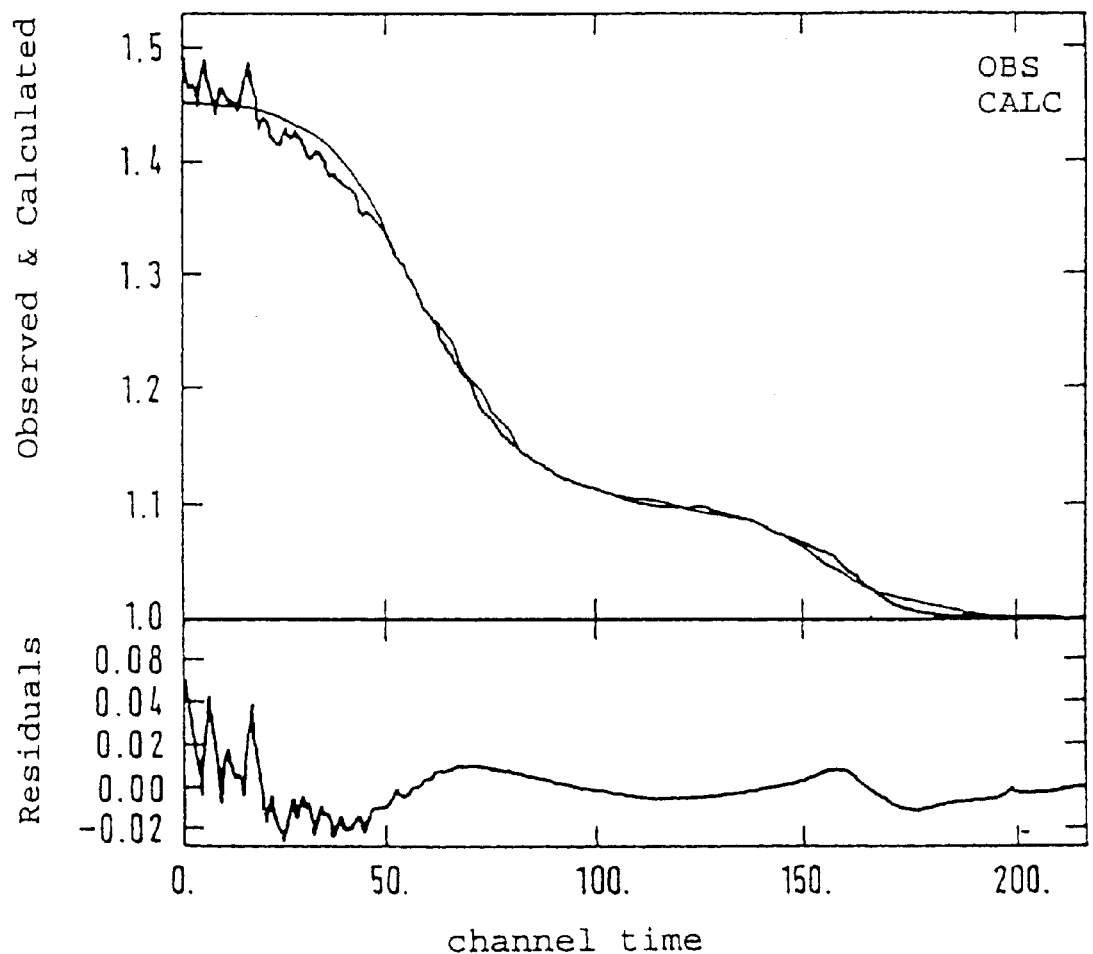

FIG. 18c) shows the situation of 76% free ligands and 24% ligands bound to the lymphocyte receptor.

Since fluorescence correlation functions can be obtained within 10–100 ms, 1000 picture elements can be coded within 10 to 100 seconds. In particular, each picture element of the method according to the invention corresponds to one Poisson space element typically having a radius of 0.1–1 μm and a length of 1–3 μm. The correlation function is calculated in each picture element for a given period of time and stored along with the respective coordinate x,y,z. Thereafter, the preparation is preferably shifted by a piezo drive to the new coordinate point, and so forth. Instead of shifting the preparation, the laser beam, for instance, can also be shifted within given limits by a suitable mirror appliance (see FIG. 9). The dynamic picture elements are then assembled to an image in the computer.

FIG. 6 describes the preferred arrangement of the optical detection unit with an electric molecular trap with respect to the sample volume and the measuring volume. One or two detectors (detectors 1/2) detect the emitted fluorescence signals from the measuring volume element which are also imaged confocally through one or two optical units as described in the text. The aqueous sample is either in direct contact with the surface of the emergence lens or is separated from the objective by a thin sheet as depicted in FIG. 3.

The sample is held between at least two capillaries with an inside diameter of the capillary end of about 1 μm. In the case of functioning as molecular traps for ionic molecules, the capillaries are coated with a conducting surface layer, preferably gold on a chromium priming to which a rectified or an alternating field can be applied. Controlling of the field is preferably done by a computer which is interfaced with the optical detection unit and can regulate the fields in a defined manner when an interesting molecule is entering.

FIG. 3 describes a preferred embodiment of the arrangement according to the invention for screening large numbers of mutants for particular fitness parameters. Samples can be examined using an optical detection unit according to FIG. 6. The samples are present in the form of droplets under a sheet-like surface which in turn is preferably in contact with the objective in terms of water immersion. The sheet can bear certain coatings allowing for selective binding of molecules from the respective samples to their surface. The samples can be regularly deposited at defined positions, e.g. when using a microdispensing system, or in random distribution. To prevent evaporating of the solvent from the samples the droplets may be surrounded by a protecting matrix, e.g. polymer structures or oil.

FIG. 7 schematically shows FCS tagging of selected genotypes. If particular samples correspond to fitness parameters preselected according to FIG. 3, access to the respective volume segments can be facilitated by the surface being provided with a photoactivable coating, which marks the position, e.g. optically, and allows for subsequent access to the sample.

Access to a selected volume segment or to molecules contained therein, such as coding nucleic acids, as shown-schematically in FIG. 8, can also be achieved by photoactivating soluble reactants in the volume element e.g. to react with a nucleic acid. Nucleic acids thus labeled can be subsequently isolated in a relatively simple way in order to subject them to further reactions, for example, a PCR reaction.

FIG. 11 shows a selection of possible assays according to the invention. "Ag" stands for antigen, but refers to the analyte in general terms, such as e.g. nucleic acid molecules for detection in double strand structures as well.

"Ak" stands for antibody but refers in general terms to a specific test reagent for an analyte, such as antibody fragments, binding domains, or nucleic acids complementary to an analyte.

"F" stands for a luminescence dye, in particular a fluorescence dye.

(A) Specific complexing, according to the invention, of an analyte "Ag" by a fluorescence labeled test reagent wherein the fluorescence labeled test reagent in a complexed form is distinguished, according to the invention, from its free form. This constellation allows for an excess of up to 1000-fold with respect to the analyte.

(B) Same as (A), however, the binding of a second test reagent added in excess in an unlabeled form is used to increase too small a difference in the sizes of the complex and the uncomplexed labeled test reagent.

(C) Competitive RIA-analogous assay with a smaller than equivalent amount of test reagent and addition of fluorescence labeled competitor analyte.

(D) Assay with large excess of test reagent, wherein at least two different test reagents are employed whose dye labels indicate specific complex formation through energy transfer.

(E) Same as (D), wherein the different dyes are detected independantly according to the invention and the formation of a common complex is determined by time correlation of the different optical signals.

FIG. 19 schematically describes how the dissociation behavior of complexes from n receptor molecules in n reaction mixtures and with dye-labeled ligand can present itself in parallel experiments. In defined time intervals, several reaction mixtures are repeatedly analyzed. At the beginning, excess of an unlabeled ligand is added to the mixture so that any dissociated complex is converted again into a complex with unlabeled ligand. From the courses of curves 1,3,n individual dissociation rate constants can be estimated, the courses of curves 2 and n–1 reveal two distinguishable dissociation processes and indicate distinguishable receptors.

FIG. 20 shows different embodiments of the electric trap according to the invention. (a) a,b,c,d represent quadrupolar electrodes (metal coated Neher capillaries or metal vapor deposited electrodes on microstructures on flat sample carriers (silicone, glass and other base materials)); e,f in the case of sextupole electrodes (e.g. as metal vapor deposited emergence lens of one or two objectives). Adjustment is done by x,y,z adjustment. (b) Use of flat carriers with etched electrode channels or LIGA technique prepared forms through which the motion of charged molecules in the electric field can be controlled. The bottom plates for e and f can be objectives coated as sextupole electrodes or metal vapor deposited coverings. (c) Use of (b) in combination with a sample dispenser system consisting of a capillary made of mineral materials (e.g. glass, silicon, etc., or plastics such as Teflon to prevent electroosmotic capillary effects) for large volume sample reception with an electrode at the capillary end (about ±0–100 V) and with a collecting electrode at earth potential (0 V).

FIG. 21 illustrates the possibility of detection of charged molecules by means of electric traps. (a) If target molecules are present within the quadirupole or sextupole field, the molecules can be set into forced motion by a random alternating field over the electrodes a,b,c,d. They thus become countable according to the invention. (b) The position of a molecule within the trap is recognized by a multielement detector. By active feedback the quadrupole/sextupole field is adjusted such that the molecule gets fixed in its position within a defined area/volume element.

Figure 22:
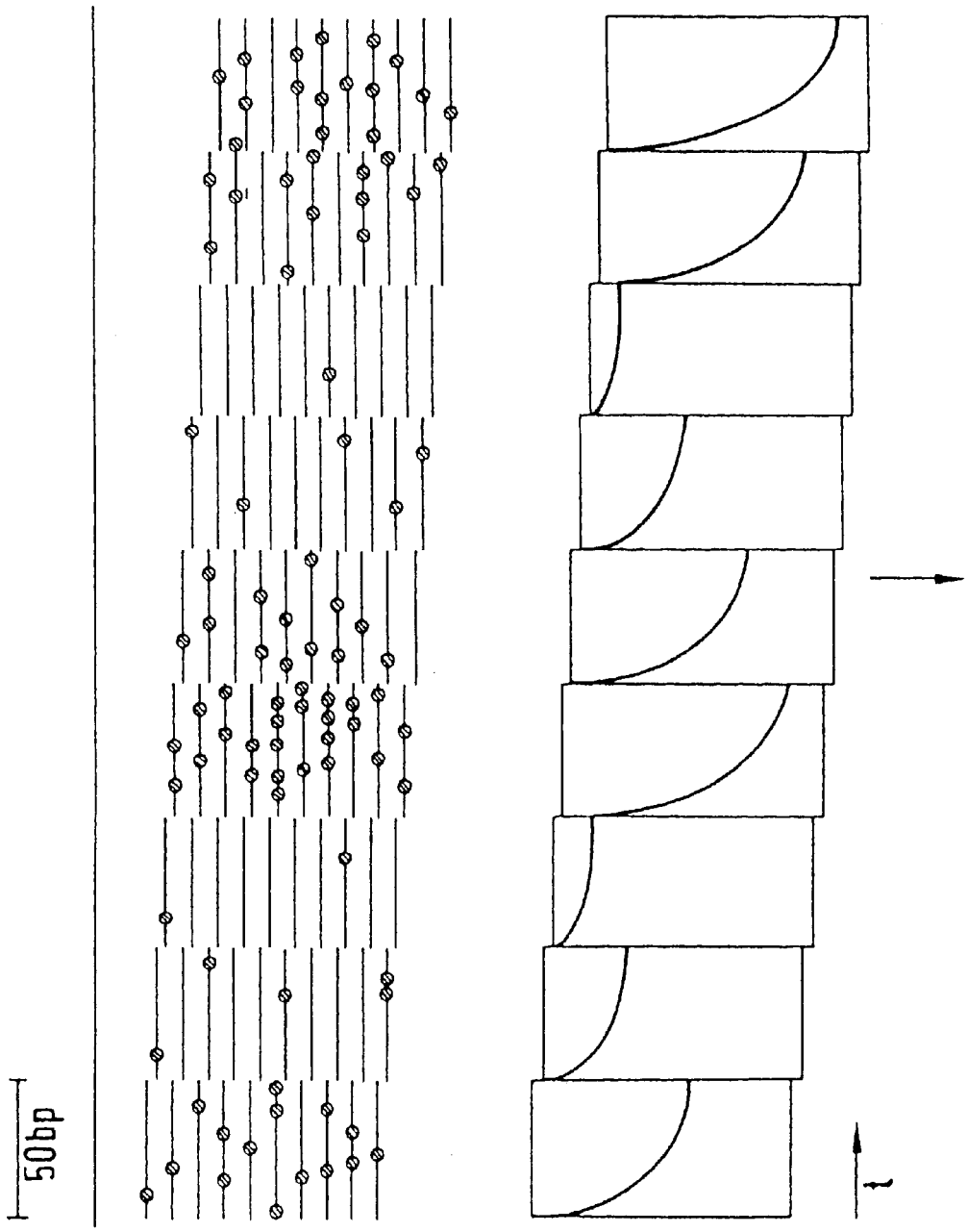
FIG. 22 is a schematic representation illustrating analysis of a displacement experiment.

FIG. 22 schematically shows analysis for epidemiologically conserved gene segments on a virus genome. A DNA/

RNA mixture of different virus strains is labeled segment by segment each with a labeled counter-strand probe and subjected to a displacement experiment by an excess of unlabeled probe. The rapid appearance of free labeled probe below the melting temperature indicates that many strains have formed complexes with the probe exhibiting many mismatches. In these regions, the strains are evidently highly heterogeneous.

In FIG. 23, a method is depicted by which it is possible, according to the invention, to deduce the presence of at least one of several possible mutations on a genome segment simultaneously through cross correlation. A mixture of unlabeled fragments is added to the DNA or RNA mixture to be analyzed. Hybridization of probe p with dye F2 must, correlate with the simultaneous hybridization of at least one probe m1–m6 labeled with dye F1, if one of the sought mutations is present. Probes m1–m6 are each complementary to the mutated sequences and cannot efficiently form double strand structures with wild type sequences under stringent conditions. Preferred concentrations for the nucleic acid to be analyzed are from $10^{-10}$ M to $10^{-14}$ M, whereas the probes are offered in a concentration of preferably from $10^{-8}$ M to $10^{-11}$ M.

Figure 24A:
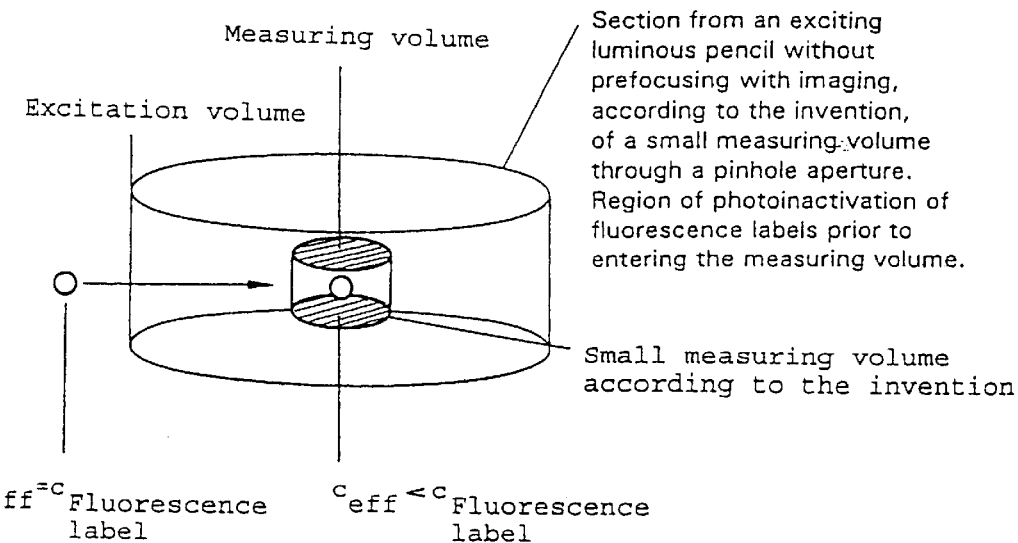
FIGS. 24a, 24b, and 24c are schematic representations of embodiments of according to the invention.
Figure 24B:
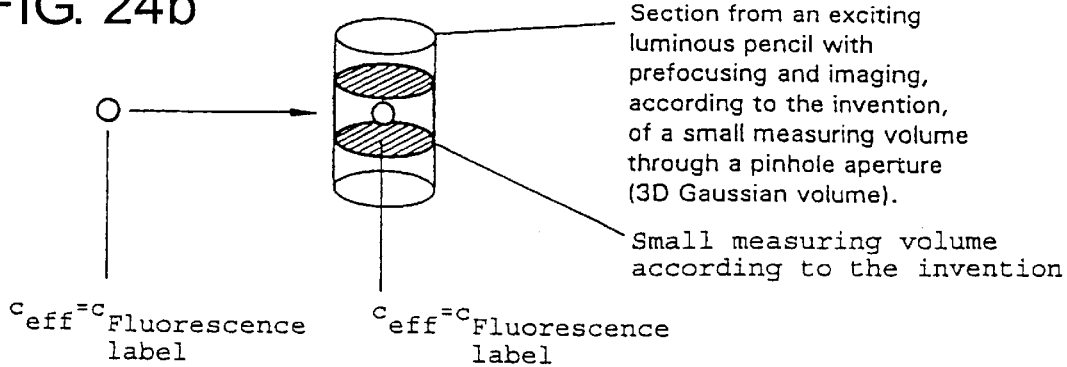
Figure 24C:
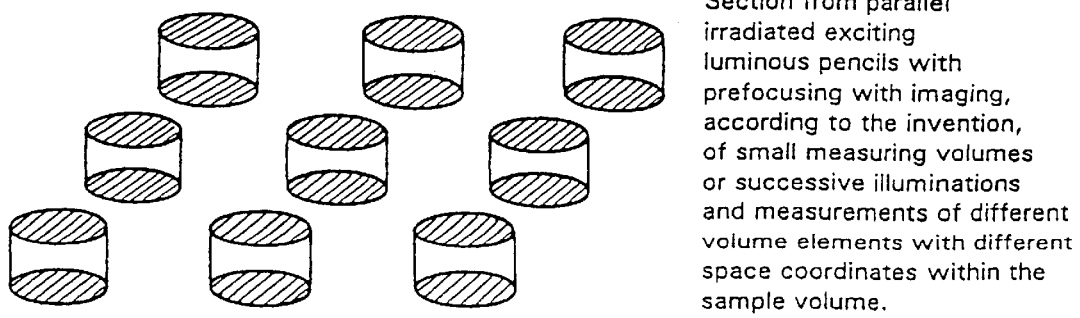

FIG. 24 schematically depicts the significance of small excitation volumes (a), small measuring volumes (b) and small volumes in parallel measurements (c) according to the invention. (a) A section from an exciting luminous pencil without prefocusing is shown with imaging of a small measuring volume according to the invention. A region is formed wherein photoinactivation of a dye label can occur prior to entering the actual measuring volume so that the effective concentration in the measuring volume is lower than the actual concentration. This is prevented to a large extent, according to the invention, by illuminating with prefocused exciting light and imaging through a pinhole aperture in the object plane. Thus, a Gaussian volume with Gaussian distribution of light intensity is formed (b). (c) shows a section from parallel irradiated exciting luminous pencils with prefocusing with preferred imaging of small measuring volumes or successive illuminations and measurements of different volume elements with different space coordinates within the sample volume.

What is claimed is:

1. A device for detecting one or more molecules, molecular complexes or molecular fragments in a measuring volume by means of fluorescence spectroscopy which device comprises:

a) a laser beam generation device for generating a laser beam with a first wavelength, b) a focusing device for focusing said laser beam onto the measuring volume wherein the laser beam is such highly focused within the measuring volume that in essence it exclusively covers the measuring volume, c) a detector device for detecting fluorescence radiation generated due to laser light excitation of one or more molecules, molecular complexes or molecular fragments in said measuring volume, d) a pinhole aperture arranged in an image plane within a beam path of fluorescence radiation confocally with respect to the measuring volume to limit the quantity of fluorescence radiation to be detected by the detector device, wherein the measuring volume is distanced from the focusing device by up to 1,000 μm.

2. The device according to claim 1 wherein said pinhole aperture has a diameter of ≦100 micrometer.

3. The device according to claim 1 wherein said molecules, molecular complexes or molecular fragments are in a dilution of ≦1 micromolar.

4. The device according to claim 1 wherein said measuring volume is ≦$10^{-14}$ liter.

5. The device according to claim 1 wherein with an image scale of 1:100, 1:60, or 1:40 between the measuring volume and the image plane and with a measuring volume having dimensions of ≦0.1 micrometer in each direction, said pinhole aperture has a diameter of about 10 micrometer, 6 micrometer, or 4 micrometer, respectively.

6. The device according to claim 1 wherein the focusing device for focusing said laser beam onto said measurement volume has a numerical aperture of ≧1.2 N.A.

7. The device according to claim 1 wherein the focusing device has a prefocusing device to prefocus the laser beam and a focussing objective lens to focus the prefocused laser beam onto the measuring volume.

8. The device according to claim 7 wherein the distance between the focussing objective lens and the measuring volume is up to 1,000 micrometer.

9. The device according to claim 7 wherein a semitransparent mirror is arranged between the prefocusing device and the focusing objective lens to deflect the prefocused laser beam on the focusing objective lens.

10. The device according to claim 9 wherein the pinhole aperture is arranged at a side of the semitransparent mirror facing away from the focusing objective lens.

11. The device according to claim 7 wherein the appliance for prefocusing are provided with a lens and an array corresponding to microscope optics wherein a collinated laser beam is focused on the image plane $B_1$ by a lens and on the image plane $B_2$ (first image) by said array.

12. The device according to claim 11 wherein said array is provided with an exchangeable arrangement of lenses for the variation of the diameter of the prefocused laser beam.

13. The device according to claim 1 wherein an optic for transmitting the fluorescence radiation has a numerical aperture of $\geq 1.2$ N.A.

14. The device according to claim 1 wherein the detector device has at least one and preferably more detectors for detecting the fluorescence radiation.

15. The device according to claim 1 wherein at least one optical filter is arranged between the pinhole aperture and the detector device.

16. The device according to claim 1 wherein at least one imaging lens is arranged between the pinhole aperture and the detector device.

17. The device according to claim 1 wherein at least one semitransparent mirror is arranged between the pinhole aperture and the detector device.

18. The device according to claim 1 wherein at least one reflecting mirror is arranged between the pinhole aperture and the detector device.

19. The device according to claim 1, further comprising
   e) an additional laser beam generation device for generating an additional laser beam with a wavelength different from the first wavelength,
   f) an additional focusing device for focusing said additional laser beam onto the measuring volume wherein the additional laser beam is such highly focused within the measuring volume that in essence it exclusively covers the measuring volume,
   g) an additional detector device for detecting fluorescence radiation generated due to excitation of one or more molecules, molecular complexes or molecular fragments, and
   h) a correlator unit which is connected with the two detector devices.

20. The device according to claim 19, further comprising
   i) a T-shaped support with a first supporting arm and a second supporting arm connected therewith and running perpendicular to the first supporting arm,
   j) two holding devices arranged at the ends at the faces of the second supporting arm for axial guiding and holding of optical elements for the two laser beams and the two fluorescence radiations wherein the focused laser beams impinge on a glass slide bearing the measuring volume and being separably arranged between the two ends at the faces of the second supporting arm and held by them,
wherein the two holding devices can be moved synchronously relative to their respective ends at the faces of the second supporting arm in a direction of a longitudinal extension thereof, the two holding devices are extended in a direction of extension of the first supporting arm, and the two laser beams can be deflected by deflecting mirrors through optical openings out of an inside of the first supporting arm onto the optical elements for the laser beams held at the holding devices.

21. The device according to claim 1, further comprising
   e) an additional laser beam generation device for generating an additional laser beam with a wavelength different from the first wavelength,
   f) an additional focusing device for focusing said additional laser beam onto the measuring volume wherein the additional laser beam is such highly focused within the measuring volume that in essence it exclusively covers the measuring volume,
   g) an additional detector device for detecting fluorescence radiation generated due to excitation of one or more molecules, molecular complexes or molecular fragments, and
   h) a correlator unit which is connected with the two detector devices.

22. The device according to claim 21, further comprising
   i) a T-shaped support with a first supporting arm and a second supporting arm connected therewith and running perpendicular to the first supporting arm,
   j) two holding devices arranged at the ends at the faces of the second supporting arm for axial guiding and holding of optical elements for the two laser beams and the two fluorescence radiations wherein the focused laser beams impinge on a glass slide bearing the measuring volume and being separably arranged between the two ends at the faces of the second supporting arm and held by them,
wherein the two holding devices can be moved synchronously relative to their respective ends at the faces of the second supporting arm in a direction of a longitudinal extension thereof, the two holding devices are extended in a direction of extension of the first supporting arm, and the two laser beams can be deflected by deflecting mirrors through optical openings out of an inside of the first supporting arm onto the optical elements for the laser beams held at the holding devices.

23. The device according to claim 21, further comprising
   i) a T-shaped support with a first supporting arm and a second supporting arm connected therewith and running perpendicular to the first supporting arm,
   j) two holding devices arranged at the ends at the faces of the second supporting arm for axial guiding and holding of optical elements for the two laser beams and the two fluorescence radiations wherein the focused laser beams impinge on a glass slide bearing the measuring volume and being separably arranged between the two ends at the faces of the second supporting arm and held by them,
wherein the two holding devices can be moved synchronously relative to their respective ends at the faces of the second supporting arm in a direction of a longitudinal extension thereof, the two holding devices are extended in a direction of extension of the first supporting arm, and the two laser beams can be deflected by semitransparent mirrors through optical openings out of an inside of the firs supporting arm onto the optical elements for the laser beams held at the holding devices.

24. The device according to claim 21 wherein the focused laser beams are being separably arranged halfway between the two ends at the faces of the second supporting arm.

25. The device according to claim 21 wherein the optical elements for the laser beams are arranged at the inner sides, facing each other, of the two holding devices and the optical elements for the fluorescence radiation are arranged at the outer sides, facing away from each other, of the two holding devices.

26. The device according to claim 21 wherein one of the focusing objective lenses can be positioned by an adjusting element for compensation of an offset of the focuses of said focusing objective lenses.

27. The device according to claim 26 wherein the adjusting element is piezoelectrically driven.

28. The device according to claim 1 wherein the observation unit has photon counting appliances, a correlation appliance, and a multichannel scaler appliance.

29. The device according to claim 28 comprising computer assisted means for processing or evaluating the measuring signal.

30. The device according to claim 1 wherein a detection unit is constituted by two detectors with a beam splitter partitioning the light emitted from the sample to the detectors.

31. The device according to claim 30 wherein the emitted light beam passes imaging lenses and filter elements prior to each of the detectors.

32. The device according to claim 30 wherein the detectors detect light of different wavelengths.

33. The device according to claim 1 comprising two objectives which form an angle of >90° between them.

34. The device according to claim 1 wherein the laser beam generation device comprises a continuous laser emitting light of wavelengths >200 nm.

35. The device according to claim 34 wherein the laser is an argon, krypton, helium-neon, or helium-cadmium laser.

36. The device according to claim 1 wherein the laser beam generation device comprises a laser pulsed with high frequency of $\geq 20$ MHz with a power of $\geq 0.5$ mW.

37. The device according to claim 1 wherein appliances for single photon counting are arranged in the beam path of emitted light for detecting the emitted light wherein signal analysis is performed by a digital correlator or multichannel correlator.

38. The device according to claim 37 wherein said appliances for single photon counting are avalanche diode detectors.

39. The device according to claim 37 wherein said appliances for single photon counting are arranged in the plane of the pinhole aperture.

40. The device according to claim 1 wherein the measuring volume is situated in a sample volume between two capillaries, said capillaries being provided with a chemically inert conductive coating at the outer side, and wherein the conductive coatings are connected via a computer controlled rectified field or an alternating field and are conductively connected with each other through the measuring volume.

41. The device according to claim 40 wherein the coating is a metal vapor deposited coating.

42. The device according to claim 41 wherein the coating is a gold vapor deposited coating on a chromium priming.

43. The device according to claim 1 wherein two microscope optics facing each other enclose the measuring volume.

44. The device according to claim 1, further comprising an electrophoretic device with at least one electrophoresis cell having at least one opening for charging/discharging of a sample to be analyzed into the measuring volume or of a washing solution, a wall electrode, a ring electrode, a Neher capillary, an electrode at the tip of the capillary and a droplet outlet.

45. The device according to claim 44 comprising an electric trap having a quadrupole element with at least four electrodes.

46. The device according to claim 45 the quadrupole element includes pin electrodes or vapor-deposited electrodes in a water configuration wherein a hole of <1 mm is lined.

47. The device according to claim 45 further comprising at least two additional electrodes in at least a sextupole arrangement.

48. The device according to claim 47 wherein the quadrupole element is provided with alternating voltage and a direct voltage is applied to the sextupole electrodes such that the polarity thereof is opposed to the charge of the molecules to be analyzed.

49. The device according to claim 44 further comprising a sheet for receiving samples, said sheet having specific binding properties for molecules due to molecular derivatization.

50. The device according to claim 49 wherein the molecular derivatization includes ion-exchange ligands or affinity ligands.

51. The device according to claim 50 wherein said ligands are oligopeptides, polypeptides, proteins, antibodies or chelating agents, especially iminodiacetic acid or nitriloacetic acid ligands.

52. The device according to claim 49, comprising sheets having different molecular structures of different binding specificity as ligands in specific positions.

53. The device according to claim 44 wherein the sample comprising one or more molecules, molecular complexes or molecular fragments to be detected is fixed on a sample receiving device which is two- or three-dimensionally controllable.

54. The device according to claim 53 wherein the sample receiving device comprises two- or three-dimensional piezo drives to fix the sample in defined space coordinates.

55. The device according to claim 44 wherein said device is equipped with an appliance which deflects the laser beam in defined coordinates.

56. The device according to claim 44 wherein said device is equipped with an appliance which can definitely determine the positioning of focusing.

57. The device according to claim 1 wherein the detector device comprises a multiarray detector.

58. The device according to claim 1 comprising an optical system for the parallel illumination of several measuring volumes.

59. The device according to claim 1 wherein said pinhole aperture has a diameter of $\leq 30$ micrometer.

60. A device for detecting one or more molecules, molecular complexes or molecular fragments in a measuring volume by means of fluorescence spectroscopy which device comprises:
   a) a laser beam generation device for generating a laser beam with a first wavelength,
   b) a focusing device for focusing said laser beam onto the measuring volume wherein the laser beam is such highly focused within the measuring volume that in essence it exclusively covers the measuring volume,
   c) a detector device for detecting fluorescence radiation generated due to laser light excitation of one or more molecules, molecular complexes or molecular fragments, said detector device being arranged in an image plane within a beam path of fluorescence radiation confocally with respect to the measuring volume to limit the quantity of fluorescence radiation to be detected,
wherein the measuring volume is distanced from the focusing device by up to 1,000 micrometer.

61. The device according to claim 60 wherein said pinhole aperture has a diameter of $\leq 100$ micrometer.

62. The device according to claim 60 wherein said molecules, molecular complexes or molecular fragments are in a dilution of $\leq 1$ micromolar.

63. The device according to claim 60 wherein said measuring volume is $\leq 10^{-14}$ liter.

64. The device according to claim 60 wherein with an image scale of 1:100, 1:60, or 1:40 between the measuring volume and the image plane and with a measuring volume having dimensions of ≦0.1 micrometer in each direction, said pinhole aperture has a diameter of about 10 micrometer, 6 micrometer, or 4 micrometer, respectively.

65. The device according to claim 60 wherein the focusing device for focusing said laser beam onto said measurement volume has a numerical aperture of ≧1.2 N.A.

66. The device according to claim 60 wherein the focusing device has a prefocusing device to prefocus the laser beam and a focusing objective lens to focus the prefocused laser beam onto the measuring volume.

67. The device according to claim 66 wherein the distance between the focusing objective lens and the measuring volume is up to 1,000 micrometer.

68. The device according to claim 66 wherein a semitransparent mirror is arranged between the prefocusing device and the focusing objective lens to deflect the prefocused laser beam on the focusing objective lens.

69. The device according to claim 68 wherein the pinhole aperture is arranged at a side of the semitransparent mirror facing away from the focusing objective lens.

70. The device according to claim 66 wherein the appliances for prefocusing are provided with a lens and an array corresponding to microscope optics wherein a collineated laser beam is focused on the image plane $B_1$ by a lens and on the image plane $B_2$ (first image) by said array.

71. The device according to claim 70 wherein said array is provided with an exchangeable arrangement of lenses for the variation of the diameter of the prefocused laser beam.

72. The device according to claim 60 wherein an optic for transmitting the fluorescence radiation has a numerical aperture of ≧1.2 N.A.

73. The device according to claim 60 wherein the detector device has one or more detectors for detecting the fluorescence radiation.

74. The device according to claim 60 wherein at least one optical filter is arranged between the pinhole aperture and the detector device.

75. The device according to claim 60 wherein at least one imaging lens is arranged between the pinhole aperture and the detector device.

76. The device according to claim 60 wherein at least one semitransparent mirror is arranged between the pinhole aperture and the detector device.

77. The device according to claim 60 wherein at least one reflecting mirror is arranged between the pinhole aperture and the detector device.

78. The device according to claim 60 wherein one or more detector elements are placed in the image plane in the form of a detector array.

79. The device according to claim 60 wherein the observation unit has photon counting appliances, a correlation appliance, and a multichannel scaler appliance.

80. The device according to claim 79 comprising computer assisted means for processing or evaluating the measuring signal.

81. The device according to claim 60 wherein a detection unit is constituted by two detectors with a beam splitter partitioning the light emitted from the sample to the detectors.

82. The device according to claim 81 wherein the emitted light beam passes imaging lenses and filter elements prior to each of the detectors.

83. The device according to claim 81 wherein the detectors detect light of different wavelengths.

84. The device according to claim 60 comprising two objectives which form an angle of >90° between them.

85. The device according to claim 60 wherein the laser beam generation device comprises a continuous laser emitting light of wavelengths >200 nm.

86. The device according to claim 85 wherein the laser is an argon, krypton, helium-neon, or helium-cadmium laser.

87. The device according to claim 60 wherein the laser beam generation device comprises a laser pulsed with high frequency of ≧20 MHz with a power of ≧0.5 mW.

88. The device according to claim 60 wherein appliances for single photon counting are arranged in the beam path of emitted light for detecting the emitted light wherein signal analysis is performed by a digital correlator or multichannel correlator.

89. The device according to claim 88 wherein said appliances for single photon counting are avalanche diode detectors.

90. The device according to claim 88 wherein said appliances for single photon counting are arranged in the plane of the pinhole aperture.

91. The device according to claim 60 wherein the measuring volume is situated in a sample volume between two capillaries, said capillaries being provided with a chemically inert conductive coating at the outer side, and wherein the conductive coatings are connected via a computer controlled rectified field or an alternating field and are conductively connected with each other through the measuring volume.

92. The device according to claim 91 wherein the coating is a metal vapor deposited coating.

93. The device according to claim 92 wherein the coating is a gold vapor deposited coating on a chromium priming.

94. The device according to claim 60 wherein two microscope optics facing each other enclose the measuring volume.

95. The device according to claim 60, further comprising an electrophoretic device with at least one electrophoresis cell having at least one opening for charging/discharging of a sample to be analyzed into the measuring volume or of a washing solution, a wall electrode, a ring electrode, a Neher capillary, an electrode at the tip of the capillary and a droplet outlet.

96. The device according to claim 95 comprising an electric trap having a quadrupole element with at least four electrodes.

97. The device according to claim 96 the quadrupole element includes pin electrodes or vapor-deposited electrodes in a water configuration wherein a hole of <1 mm is lined.

98. The device according to claim 96 further comprising at least two additional electrodes in at least a sextupole arrangement.

99. The device according to claim 98 wherein the quadrupole element is provided with alternating voltage and a direct voltage is applied to the sextupole electrodes such that the polarity thereof is opposed to the charge of the molecules to be analyzed.

100. The device according to claim 95 further comprising a sheet for receiving samples having specific binding properties for molecules due to molecular derivatization.

101. The device according to claim 100 wherein the molecular derivatization includes ion-exchange ligands or affinity ligands.

102. The device according to claim 101 wherein said ligands are oligopeptides, polypeptides, proteins, antibodies or chelating agents, especially iminodiacetic acid or nitrilo-acetic acid ligands.

103. The device according to claim 100 comprising sheets having different molecular structures of different binding specificity as ligands in specific positions.

104. The device according to claim 95 wherein the sample comprising one or ore molecules, molecular complexes or molecular fragments to be detected is fixed on a sample receiving device which is two- or three-dimensionally controllable.

105. The device according to claim 104 wherein the sample comprises two- or three-dimensional piezo drives to fix the sample in defined space coordinates.

106. The device according to claim 95 wherein said device is equipped with an appliance which deflects the laser beam in defined coordinates.

107. The device according to claim 95 wherein said device is equipped with an appliance which can definitely determine the positioning of focusing.

108. The device according to claim 60 wherein the detector device comprises a multiarray detector.

109. The device according to claim 60 comprising an optical system for the parallel illumination of several measuring volumes.

110. The device according to claim 60 wherein said pinhole aperture has a diameter of ≦30 micrometer.

111. The device according to claim 60, further comprising e) an additional laser beam generation device for generating an additional laser beam with a wavelength different from the first wavelength, f) an additional focusing device for focusing said additional laser beam onto the measuring volume wherein the additional laser beam is such highly focused within the measuring volume that in essence it exclusively covers the measuring volume, g) an additional detector device for detecting fluorescence radiation generated due to excitation of one or more molecules, molecular complexes or molecular fragments, and b) a correlator unit which is connected with the two detector devices.

112. The device according to claim 111 wherein the focused laser beams are being separably arranged halfway between the two ends at the faces of the second supporting arm.

113. The device according to claim 111 wherein the optical elements for the laser beams are arranged at the inner sides, facing each other, of the two holding devices and the optical elements for the fluorescence radiation are arranged at the outer sides, facing away from each other, of the two holding devices.

114. The device according to claim 111 wherein one of the focusing objective lenses can be positioned by an adjusting element for compensation of an offset of the focuses of said focusing objective lenses.

115. The device according to claim 114 wherein the adjusting element is piezoelectrically driven.

* * * * *

UNITED STATES PATENT AND TRADEMARK OFFICE
CERTIFICATE OF CORRECTION

PATENT NO. : 6,582,903 B1  Page 1 of 1
APPLICATION NO. : 09/021410
DATED : June 24, 2003
INVENTOR(S) : Rigler et al.

It is certified that error appears in the above-identified patent and that said Letters Patent is hereby corrected as shown below:

On the title Page, item 62, line 2, change "PCT/EP03/01291 on May 22, 1993" to --PCT/EP94/00117 on January 18, 1994--

Signed and Sealed this

Third Day of June, 2008

JON W. DUDAS
*Director of the United States Patent and Trademark Office*

```
SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
tgaccggcag caaaatgt                                                 18
```